(12) United States Patent
Barber

(10) Patent No.: US 12,410,174 B1
(45) Date of Patent: *Sep. 9, 2025

(54) SMALL MOLECULAR INHIBITORS OF STING SIGNALING COMPOSITIONS AND METHODS OF USE

(71) Applicant: Glen N Barber, Miami, FL (US)

(72) Inventor: Glen N Barber, Miami, FL (US)

(73) Assignee: TYERELL IMMUNOTHERAPEUTICS INC, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/528,433

(22) Filed: Dec. 4, 2023

Related U.S. Application Data

(63) Continuation of application No. 17/246,480, filed on Apr. 30, 2021, now Pat. No. 11,897,888.

(60) Provisional application No. 63/017,984, filed on Apr. 30, 2020.

(51) Int. Cl.
*C07D 487/04* (2006.01)
*A61P 37/06* (2006.01)

(52) U.S. Cl.
CPC ............ *C07D 487/04* (2013.01); *A61P 37/06* (2018.01)

(58) Field of Classification Search
CPC ............................... C07D 487/04; A61P 37/06
See application file for complete search history.

(56) References Cited

U.S. PATENT DOCUMENTS 11,897,888 B1 * 2/2024 Barber .................... A61P 37/06

* cited by examiner

*Primary Examiner* — Paul V Ward
(74) *Attorney, Agent, or Firm* — SCI-LAW STRATEGIES, PC

(57) ABSTRACT

Compounds of the present application or pharmaceutically acceptable salts thereof are capable of interacting with and attenuating the activity of a stimulator of interferon genes (STING) protein. In an embodiment of the invention, antagonist compounds bind to STING protein and attenuate STING downstream signaling. Pharmaceutical compositions and methods involving such compounds as STING modulators are additionally provided herein.

20 Claims, 10 Drawing Sheets

Specification includes a Sequence Listing.

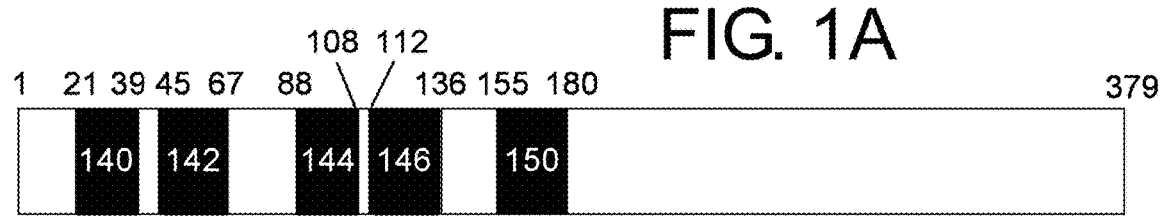
FIG. 1A
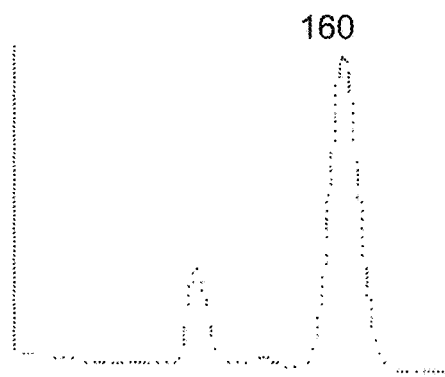
FIG. 1B
FIG. 1C
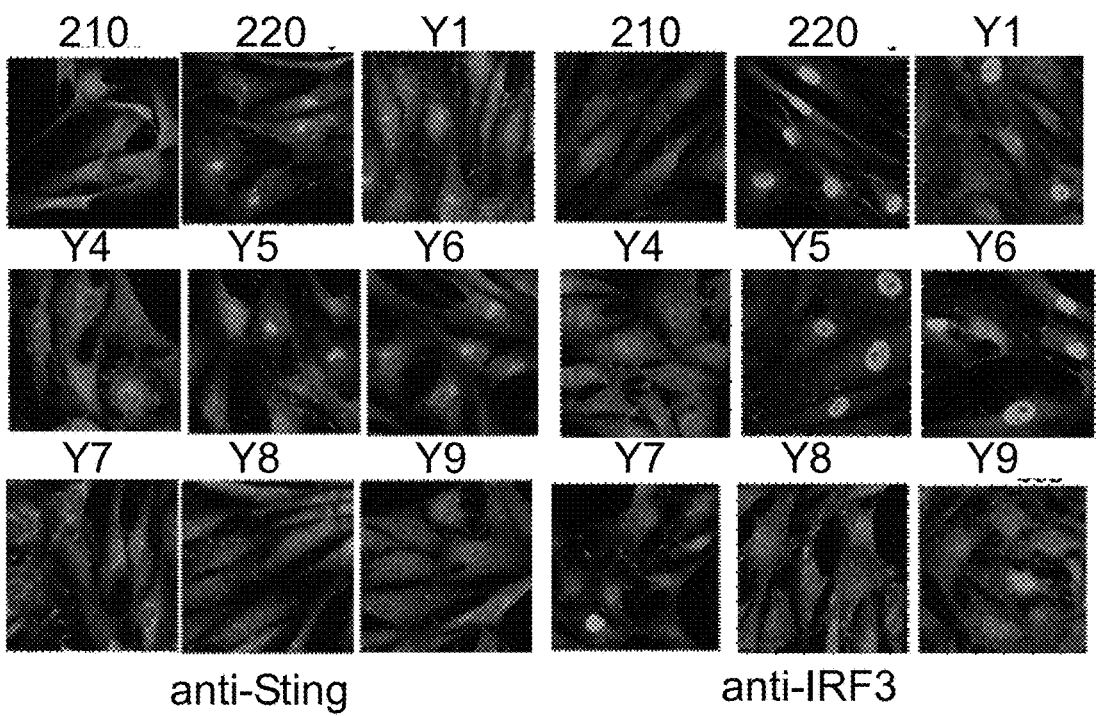
anti-Sting
FIG. 4D
anti-IRF3
FIG. 4E

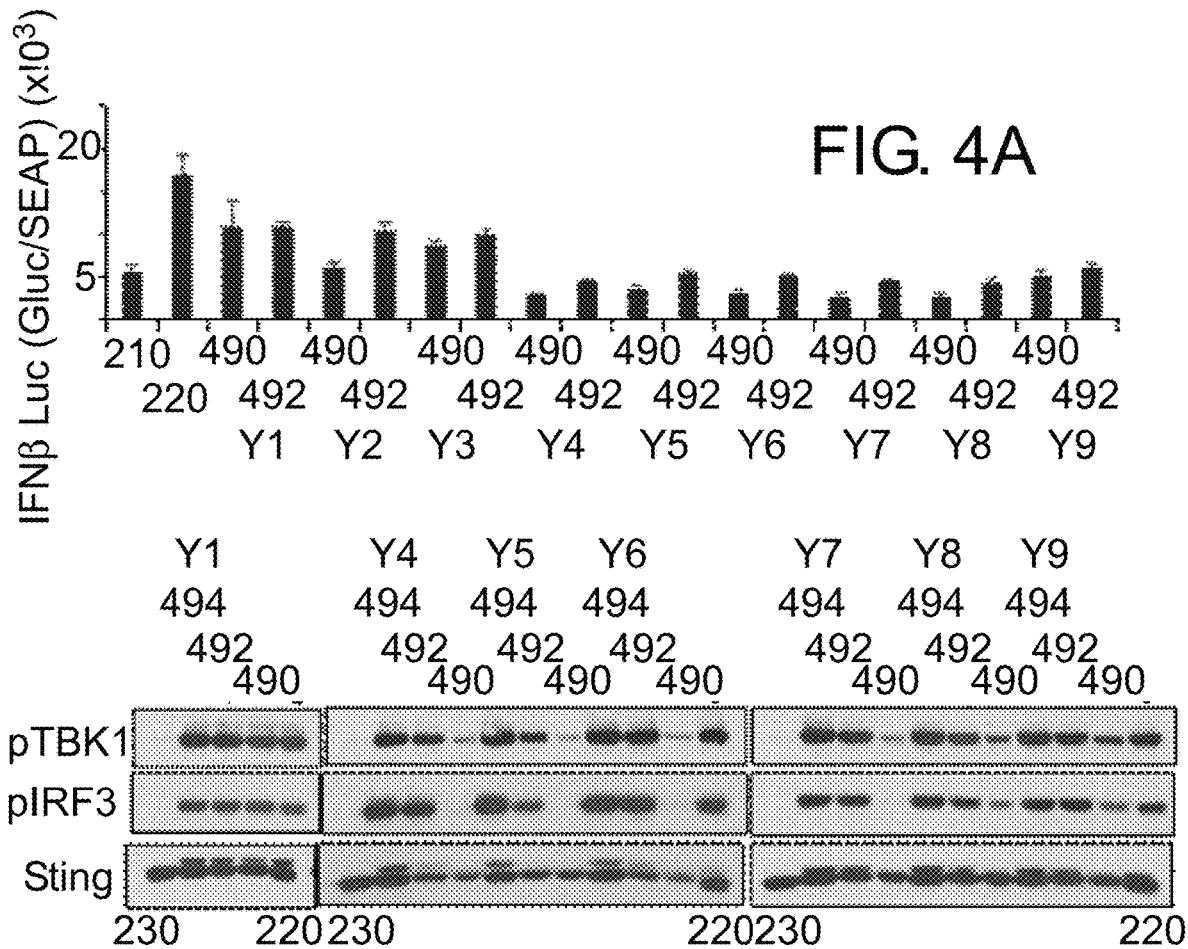
FIG. 4A
FIG. 4B
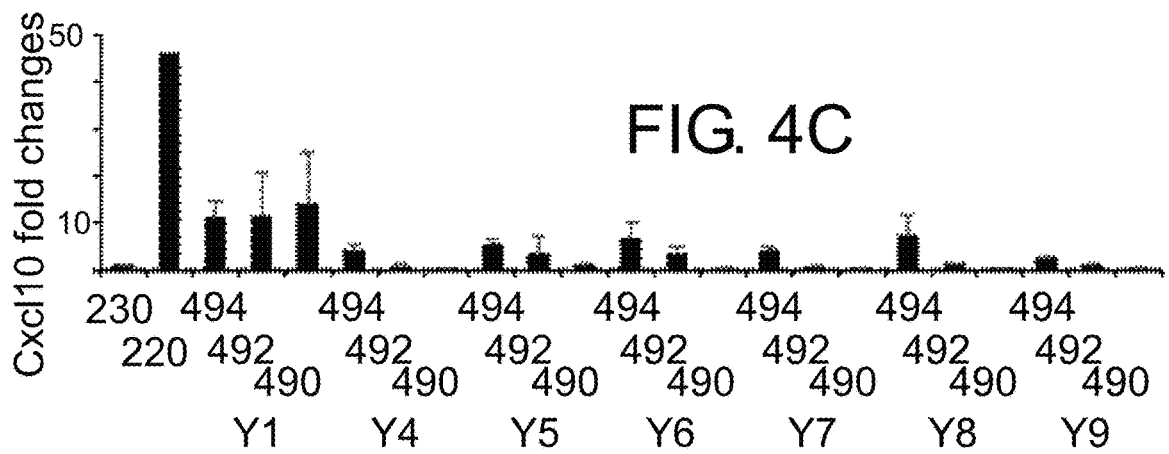
FIG. 4C

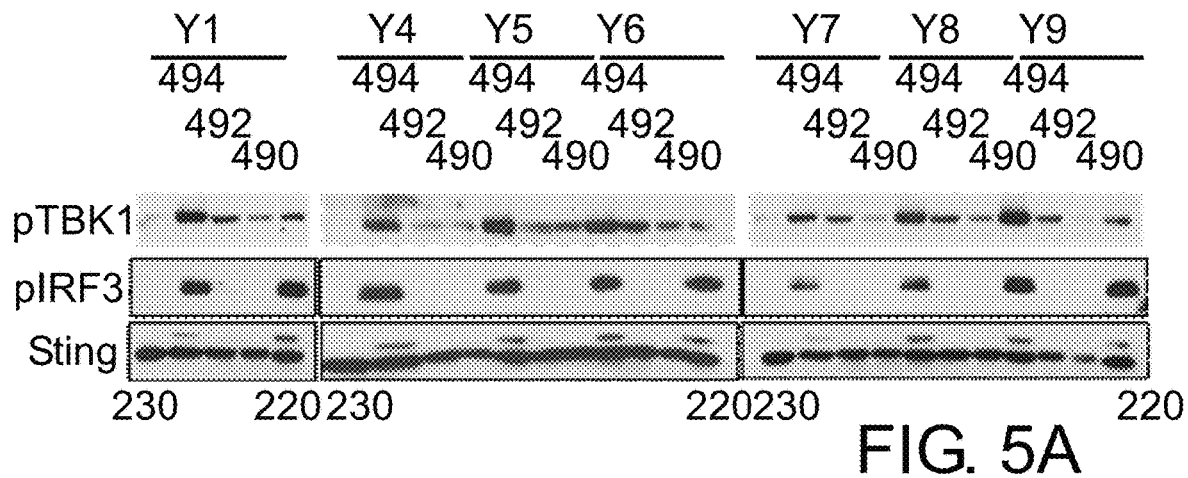
FIG. 5A
FIG. 5B
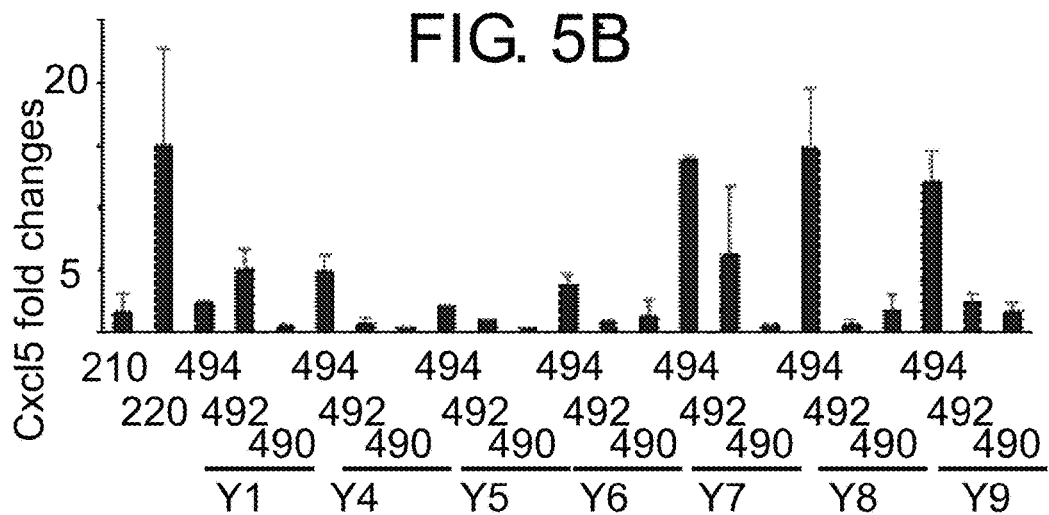
FIG. 5C
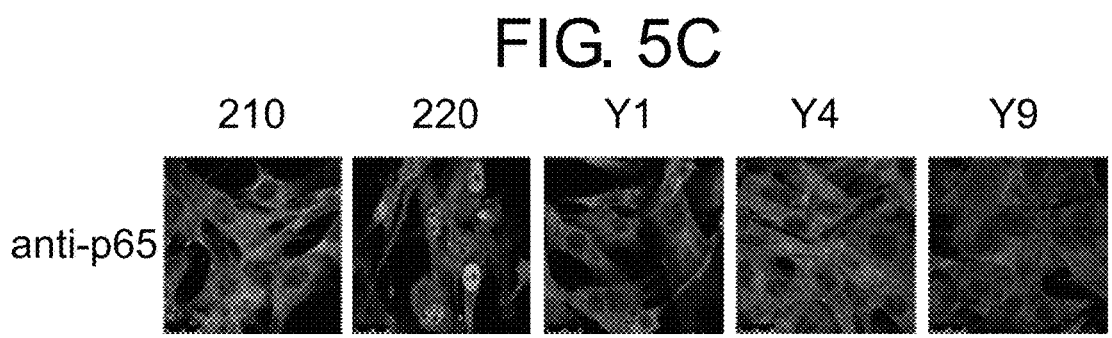

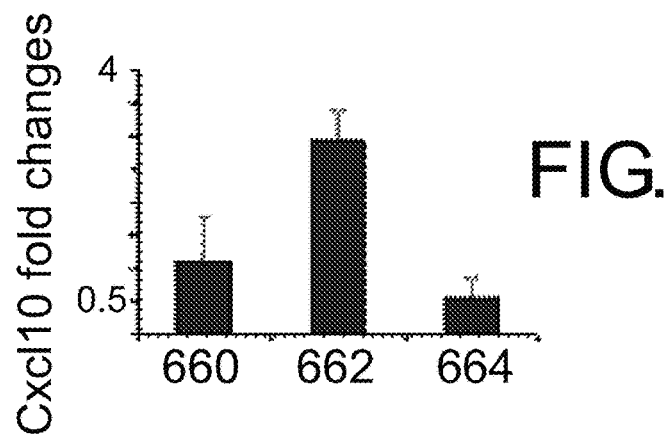
FIG. 6A
FIG. 6B
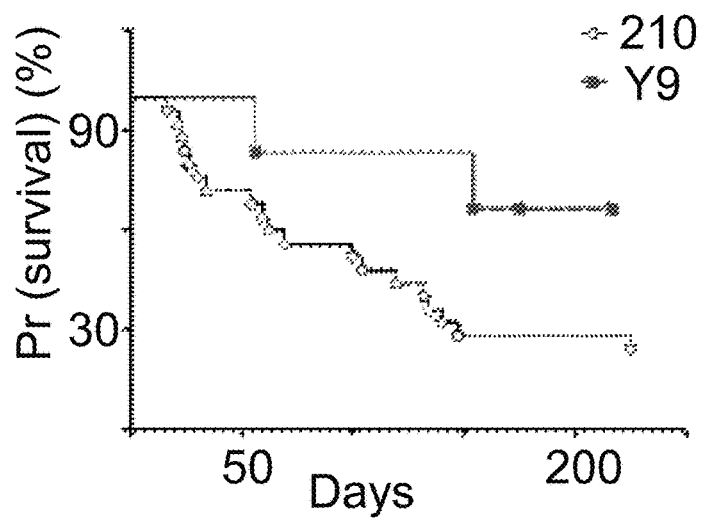
FIG. 6C
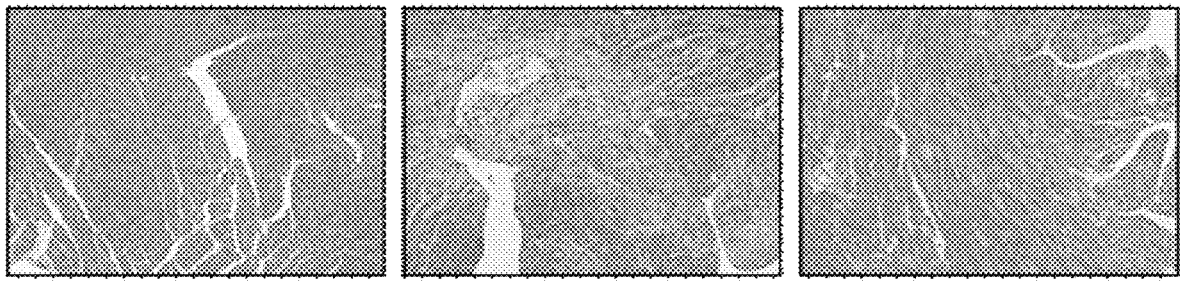

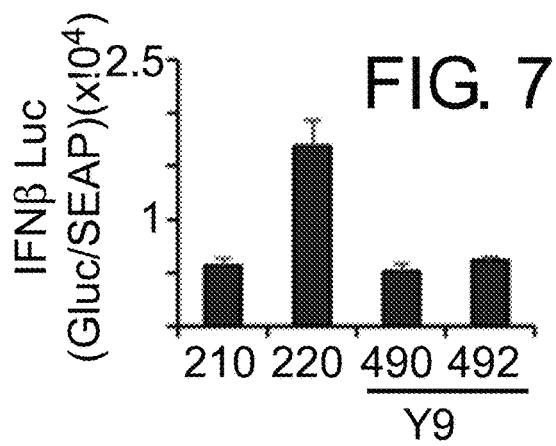
FIG. 7A
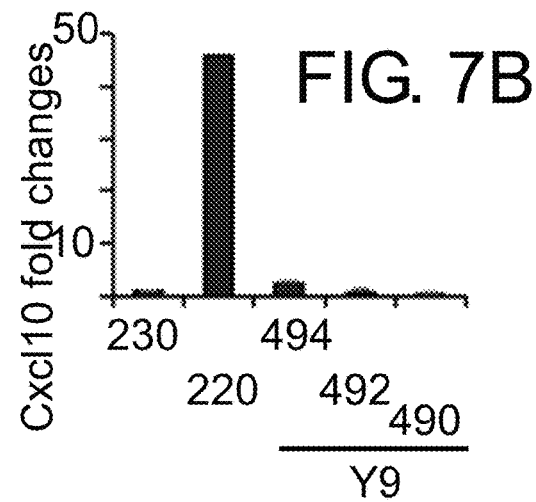
FIG. 7B
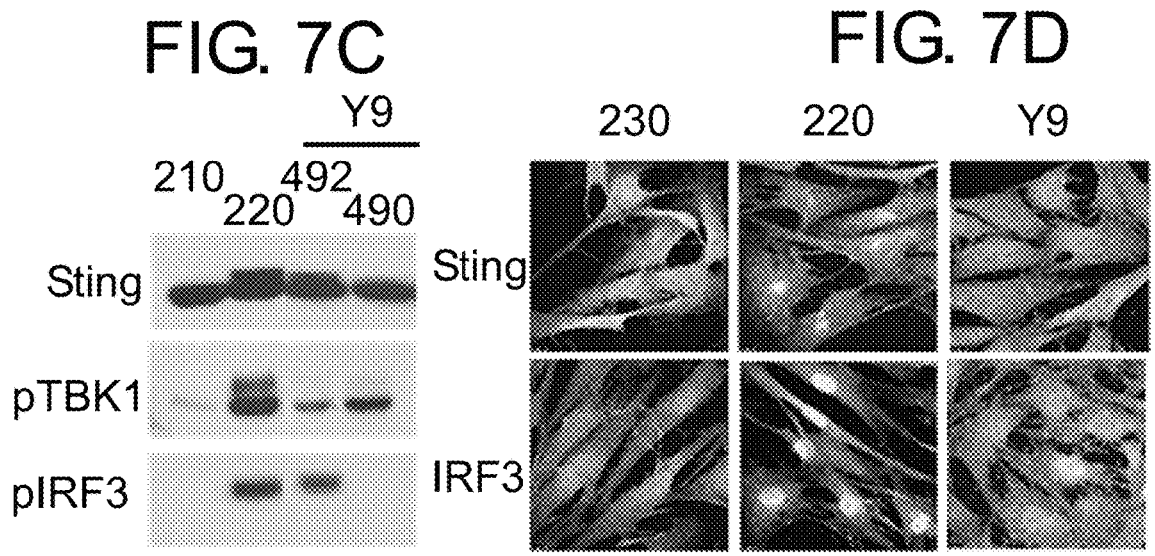
FIG. 7C
FIG. 7D

FIG. 7E
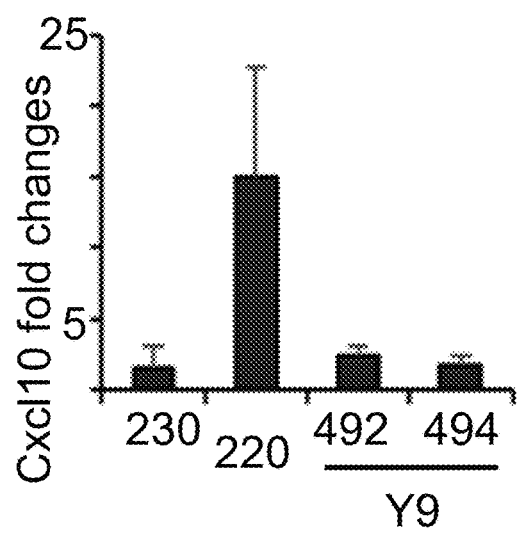
FIG. 7F
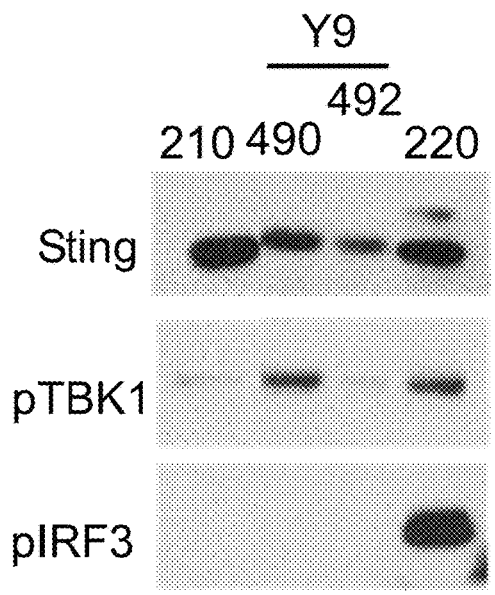
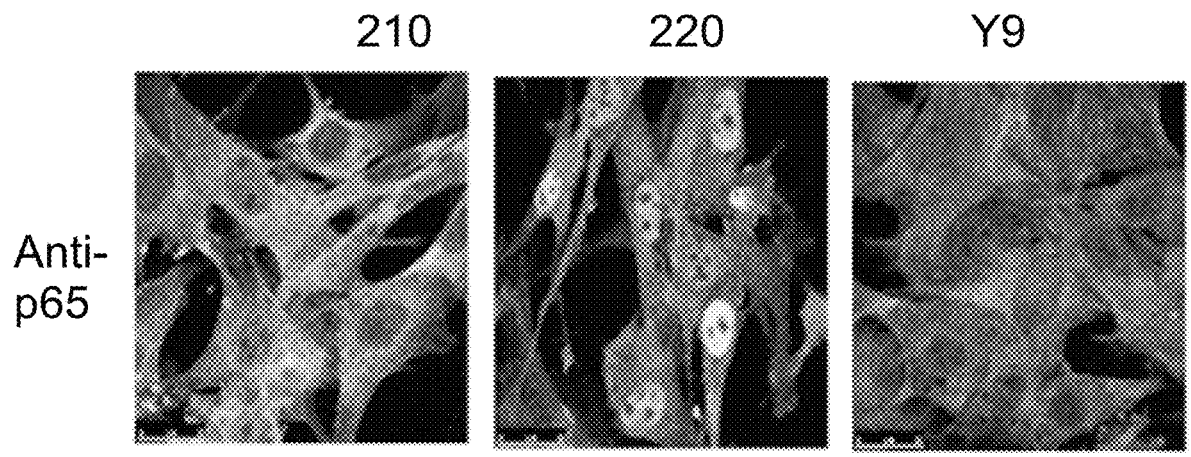
FIG. 7G

FIG. 8A
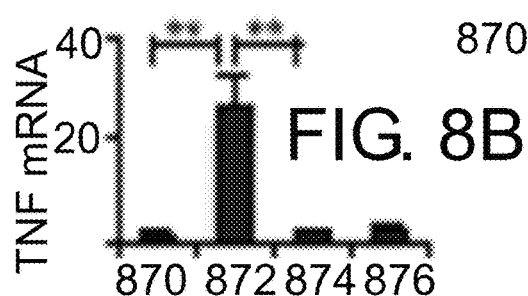
FIG. 8B
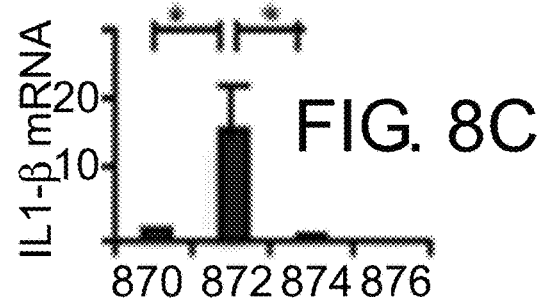
FIG. 8C
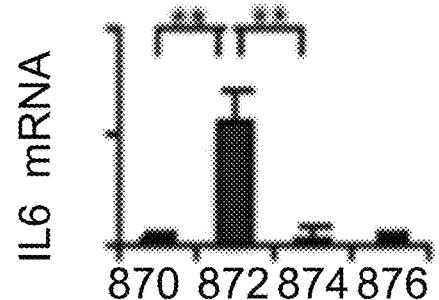
FIG. 8D
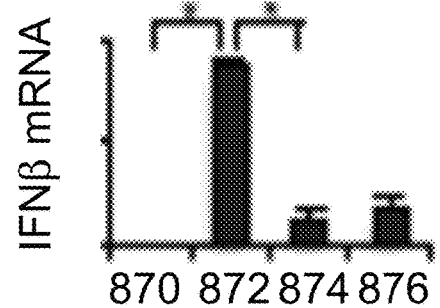
FIG. 8E

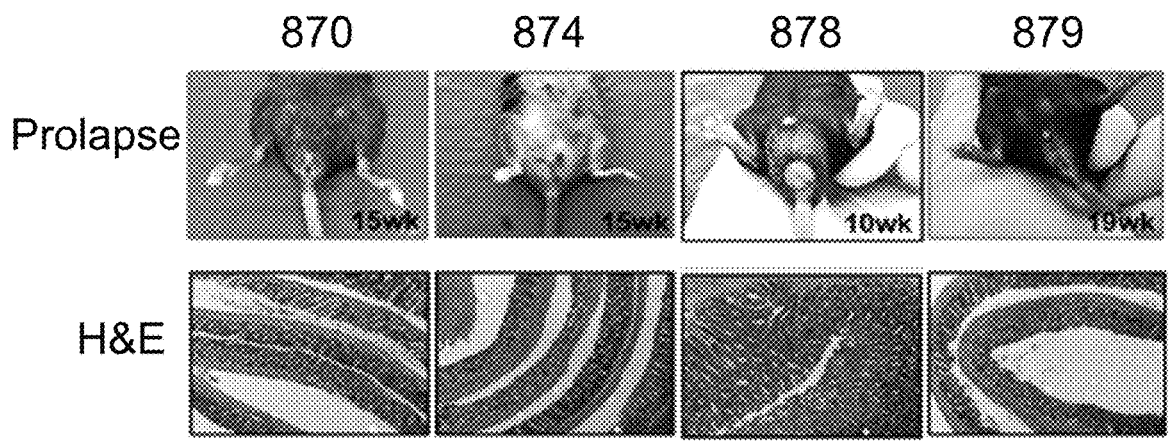
FIG. 9A
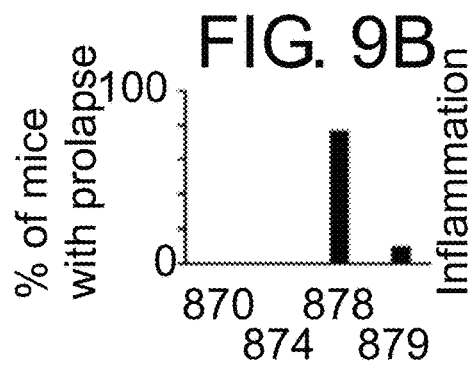
FIG. 9B
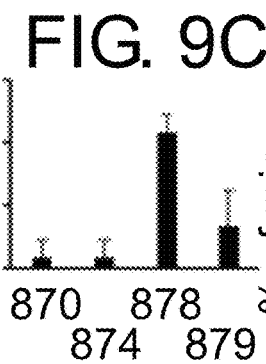
FIG. 9C
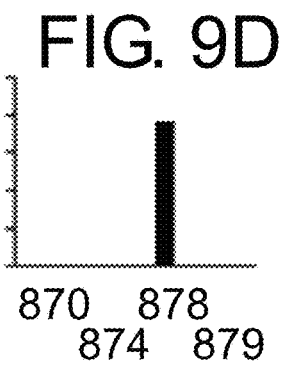
FIG. 9D
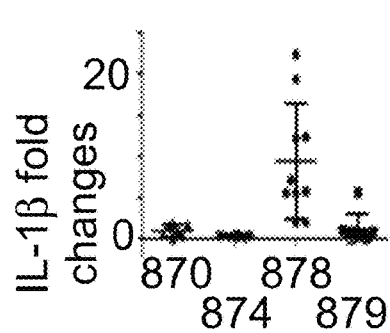
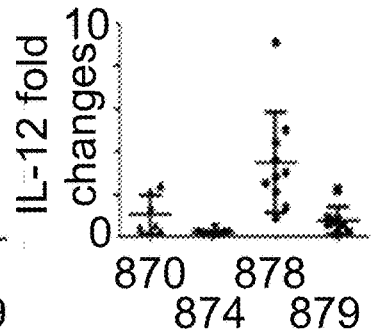
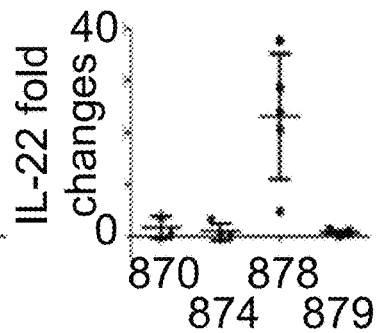
FIG. 9E          FIG. 9F          FIG. 9G

SMALL MOLECULAR INHIBITORS OF STING SIGNALING COMPOSITIONS AND METHODS OF USE

PRIORITY CLAIM

This application is a continuation of and claims priority to (i) U.S. application Ser. No. 17/246,480 entitled "SMALL MOLECULAR INHIBITORS OF STING SIGNALING COMPOSITIONS AND METHODS OF USE", inventor: Glen N. Barber filed Apr. 30, 2021 which claims priority to (ii) U.S. Provisional Application No. 63/017,984 entitled "SMALL MOLECULAR INHIBITORS OF STING SIGNALING COMPOSITIONS AND METHODS OF USE", inventor: Glen N. Barber filed Apr. 30, 2020 which applications (i)-(ii) are herein expressly incorporated by reference in their entireties and for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file STNG-01006US4_ST26.txt, created Nov. 17, 2023, 2,623 bytes, machine format IBM-PC, MS-Windows operating system, is hereby incorporated by reference.

FIELD OF THE INVENTION

The present invention relates to compositions of antagonist of stimulators of interferon genes (STING) and methods of use of said antagonists of STING.

BACKGROUND OF THE INVENTION

Human STING (STimulator of INterferon Genes) (TMEM173: NM_198282), is a 379 amino acid transmembrane harboring protein that controls innate immune signaling triggered by cytosolic DNA species generated by invading microbes. STING is robustly activated through interaction with cyclic dinucleotides (CDNs) such as cyclic-di-AMP which can be secreted by bacteria including *Listeria monocytogenes*. Conversely, cytosolic double stranded deoxyribonucleic acid (dsDNA) species which can include microbial DNA or self-DNA leaked from the nucleus are able to trigger STING signaling following binding to a 522 amino acid protein, cGAS (cyclic GMP-AMP synthase) which in the presence of ATP and GTP catalyzes the production of a type of CDN referred to as cGAMP (cyclic [G(2',5')pA(3',5')p]) containing one 2'-5' phosphodiester linkage and a canonical 3-5' linkage. CDN-binding results in STING, complexed with the IRF3 kinase TANK-binding kinase 1 (TBK1) re-locating to perinuclear regions of the cell. Association with CDN's enables STING to activate the transcription factors IRF3 and NF-κB which stimulate the production of type I interferon (IFN) and pro-inflammatory cytokines, which facilitate adaptive immunity.

SUMMARY OF THE INVENTION

In one aspect, the present application relates to a compound of Formula I:

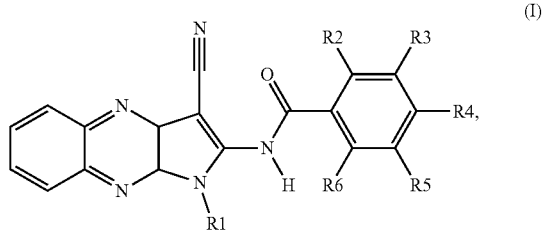

(I)

or a pharmaceutically acceptable salt, hydrate, ester, solvate, prodrug, stereoisomer, or tautomer thereof, where $R_1$ is —$CH_2$—$C_6H_5$, —$CH_2$—$CH_2$—$C_6H_5$, —$CH_2$—$CH_2$—O—$C_6H_5$, —$CH_2$—$CH_2$—O—$C_6H_4F$, —$CH_2$—$CH_2$—O—$CH_3$, where $R_2$, $R_3$, $R_4$, $R_5$ and $R_6$ are independently selected from the group consisting of —H, -halogen, —$(C_1-C_6)$ alkyl, —$(C_1-C_6)$ per halo alkyl, —$(C_3-C_6)$ cycloalkyl, —$(C_1-C_6)$ haloalkyl, —$(C_1-C_6)$ alkoxy, —$(C_1-C_6)$ haloalkoxy, —$(C_2-C_6)$ alkenyl, —$(C_2-C_6)$ alkynyl, -nitro, —CN, —OH, —COOH, —SH, —$NH_2$, —$NH(C_1-C_4)$ alkyl, and —$N((C_1-C_4)$ alkyl$)_2$.

In another aspect, the present application relates to a pharmaceutical composition comprising a therapeutically effective amount of a compound of the application and a pharmaceutically acceptable carrier.

In an embodiment of the present application a method of modulating (e.g., inhibiting or stimulating) a stimulator of interferon genes (STING) protein involves application of a STING antagonist. The method comprises administering to a subject in need thereof an effective amount of a compound of the application or a pharmaceutically acceptable salt or ester thereof, or a pharmaceutical composition of the application. In one embodiment, the STING protein is a human STING protein.

In an embodiment of the present application a method of treating or preventing a disease, wherein the diseases is caused by, or associated with, STING expression, activity, and/or function (e.g., deregulation of STING expression, activity, and/or function) involves application of a STING antagonist. The method further comprises administering to a subject in need thereof an effective amount of a STING antagonist compound of the application or a pharmaceutically acceptable salt or ester thereof, or a pharmaceutical composition of the application.

Another aspect of the present application relates to a method of treating or preventing a disease associated with deregulation of one or more of the intracellular pathways in which a STING protein is involved (e.g., deregulation of intracellular dsDNA mediated type I interferon activation). The method comprises administering to a subject in need thereof an effective amount of a STING compound of the application or a pharmaceutically acceptable salt or ester thereof, or a pharmaceutical composition of the application.

Another aspect of the present application relates to a kit comprising a compound of the application or a pharmaceutically acceptable salt or ester thereof, or a pharmaceutical composition of the application.

Another aspect of the present application relates to a compound of the application or a pharmaceutically acceptable salt or ester thereof, or a pharmaceutical composition of the application, for use in the manufacture of a medicament for modulating (e.g., inhibiting or stimulating) a STING protein, for treating or preventing a disease, wherein the diseases is caused by, or associated with, STING expression, activity, and/or function (e.g., deregulation of STING expression, activity, and/or function), or for treating or preventing a disease associated with deregulation of one or more of the intracellular pathways in which a STING protein is involved (e.g., deregulation of intracellular dsDNA mediated type I interferon activation).

Another aspect of the present application relates to use of a compound of the application or a pharmaceutically acceptable salt or ester thereof, or a pharmaceutical composition of the application, in the manufacture of a medicament for modulating (e.g., inhibiting or stimulating) a STING protein, for treating or preventing a disease, wherein the diseases is caused by, or associated with, STING expression, activity, and/or function (e.g., deregulation of STING expression, activity, and/or function), or for treating or preventing a disease associated with deregulation of one or more of the intracellular pathways in which a STING protein is involved (e.g., deregulation of intracellular dsDNA mediated type I interferon activation).

Another aspect of the present application relates to a compound of the application or a pharmaceutically acceptable salt or ester thereof, or a pharmaceutical composition of the application, for use in modulating (e.g., inhibiting or stimulating) a STING protein, in treating or preventing a disease, wherein the diseases is caused by, or associated with, STING expression, activity, and/or function (e.g., deregulation of STING expression, activity, and/or function), or in treating or preventing a disease associated with deregulation of one or more of the intracellular pathways in which a STING protein is involved (e.g., deregulation of intracellular dsDNA mediated type I interferon activation).

Another aspect of the present application relates to use of a compound of the application or a pharmaceutically acceptable salt or ester thereof, or a pharmaceutical composition of the application, in modulating (e.g., inhibiting or stimulating) a STING protein, in treating or preventing a disease, wherein the diseases is caused by, or associated with, STING expression, activity, and/or function (e.g., deregulation of STING expression, activity, and/or function), or in treating or preventing a disease associated with deregulation of one or more of the intracellular pathways in which a STING protein is involved (e.g., deregulation of intracellular dsDNA mediated type-1 interferon activation).

The present application provides antagonists of a STING protein that are therapeutic agents in the treatment or prevention of diseases such as cancer inflammation, and other immunological disorders.

The details of the disclosure are set forth in the accompanying description below. Although methods and materials similar or equivalent to those described herein can be used in the practice or testing of the present application, illustrative methods and materials are now described. In the case of conflict, the present specification, including definitions, will control. In addition, the materials, methods, and examples are illustrative only and are not intended to be limiting. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs.

BRIEF DESCRIPTION OF THE DRAWINGS

Various embodiments of the present invention will be described in detail based on the following Figures, where:

FIG. 1A shows the Human STING protein structure. C-terminal portion from AA 152-379 (237aa long) was cloned into the pET26B vector NdeI-XhoI sites (STING152-379H);

FIG. 1B shows STING152-379H was purified over a nickel column as described vide infra. Size Exclusion Chromatography (SEC) on eluted samples was then carried out using a SEC 200 Column. Using the calibration curve, the major peak (160, at ~60 kDa) signifies the dimer of STING 152-379;

FIG. 1C shows a photograph of a protein gel (non-denaturing) (where lane 170 is a MW Marker, where 180, 75 kDa, 182, 50 kDa, 184, 37 kDa), where the major peak of the SEC was injected in lane 160, and 2 μL of 50 mg/ml protein stock was injected in lane 162 (the predicted MW of the STING dimer is approximately 57 kDa indicated by arrow at 181;

FIG. 2A shows the inhibitory effect of Compound Y1 on cells transfected with ISD (Y1+220), of STING at 10 μM (493) and 50 μM (490) concentrations, where Y1 was placed onto hTERT-pIFNβ-Glu cells (hTERT) cells stably containing the type I IFNβ promoter driving luciferase and the CMV promoter driving SEAP) for 15 hours which had been transfected with double strand DNA at 3 μg/ml. Inhibition of IFNβ expression was measured by Luciferase induction at 24 hours after transfection of ISD, Mock is shown (210), ISD treatment only (220) was used as a control, according to an embodiment of the invention;

FIG. 2B shows IFNβ ELISA in normal hTERT cells after ISD transfection (220) or Lipo treated with DMSO (230) or Compound Y1, treatment same as in FIG. 2A, according to an embodiment of the invention;

FIG. 2C shows quantitative real time PCR (qPCR) of IFNβ1 in normal hTERT cells at 6 hours after ISD transfection with Compound Y1+220)/without (220), Mock is shown (210), treatment same as in FIG. 2A, according to an embodiment of the invention;

FIG. 2D shows photographs of Western blot analysis of STING, phospho-TBK1 (pTBK1) and phospho-IRF3 was performed at 6 hours after ISD transfection with/without Y1, Mock is shown (210), ISD treatment only (220) was used as control, treatment same as in FIG. 2A, according to an embodiment of the invention;

FIG. 3A shows qPCR analysis of Cxcl10 in murine embryonic fibroblasts (MEF) cells incubated for 15 hours with Y1+220 (50 μM) and transfected ISD at 3 μg/ml for 3 hours, Mock is shown (210), ISD treatment only (220) was used as a control, according to an embodiment of the invention;

FIG. 3B shows qPCR analysis of Cxcl5 in MEF cells incubated for 15 hours with Y1+220 (50 μM) and transfected ISD at 3 μg/ml for 3 hours, Mock is shown (210), ISD treatment only (220) was used as a control, according to an embodiment of the invention;

FIG. 3C shows IFNβ ELISA with Y1 or DMSO treatment only (230) on MEF cells with either Mock (210), or ISD treatment (220), treated same as in FIG. 3A, according to an embodiment of the invention;

FIG. 3D shows photographs of Western blot analysis of Sting, TBK1 phosphorylation and IRF3 phosphorylation in MEF cells with Y1+220, Mock is shown (210), ISD treatment only (220) was used as control, treated same as in FIG. 3A, according to an embodiment of the invention;

FIG. 4A shows inhibition of IFNβ expression measured by Luciferase induction at 24 hours after transfection ISD in hTERT cells treated with analogs (Y1, Y2, Y3, Y4, Y5, Y6, Y7, Y8 and Y9 at 50 μM (490) or 25 μM (492)) for 15 hours, where the cells were transfected ISD at 3 μg/ml, Mock is shown (210), ISD treatment only (220) was used as control, according to an embodiment of the invention;

FIG. 4B are photographs showing Western blot analysis for pTBK1, pIRF3, and STING performed at 6 hours after ISD transfection with analogs Y1, Y4, Y5, Y6, Y7, Y8 and Y9 at 50 μM (490), 25 μM (492) or 5 μM (494), DMSO is shown (230), ISD treatment only (220) was used as control, according to an embodiment of the invention;

FIG. 4C shows qPCR of Cxcl10 MEF cells incubated for 15 hours and transfected ISD) treated with analogs Y1, Y4, Y5, Y6, Y7, Y8 and Y9 at 50 μM (490), 25 μM (492) or 5 μM (494) at 6 hours after ISD, DMSO is shown (230), ISD treatment only (220) was used as control, according to an embodiment of the invention;

FIG. 4D are photographs showing confocal analysis for STING trafficking performed at 6 hours after ISD transfection with analogs Y1, Y4, Y5, Y6, Y7, Y8 and Y9, Mock is shown (210), ISD treatment only (220) was used as control, treated same as in FIG. 4A, according to an embodiment of the invention;

FIG. 4E are photographs showing confocal analysis for IRF3 translocation performed at 6 hours after ISD transfection with analogs Y1, Y4, Y5, Y6, Y7, Y8 and Y9, Mock is shown (210), ISD treatment only (220) was used as control, treated same as in FIG. 4A, according to an embodiment of the invention;

FIG. 5A are photographs showing Western blot analysis of pTBK1, pIRF3, and STING, performed 6 hours after ISD transfection of MEF cells treated with analogs Y1, Y4, Y5, Y6, Y7, Y8 and Y9 at 50 μM (490), 25 μM (492) or 5 μM (494), DMSO is shown (230), ISD treatment only (220) was used as control, treated same as in FIG. 2A, according to an embodiment of the invention;

FIG. 5B shows the inhibition of Cxcl10 expression in MEF cells with analogs Y1, Y4, Y5, Y6, Y7, Y8 and Y9 at 50 μM (490), 25 μM (492) or 5 μM (494), as measured by qPCR at 6 hours after transfection of ISD, Mock is shown (210), ISD treatment only (220) was used as control, treated same as in FIG. 2A, according to an embodiment of the invention;

FIG. 5C are photographs showing confocal analysis for p65 translocation in MEF cells with analogs Y1, Y4 and Y9 performed at 6 hours after ISD transfection, Mock is shown (210), ISD treatment only (220) was used as control, treated same as in FIG. 2A, according to an embodiment of the invention;

FIG. 6A shows a qPCR analysis of Cxcl10 expression in TREX1 KnockOut (TKO) mice bone marrow derived macrophages (BMDM) treated with Wild Type (WT) Mac DMSO (660), TKO Mac DMSO (662) or TKO Mac compound Y1 (664), which shows compound Y1 inhibits TREX1 dependent Cxcl10 expression, according to an embodiment of the invention;

FIG. 6B shows survival rates of 4 week old TKO mice, intraperitoneally administered analog Y9 (25 μg/mouse) 2 times a week for 5 months, according to an embodiment of the invention;

FIG. 6C shows hematoxylin and eosin (H&E) staining in the heart of TKO mice treated with analog Y9, Control is shown (210), where WT mice treated with analog Y9 (680) were also used as control, according to an embodiment of the invention;

FIG. 7A shows the Inhibition of IFNβ expression measured by Luciferase induction at 24 hours to characterize analog Y9 at 50 μM (490), 25 μM (492) or 5 μM (494) that inhibit STING signaling, where Y9 was placed onto hTERT cells, Mock is shown (210), ISD treatment only (220) was used as control, treated same as in FIG. 2A, according to an embodiment of the invention;

FIG. 7B shows a qPCR analysis of Cxcl10 expression in hTERT cells treated with Y9 at 50 μM (490) or 25 μM (492), DMSO is shown (230), ISD treatment only (220) was used as control, treated same as in FIG. 2A, according to an embodiment of the invention;

FIG. 7C are photographs showing Western blot analysis of STING, pTBK1 and pIRF3 on hTERT cells treated with Y9 at 50 μM (490) or 25 μM (492), Mock is shown (210), ISD treatment only (220) was used as control, treated same as in FIG. 2A, according to an embodiment of the invention;

FIG. 7D are photographs showing confocal analysis for STING trafficking and translocation of IRF-3 performed at 6 hours after ISD transfection with Y9, DMSO is shown (230), ISD treatment only (220) was used as control, treated same as in FIG. 2A, according to an embodiment of the invention;

FIG. 7E shows qPCR analysis of Cxcl10 where Y9 at 50 μM (490) or 25 μM (492) were placed onto MEF cells, DMSO is shown (230), ISD treatment only (220) was used as control, cells treated same as in FIG. 3A, according to an embodiment of the invention;

FIG. 7F are photographs showing Western blot analysis of STING, TBK1 phosphorylation and IRF3 phosphorylation with Y9 at 50 μM (490) or 25 μM (492) placed onto MEF cells, Mock is shown (210), ISD treatment only (220) was used as control, treated same as in FIG. 2A, according to an embodiment of the invention;

FIG. 7G are photographs showing confocal analysis for p65 translocation with Y9 placed onto MEF cells, Mock is shown (210), ISD treatment only (220) was used as control, cells treated same as in FIG. 2A, according to an embodiment of the invention;

FIG. 8A are photographs showing Immunoblot of STING and TREX1 in heart from WT (870), TKO(872), Sting−/− Trex1+/+(SKO) (874), and Sting−/− Trex1−/− STKO (876) mice;

FIG. 8B shows qPCR analysis of TNF in heart tissue from WT (870), TKO (872), STKO (874), and SKO (876) mice, according to an embodiment of the invention;

FIG. 8C shows qPCR analysis of IL-1β, in heart tissue from WT (870), TKO (872), STKO (874), and SKO (876) mice, according to an embodiment of the invention;

FIG. 8D shows qPCR analysis of IL-6 in heart tissue from WT (870), TKO (872), STKO (874), and SKO (876) mice, according to an embodiment of the invention;

FIG. 8E shows qPCR analysis of IFN-β in heart tissue from WT (870), TKO (872), STKO (874), and SKO (876) mice, according to an embodiment of the invention;

FIG. 9A shows representative photographs of either prolapse or H&E staining from WT (15 week) (870), SKO (15 week) (874), IL10 KO (10 week) (878), and IL10KO/SKO (19 week) (879) mice showing that IL-10 suppresses STING-Induced Inflammatory Colitis and CAC, according to an embodiment of the invention;

FIG. 9B shows percentage of mice with prolapse for WT (870), SKO (874), IL10 KO (878), and IL10 KO/SKO (879) mice, according to an embodiment of the invention;

FIG. 9C shows inflammation score for WT (870), SKO (874), IL10 KO (878), and IL10 KO/SKO (879) mice, according to an embodiment of the invention;

FIG. 9D shows the % of mice with polyps in 10-19-week-old WT (n=10) (870), SKO (n=15) (874), IL10KO (n=26) (878), and IL10KO/SKO mice (n=19) (879), according to an embodiment of the invention;

FIG. 9E shows qPCR of IL-1β mRNA level in each genotype of colon tissue for WT (870), SKO(874), IL10 KO (878), and IL10 KO/SKO (879) mice. All data are the mean of at least seven mice, according to an embodiment of the invention;

FIG. 9F shows qPCR of IL-12 mRNA level in each genotype of colon tissue for WT (870), SKO (874), IL10 KO (878), and IL10 KO/SKO (879) mice. All data are the mean of at least seven mice, according to an embodiment of the invention; and FIG. 9G shows qPCR of IL-22 mRNA level in each genotype of colon tissue for WT (870), SKO (874), IL10 KO (878), and IL10 KO/SKO (879) mice. All data are the mean of at least seven mice, according to an embodiment of the invention.

DETAILED DESCRIPTION OF THE INVENTION

Figure 2E:
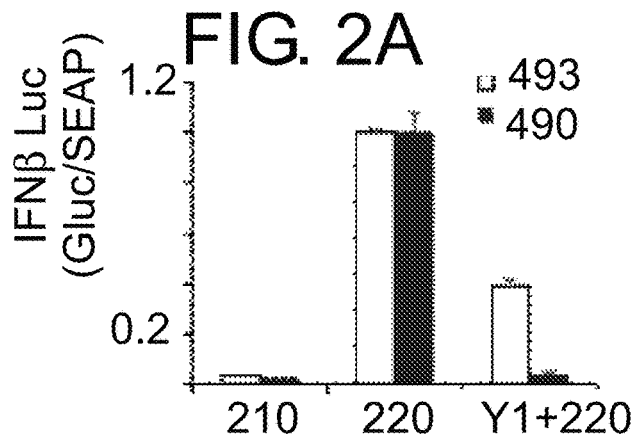
FIG. 2E are photographs showing confocal analysis of STING trafficking using anti-Sting performed at 6 hours after ISD transfection with Y1+220/without 220, Mock is shown (210), ISD treatment only (220) was used as control, treatment same as in FIG. 2A, according to an embodiment of the invention.
Figure 2E:
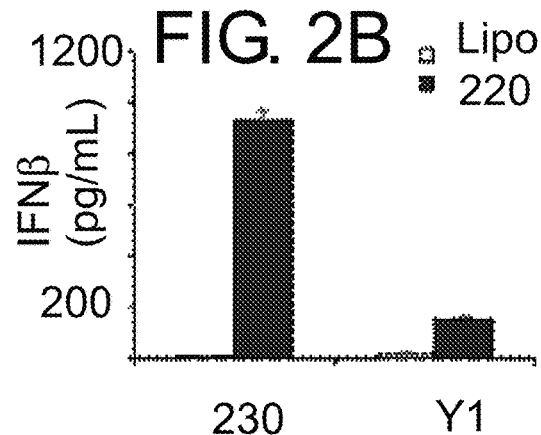
Figure 2E:
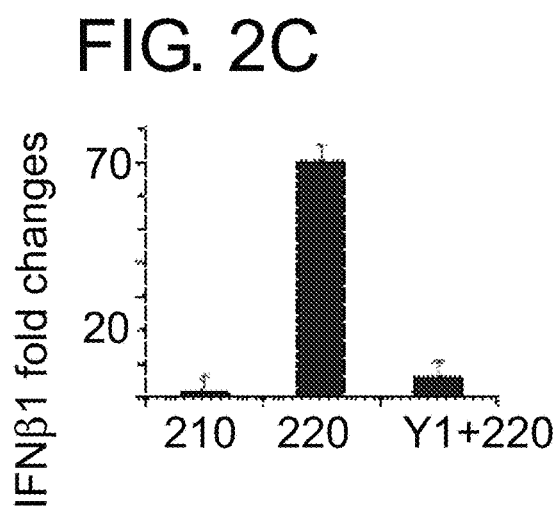
Figure 2E:
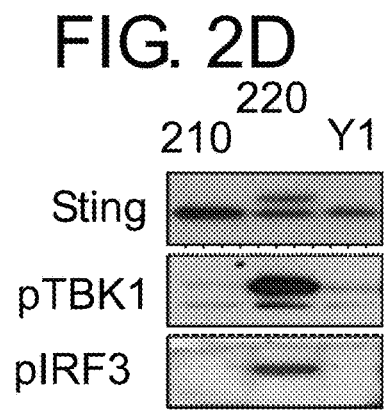
Figure 2E:
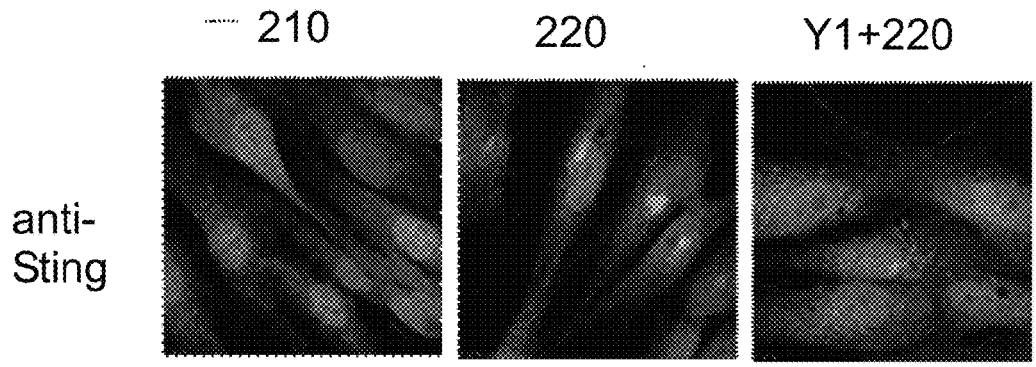

STING is a cellular innate immune receptor essential for controlling the transcription of numerous host defense genes, including type I IFN and pro-inflammatory cytokines following the recognition of CDN's or aberrant DNA species in the cytosol of the cell. The source of DNA can comprise the genome of invading pathogens such as herpes simplex 1 (HSV1) while CDNs are known to be secreted by bacteria such as *Listeria monocytogenes*. Potent activators of the STING pathway can constitute self-DNA plausibly leaked from the nucleus of the host cell itself, following cell division or even as a consequence of DNA damage. Such self-DNA may be responsible for causing a variety of autoinflammatory disease such as systemic lupus erythamatosis (SLE) or Aicardi-Goutieres Syndrome (AGS) and may even be associated with inflammation-associated cancer. Recent insight into the regulation of STING signaling has generated much needed information relating to the causes of inflammatory disease, providing new opportunities to develop novel anti-inflammatory compounds that target this pathway.

Thus, there is a need for novel small-molecule compounds that bind to and inhibit STING activity, i.e., STING antagonists. The present application addresses this need. The identified molecules impeded STING-controlled inflammatory cytokine production in murine and human cells. The compounds further demonstrated in vivo efficacy and reduced autoinflammatory disease in mice. In an embodiment of the invention, the identified molecules prevent STING-dependent and other forms of chronic innate immune driven disease. The compounds of the invention can therefore modulate the activity of STING, and accordingly, may provide a beneficial therapeutic impact in treatment of diseases, disorders and/or conditions in which modulation of STING is beneficial, for example for inflammation, graft vs host disease, allergic and autoimmune diseases, infectious diseases, cancer, and pre-cancerous syndromes.

The present application relates to compounds of Formula I that are shown to potently and selectively antagonize a STING protein (e.g., the human STING protein). In one embodiment, a compound of the present application is represented by Formula I:

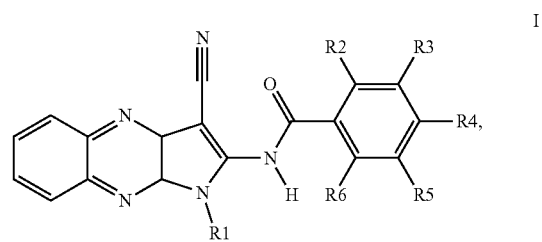

or a pharmaceutically acceptable salt, hydrate, ester, solvate, prodrug, stereoisomer, or tautomer thereof, where $R_1$ is —$(C_1$-$C_6)$ alkyl-$(C_3$-$C_6)$ cycloalkenyl, —$(C_1$-$C_6)$ alkyl-$(C_3$-$C_6)$ cycloalkyl, —$(C_1$-$C_6)$ alkyl-$(C_3$-$C_6)$ substituted cycloalkenyl, —$(C_1$-$C_6)$ alkoxy-$(C_3$-$C_6)$ cycloalkenyl, —$(C_2$-$C_6)$ alkenyl-$(C_3$-$C_6)$ cycloalkenyl, where $R_2$, $R_3$, $R_4$, $R_5$ and $R_6$ are independently selected from the group consisting of —H, -halogen, —$(C_1$-$C_6)$ alkyl, —$(C_3$-$C_6)$ cycloalkyl, —$(C_1$-$C_6)$ haloalkyl, —$(C_1$-$C_6)$ alkoxy, —$(C_1$-$C_6)$ haloalkoxy, —$(C_2$-$C_6)$ alkenyl, —$(C_2$-$C_6)$ alkynyl, -nitro, —CN, —OH, —COOH, —SH, —NH$_2$, —NH$(C_1$-$C_4)$ alkyl, and —N$((C_1$-$C_4)$ alkyl$)_2$, where $R_7$ is an atom selected from the group consisting of selenium and oxygen.

The compound of Formula I where $R_7$ is oxygen.

The compound of Formula I where $R_1$ is —$CH_2$—$CH_2$—$C_6H_5$.

The compound of Formula I where $R_6$ is —H and $R_2$ is -halogen.

The compound of Formula I is a compound of Formula I(a),

I(a)

or a pharmaceutically acceptable salt, hydrate, solvate, prodrug, stereoisomer, or tautomer thereof, where $R_1$ is -halogen, where $R_2$ and $R_3$ are independently selected from the group consisting of -halogen, —$(C_1$-$C_6)$ alkyl, —$(C_1$-$C_6)$ per halo alkyl, —$(C_3$-$C_6)$ cycloalkyl, —$(C_1$-$C_6)$ haloalkyl, —$(C_1$-$C_6)$ alkoxy, —($C_1$-$C_6$) haloalkoxy, —($C_2$-$C_6$) alkenyl, —($C_2$-$C_6$) alkynyl, -nitro, —CN, —OH, —COOH, —SH, —$NH_2$, —NH($C_1$-$C_4$) alkyl, and —N(($C_1$-$C_4$) alkyl)$_2$, where $R_4$ is an atom selected from the group consisting of selenium and oxygen.

The compound of Formula I is a compound of Formula I(b),

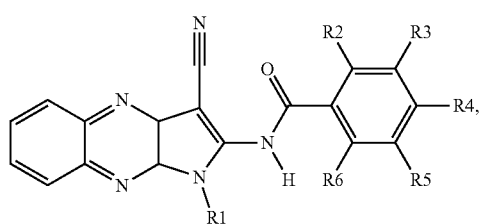

I(b)

or a pharmaceutically acceptable salt, hydrate, ester, solvate, prodrug, stereoisomer, or tautomer thereof, where $R_1$ is —$CH_2$—$C_6H_5$, —$CH_2$—$CH_2$—$C_6H_5$, —$CH_2$—$CH_2$—O—$C_6H_5$, —$CH_2$—$CH_2$—O—$C_6H_4F$, —$CH_2$—$CH_2$—O—$CH_3$, where $R_2$, $R_3$, $R_4$, $R_5$ and $R_6$ are independently selected from the group consisting of —H, -halogen, —($C_1$-$C_6$) alkyl, —($C_1$-$C_6$) per halo alkyl, —($C_3$-$C_6$) cycloalkyl, —($C_1$-$C_6$) haloalkyl, —($C_1$-$C_6$) alkoxy, —($C_1$-$C_6$) haloalkoxy, —($C_2$-$C_6$) alkenyl, —($C_2$-$C_6$) alkynyl, -nitro, —CN, —OH, —COOH, —SH, —$NH_2$, —NH($C_1$-$C_4$) alkyl, and —N(($C_1$-$C_4$) alkyl)$_2$.

The compound of Formula I is a compound of Formula I(c),

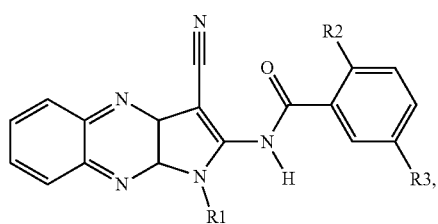

I(c)

or a pharmaceutically acceptable salt, hydrate, solvate, prodrug, stereoisomer, or tautomer thereof, where $R_1$ is —$CH_2$—$C_6H_5$, —$CH_2$—$CH_2$—$C_6H_5$, —$CH_2$—$CH_2$—O—$C_6H_5$, —$CH_2$—$CH_2$—O—$C_6H_4F$, —$CH_2$—$CH_2$—O—$CH_3$, where $R_2$ and $R_3$ are independently selected from the group consisting of —H, —$C_1$, —Br, —F and —$CH_3$.

The compound of Formula I is a compound of Formula I(d),

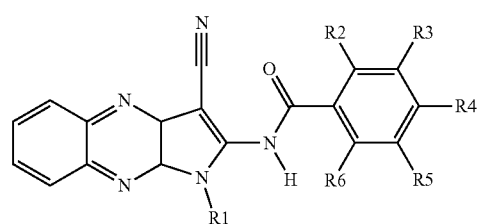

I(d)

or a pharmaceutically acceptable salt, hydrate, solvate, prodrug, stereoisomer, or tautomer thereof, where $R_1$ is —$CH_2$—$C_6H_5$, —$CH_2$—$CH_2$—$C_6H_5$, —$CH_2$—$CH_2$—O—$C_6H_5$, —$CH_2$—$CH_2$—O—$C_6H_4F$, —$CH_2$—$CH_2$—O—$CH_3$, where $R_2$, $R_3$, $R_4$, $R_5$ and $R_6$ are independently selected from the group consisting of —H, —$C_1$, —Br, —F and —$CH_3$.

The compound of Formula I is a compound of Formula I(e),

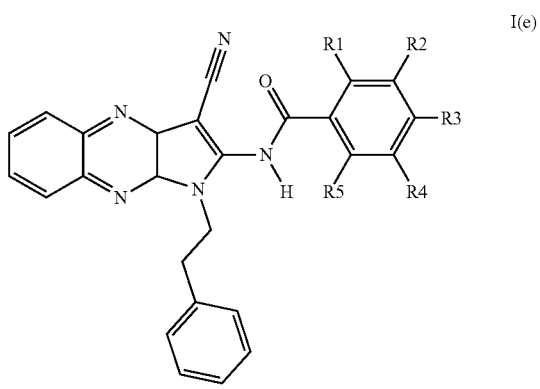

I(e)

or a pharmaceutically acceptable salt, hydrate, solvate, prodrug, stereoisomer, or tautomer thereof, where $R_1$, $R_2$, $R_3$, $R_4$ and $R_5$ are independently selected from the group consisting of —H, -halogen, —($C_1$-$C_6$) alkyl, —($C_1$-$C_6$) per halo alkyl, —($C_3$-$C_6$) cycloalkyl, —($C_1$-$C_6$) haloalkyl, —($C_1$-$C_6$) alkoxy, —($C_1$-$C_6$) haloalkoxy, —($C_2$-$C_6$) alkenyl, —($C_2$-$C_6$) alkynyl, -nitro, —CN, —OH, —COOH, —SH, —$NH_2$, —NH($C_1$-$C_4$) alkyl, and —N(($C_1$-$C_4$) alkyl)$_2$.

The compound of Formula I is a compound of Formula II,

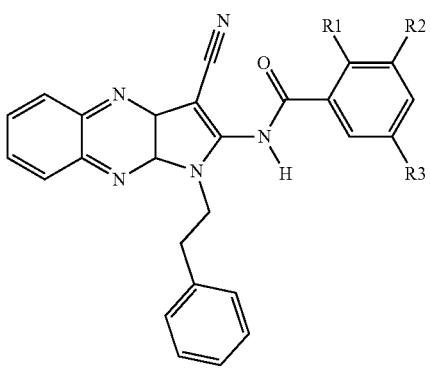

II or a pharmaceutically acceptable salt, hydrate, solvate, prodrug, stereoisomer, or tautomer thereof, where $R_1$, $R_2$ and $R_3$ are independently selected from the group consisting of —H, -halogen, —($C_1$-$C_6$) alkyl, —($C_1$-$C_6$) per halo alkyl, —($C_3$-$C_6$) cycloalkyl, —($C_1$-$C_6$) haloalkyl, —($C_1$-$C_6$) alkoxy, —($C_1$-$C_6$) haloalkoxy, —($C_2$-$C_6$) alkenyl, —($C_2$-$C_6$) alkynyl, -nitro, —CN, —OH, —COOH, —SH, —$NH_2$, —NH($C_1$-$C_4$) alkyl, and —N(($C_1$-$C_4$) alkyl)$_2$.

The compound of Formula I is a compound of Formula III,

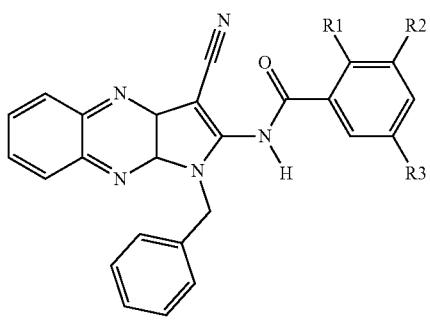

or a pharmaceutically acceptable salt, hydrate, solvate, prodrug, stereoisomer, or tautomer thereof, where $R_1$ is -halogen, where $R_2$ or $R_3$ are —H, -halogen; —H, —($C_1$-$C_6$) alkyl; and -halogen, —($C_1$-$C_6$) alkyl.

The compound of Formula III where $R_1$ is -halogen, $R_2$ is —H and $R_3$ is —($C_1$-$C_6$) alkyl.

The compound of Formula III where $R_1$ is —$C_1$, $R_2$ is —H and $R_3$ is —($C_1$-$C_6$) alkyl.

The compound of Formula III where $R_1$ is -halogen, $R_2$ is —($C_1$-$C_6$) alkyl and $R_3$ is —H.

The compound of Formula III where $R_1$ is —$C_1$, $R_2$ is —($C_1$-$C_6$) alkyl and $R_3$ is —H.

FURTHER EMBODIMENTS

Embodiments contemplated herein include Embodiments P1-P33 following.

Embodiment P1. A compound selected from the group consisting of 2-chloro-N-[3-cyano-1-(2-phenoxyethyl)-1H-pyrrolo[2,3-b]quinoxalin-2-yl]benzamide, 2-chloro-N-[3-cyano-1-(2-methoxyethyl)-1H-pyrrolo[2,3-β]quinoxalin-2-yl]benzamide, 2-chloro-N-[3-cyano-1-(2-phenylethyl)-1H-pyrrolo[2,3-β]quinoxalin-2-yl]-5-methylbenzamide, 2-chloro-N-[3-cyano-1-(2-phenylethyl)-1H-pyrrolo[2,3-b]quinoxalin-2-yl]-3-fluorobenzamide, 2-chloro-N-[3-cyano-1-(2-phenylethyl)-1H-pyrrolo[2,3-b]quinoxalin-2-yl]-6-fluorobenzamide, 2-chloro-N-{3-cyano-1-[2-(3-fluorophenyl)ethyl]-1H-pyrrolo[2,3-β]quinoxalin-2-yl}benzamide, 2,3-dichloro-N-[3-cyano-1-(2-phenylethyl)-1H-pyrrolo[2,3-β]quinoxalin-2-yl]benzamide and 2-chloro-N-[3-cyano-1-(2-phenylethyl)-1H-pyrrolo[2,3-JP]quinoxalin-2-yl]-3-methylbenzamide.

Embodiment P2. The compound of Embodiment P1, further comprising a pharmaceutically acceptable physiologically compatible excipient.

Embodiment P3. The compound of Formula I is the compound N-{1-benzyl-3-cyano-1H-pyrrolo[2,3-β]quinoxalin-2-yl}-2-chlorobenzamide for use in treating or preventing a disease.

Embodiment P4. The compound of Embodiment P3, where the compound is as an antagonist modulating signaling of a STING protein.

Embodiment P5. The compound of Embodiment P3, where the disease is selected from the group consisting of graft vs host disease, inflammation, auto inflammation, inflammation associated cancer, systemic lupus erythamatosis and Aicardi-Goutieres Syndrome.

Embodiment P6. The compound of Formula I for use in antagonising a STING protein including a therapeutically effective amount of a compound of any one of the preceding claims or a pharmaceutically acceptable salt or ester thereof, and a pharmaceutically acceptable carrier.

Embodiment P7. A method for treating a human subject with an antagonist of a STING protein, wherein the human subject is suffering from a disease, the method including the steps of determining whether a human subject has a defective functional activity of STING protein by isolating a sample from the human subject having the disease, performing a PCR assay on the sample to determine a functional activity of STING protein in a cell population; and if the human subject has an upregulated defective functional activity of STING, then identifying a selected antagonist therapy; and internally treating the human subject with the selected antagonist therapy.

Embodiment P8. The method of Embodiment P7, where the antagonist therapy is a therapeutically effective amount of the compound of Formula I.

Embodiment P9. The method of Embodiment P8, where the disease is caused by or associated with a STING protein expression.

Embodiment P9. The method of Embodiment P8, where the disease is caused by or associated with a STING protein activity.

Embodiment P9. The method of Embodiment P8, where the disease is caused by or associated with a STING protein function.

Embodiment P9. The method of Embodiment P8, where the disease is caused by or associated with upregulation of one or more STING intracellular pathways.

Embodiment P10. Use of the compound of Formula I in the manufacture of a medicament for modulating STING, for treating or preventing a disease, or for treating or preventing cancer in a subject, wherein the subject is identified as being in need of a STING antagonist for the treatment or prevention of cancer.

Embodiment P11. Use of the compound of Formula I in the manufacture of a medicament for modulating STING, for treating or preventing a disease, or for treating or preventing cancer in a subject, wherein the subject is identified as being in need of immune system downregulation for the treatment or prevention of cancer.

Embodiment P12. Use of the compound of Formula I in the manufacture of a medicament for modulating STING, for treating or preventing a disease, or for treating or preventing cancer in a subject, wherein the subject is identified as being in need of down regulating STING for the treatment or prevention of cancer.

Embodiment P13. A kit comprising instructions for determining when STING protein requires down regulation and the compound of Formula I.

Embodiment P14. The compound of Formula II for use in antagonising a STING protein including a therapeutically effective amount of a compound of any one of the preceding claims or a pharmaceutically acceptable salt or ester thereof, and a pharmaceutically acceptable carrier.

Embodiment P15. Use of the compound of Formula II in the manufacture of a medicament for modulating STING, for treating or preventing a disease, or for treating or preventing cancer in a subject, wherein the subject is identified as being in need of a STING antagonist for the treatment or prevention of cancer.

Embodiment P16. Use of the compound of Formula II in the manufacture of a medicament for modulating STING, for treating or preventing a disease, or for treating or preventing cancer in a subject, wherein the subject is identified as being in need of immune system downregulation for the treatment or prevention of cancer.

Embodiment P17. Use of the compound of Formula II in the manufacture of a medicament for modulating STING, for treating or preventing a disease, or for treating or preventing cancer in a subject, wherein the subject is identified as being in need of down regulating STING for the treatment or prevention of cancer.

Embodiment P18. A kit comprising instructions for determining when STING protein requires down regulation and the compound of Formula II.

Embodiment P19. The method of Embodiment P7, where the antagonist therapy is a therapeutically effective amount of the compound of Formula II.

Embodiment P20. The method of Embodiment P19, where the disease is caused by or associated with a STING protein expression.

Embodiment P21. The method of Embodiment P19, where the disease is caused by or associated with a STING protein activity.

Embodiment P22. The method of Embodiment P19, where the disease is caused by or associated with a STING protein function.

Embodiment P23. The method of Embodiment P19, where the disease is caused by or associated with upregulation of one or more STING intracellular pathways.

Embodiment P24. The compound of Formula III for use in antagonising a STING protein including a therapeutically effective amount of a compound of any one of the preceding claims or a pharmaceutically acceptable salt or ester thereof, and a pharmaceutically acceptable carrier.

Embodiment P25. Use of the compound of Formula III in the manufacture of a medicament for modulating STING, for treating or preventing a disease, or for treating or preventing cancer in a subject, wherein the subject is identified as being in need of a STING antagonist for the treatment or prevention of cancer.

Embodiment P26. Use of the compound of Formula III in the manufacture of a medicament for modulating STING, for treating or preventing a disease, or for treating or preventing cancer in a subject, wherein the subject is identified as being in need of immune system downregulation for the treatment or prevention of cancer.

Embodiment P27. Use of the compound of Formula III in the manufacture of a medicament for modulating STING, for treating or preventing a disease, or for treating or preventing cancer in a subject, wherein the subject is identified as being in need of down regulating STING for the treatment or prevention of cancer.

Embodiment P28. A kit comprising instructions for determining when STING protein requires down regulation and the compound of Formula III.

Embodiment P29. The method of Embodiment P7, where the antagonist therapy is a therapeutically effective amount of the compound of Formula III.

Embodiment P30. The method of Embodiment P29, where the disease is caused by or associated with a STING protein expression.

Embodiment P31. The method of Embodiment P29, where the disease is caused by or associated with a STING protein activity.

Embodiment P32. The method of Embodiment P29, where the disease is caused by or associated with a STING protein function.

Embodiment P33. The method of Embodiment P29, where the disease is caused by or associated with upregulation of one or more STING intracellular pathways.

Non-limiting illustrative compounds of the application include:

TABLE 1

| Compound | Structure | Compound Name |
| --- | --- | --- |
| Y1 | 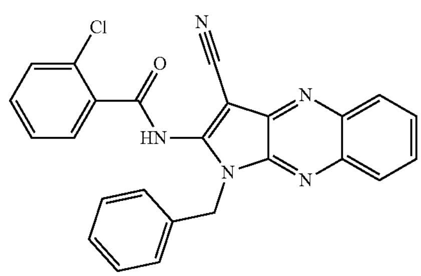 [SMILES: N#Cc1c(NC(=O)c2ccccc2Cl)n(Cc2ccccc2)c2nc3ccccc3nc12] | N-{1-benzyl-3-cyano-1H-pyrrolo[2,3-ß]quinoxalin-2-yl}-2-chlorobenzamide |
| Y2 | 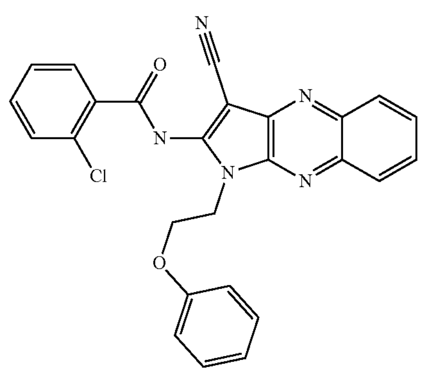 [SMILES: N#Cc1c(NC(=O)c2ccccc2Cl)n(CCOc2ccccc2)c2nc3ccccc3nc12] | 2-chloro-N-[3-cyano-1-(2-phenoxyethyl)-1H-pyrrolo[2,3-b]quinoxalin-2-yl]benzamide |

TABLE 1-continued

| Compound | Structure | Compound Name |
|---|---|---|
| Y3 | 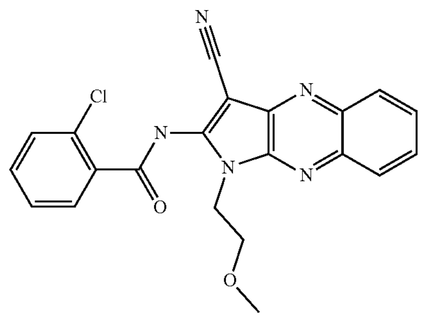 [SMILES: COCCn1c(NC(=O)c2ccccc2Cl)c(C#N)c2nc3ccccc3nc21] | 2-chloro-N-[3-cyano-1-(2-methoxyethyl)-1H-pyrrolo[2,3-ß]iquinoxalin-2-yl]benzamide |
| Y4 | 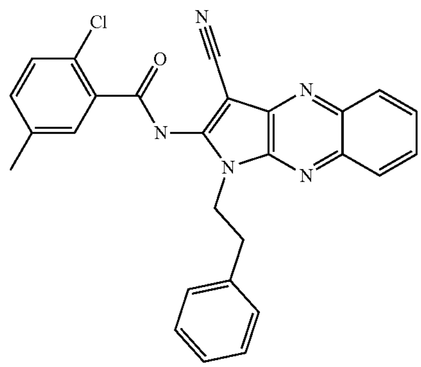 [SMILES: Cc1ccc(Cl)c(C(=O)Nc2c(C#N)c3nc4ccccc4nc3n2CCc2ccccc2)c1] | 2-chloro-N-[3-cyano-1-(2-phenylethyl)-1H-pyrrolo[2,3-b]quinoxalin-2-yl]-5-methylbenzamide |
| Y5 | 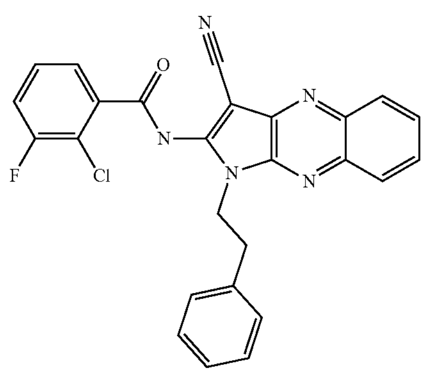 [SMILES: N#Cc1c(NC(=O)c2cccc(F)c2Cl)n(CCc2ccccc2)c2nc3ccccc3nc12] | 2-chloro-N-[3-cyano-1-(2-phenylethyl)-1H-pyrrolo[2,3-b]quinoxalin-2-yl]-3-floorobenzamide |
| Y6 | 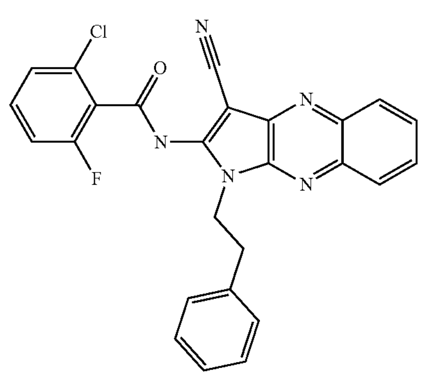 [SMILES: N#Cc1c(NC(=O)c2c(F)cccc2Cl)n(CCc2ccccc2)c2nc3ccccc3nc12] | 2-chloro-N-[3-cyano-1-(2-phenylethyl)-1H-pyrrolo[2,3-b]quinoxalin-2-yl]-6-fluorobenzamide |

TABLE 1-continued

| Compound | Structure | Compound Name |
|---|---|---|
| Y7 | 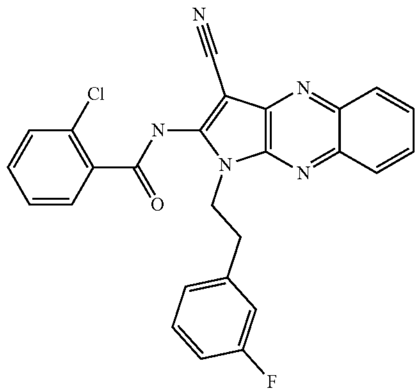 [SMILES: N#Cc1c(NC(=O)c2ccccc2Cl)n(CCc2cccc(F)c2)c2nc3ccccc3nc12] | 2-chloro-N-{3-cyano-1-[2-(3-fluorophenyl)ethyl]-1H-pyrrolo[2,3-b]quinoxalin-2-yl}benzamide |
| Y8 | 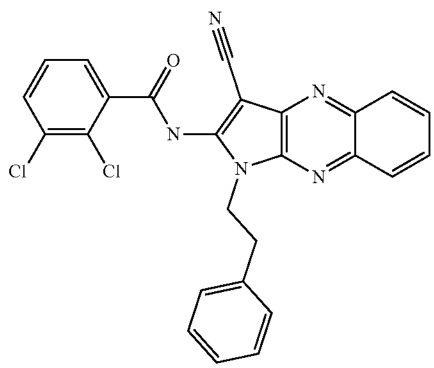 [SMILES: N#Cc1c(NC(=O)c2cccc(Cl)c2Cl)n(CCc2ccccc2)c2nc3ccccc3nc12] | 2,3-dichloro-N-[3-cyano-1-(2-phenylethyl)-1H-pyrrolo[2,3-b]quinoxalin-2-yl]benzamide |
| Y9 | 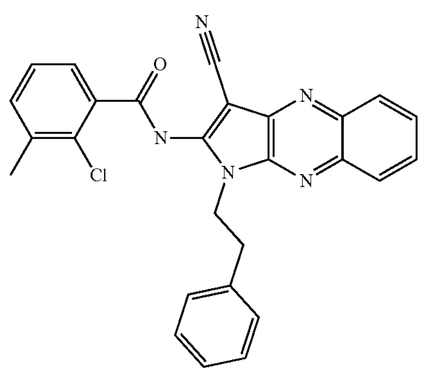 [SMILES: Cc1cccc(C(=O)Nc2c(C#N)c3nc4ccccc4nc3n2CCc2ccccc2)c1Cl] | 2-chloro-N-[3-cyano-1-(2-phenylethyl)-1H-pyrrolo[2,3-β]quinoxalin-2-yl]-3-methylbenzamide |

Some of the foregoing compounds can comprise one or more asymmetric centers, and thus can exist in various isomeric forms, e.g., stereoisomers and/or diastereomers. Accordingly, compounds of the application may be in the form of an individual enantiomer, diastereomer or geometric isomer, or may be in the form of a mixture of stereoisomers. In one embodiment, the compounds of the application are enantiopure compounds. In another embodiment, mixtures of stereoisomers or diastereomers are provided.

Another aspect is an isotopically labeled compound of any of the formulae delineated herein. Such compounds have one or more isotope atoms which may or may not be radioactive (e.g., $^3$H, $^2$H, $^{14}$C, $^{13}$C, $^{18}$F, $^{35}$S, $^{32}$P, $^{125}$I, and $^{131}$I) introduced into the compound. Such compounds are useful for drug metabolism studies and diagnostics, as well as therapeutic applications.

Potency can also be determined by $IC_{50}$ value. A compound with a lower $IC_{50}$ value, as determined under substantially similar conditions, is more potent relative to a compound with a higher $IC_{50}$ value. In some embodiments, the substantially similar conditions comprise determining the level of binding of a known STING ligand to a STING protein, in vitro or in vivo, in the presence of a compound of the application.

In one embodiment, the compounds of the present application are useful as therapeutic agents, and thus may be useful in the treatment of a disease caused by, or associated with, STING expression, activity, and/or function (e.g., deregulation of STING expression, activity, and/or function) or a disease associated with one or more of the intracellular pathways that STING is involved in (e.g. regulation of intracellular DNA-mediated type I interferon activation), such as those described herein.

A "selective STING modulator" can be identified, for example, by comparing the ability of a compound to modulate STING expression/activity/function to its ability to modulate the other proteins or a STING protein from another species. In some embodiments, the selectivity can be identified by measuring the $EC_{50}$ or $IC_{50}$ of the compounds.

The compounds of the application are defined herein by their chemical structures and/or chemical names. Where a compound is referred to by both a chemical structure and a chemical name, and the chemical structure and chemical name conflict, the chemical structure is determinative of the compound's identity.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

In another aspect, the application provides a method of synthesizing a compound disclosed herein. The synthesis of the compounds of the application can be found herein and in the Examples below. Other embodiments are a method of making a compound of any of the formulae herein using any one, or combination of, reactions delineated herein. The method can include the use of one or more intermediates or chemical reagents delineated herein.

The application also provides for a pharmaceutical composition comprising a therapeutically effective amount of a compound of the application, or a pharmaceutically acceptable salt or ester thereof, and a pharmaceutically acceptable carrier.

Another aspect of the present application relates to a kit comprising a compound of the application or a pharmaceutically acceptable salt or ester thereof, or a pharmaceutical composition of the application. In another aspect, the application provides a kit comprising a compound capable of modulating STING activity selected from one or more compounds disclosed herein, or a pharmaceutically acceptable salt or ester thereof, optionally in combination with a second agent and instructions for use.

Another aspect of the present application relates to a compound of the application or a pharmaceutically acceptable salt or ester thereof, or a pharmaceutical composition of the application, for use in the manufacture of a medicament for modulating (e.g., inhibiting or stimulating) a STING protein, for treating or preventing a disease, wherein the diseases is caused by, or associated with, STING expression, activity, and/or function (e.g., deregulation of STING expression, activity, and/or function), or for treating or preventing a disease associated with deregulation of one or more of the intracellular pathways in which a STING protein is involved (e.g., deregulation of intracellular dsDNA mediated type I interferon activation).

Another aspect of the present application relates to use of a compound of the application or a pharmaceutically acceptable salt or ester thereof, or a pharmaceutical composition of the application, in the manufacture of a medicament for modulating (e.g., inhibiting or stimulating) a STING protein, for treating or preventing a disease, wherein the diseases is caused by, or associated with, STING expression, activity, and/or function (e.g., deregulation of STING expression, activity, and/or function), or for treating or preventing a disease associated with deregulation of one or more of the intracellular pathways in which a STING protein is involved (e.g., deregulation of intracellular dsDNA mediated type I interferon activation).

Another aspect of the present application relates to a compound of the application or a pharmaceutically acceptable salt or ester thereof, or a pharmaceutical composition of the application, for use in modulating (e.g., inhibiting or stimulating) a STING protein, in treating or preventing a disease, wherein the diseases is caused by, or associated with, STING expression, activity, and/or function (e.g., deregulation of STING expression, activity, and/or function), or in treating or preventing a disease associated with deregulation of one or more of the intracellular pathways in which a STING protein is involved (e.g., deregulation of intracellular dsDNA mediated type I interferon activation).

Another aspect of the present application relates to use of a compound of the application or a pharmaceutically acceptable salt or ester thereof, or a pharmaceutical composition of the application, in antagonizing a STING protein, in treating or preventing a disease, wherein the diseases is caused by, or associated with, STING expression, activity, and/or function (e.g., deregulation of STING expression, activity, and/or function), or in treating or preventing a disease associated with deregulation of one or more of the intracellular pathways in which a STING protein is involved (e.g., deregulation of intracellular dsDNA mediated type I interferon activation).

Method of Synthesizing the Compounds

Compounds of the present application can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, $5^{th}$ edition, John Wiley & Sons: New York, 2001; and Greene, T. W., Wuts, P. G. M., *Protective Groups in Organic Synthesis*, $3^{rd}$ edition, John Wiley & Sons: New York, 1999 are useful and recognized reference textbooks of organic synthesis known to those in the art. The following descriptions of synthetic methods are designed to illustrate, but not to limit, general procedures for the preparation of compounds of the present application. The processes generally provide the desired final compound at or near the end of the overall process, although it may be desirable in certain instances to further convert the compound to a pharmaceutically acceptable salt, ester, or prodrug thereof. Suitable synthetic routes are depicted in the schemes below.

Example 15: Identification of Antagonists

Purified STING protein was used as bait to identify binding compounds, using a thermal shift assay (TSA). A library containing 250,000 compounds (Enamine, Monmouth Jct., NJ) was surveyed. Compounds that bound to STING were then examined for their ability to inhibit STING signaling, see Examples 1-4 vide infra. In the presence of cytosolic DNA species, STING becomes activated to drive the transcription of cytokines such as type I IFN. Compounds binding to STING via TSA were subsequently examined for their ability prevent cytosolic DNA species from activating the type I interferon (IFN) promoter, using a live cell assay. This assay comprised immortalized human fibroblasts (hTERT) that were stably transfected with the type I IFN promoter driving luciferase as well as the CMV promoter driving SEAP (hTERT-pIFNβ-Glu). The ability of the small molecules to prevent activation of the type I IFN promoter and the transcription of luciferase, but not SEAP in response to cytosolic DNA species can be assessed. The activation of STING, typically by CDNs, in turn activates the transcription factors NF-κB and IRF3, both of which are required to induce the transcriptional stimulation of the Type I IFN promoter, but not the CMV promoter (IRF3 and NF-kB transcription factor binding sites are not contained in the CMV promoter). Inhibition of STING activation by a small molecule identified in the first screen (HTS), and a decrease in the level of luciferase in response to transfection of cytosolic DNA can be surveyed.

As used herein the phrase "STING intracellular pathways" include IRF-3 and NF-kB pathways.

The compounds of the present application can be prepared in a number of ways well known to those skilled in the art of organic synthesis. By way of example, compounds of the present application can be synthesized using the methods described below, together with synthetic methods known in the art of synthetic organic chemistry, or variations thereon as appreciated by those skilled in the art. Preferred methods include but are not limited to those methods described below.

Compounds of the present application can be synthesized by following the steps outlined in the following Schemes, which comprise different sequences of assembling intermediates. Starting materials are either commercially available or made by known procedures in the reported literature or as illustrated.

A compound of the application can be prepared as a pharmaceutically acceptable acid addition salt by reacting the free base form of the compound with a pharmaceutically acceptable inorganic or organic acid. Alternatively, a pharmaceutically acceptable base addition salt of a compound of the application can be prepared by reacting the free acid form of the compound with a pharmaceutically acceptable inorganic or organic base. The pharmaceutically acceptable salt may include various counterions, e.g., counterions of the inorganic or organic acid, counterions of the inorganic or organic base, or counterions afforded by counterion exchange.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alternatively, the salt forms of the compounds of the application can be prepared using salts of the starting materials or intermediates. The free acid or free base forms of the compounds of the application can be prepared from the corresponding base addition salt or acid addition salt from, respectively. For example, a compound of the application in an acid addition salt form can be converted to the corresponding free base by treating with a suitable base (e.g., ammonium hydroxide solution, sodium hydroxide, and the like). A compound of the application in a base addition salt form can be converted to the corresponding free acid by treating with a suitable acid (e.g., hydrochloric acid, etc.).

Those skilled in the art will recognize if a stereo center exists in the compounds disclosed herein. Accordingly, the present application includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

Compounds of the present application that contain non pyrrolo quinoxaline nitrogens can be converted to N-oxides by treatment with an oxidizing agent (e.g., 3-chloroperoxybenzoic acid (m-CPBA) and/or hydrogen peroxides) to afford other compounds of the present application. Thus, all shown and claimed non pyrrolo quinoxaline nitrogen-containing compounds are considered, when allowed by valency and structure, to include both the compound as shown and its N-oxide derivative (which can be designated as N→O or N$^+$—O—). Furthermore, in other instances, the nitrogens in the non pyrrolo quinoxaline compounds of the present application can be converted to N-hydroxy or N-alkoxy compounds. For example, N-hydroxy compounds can be prepared by oxidation of the parent amine by an oxidizing agent such as m-CPBA. All shown and claimed non pyrrolo quinoxaline nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

Prodrugs of the compounds of the application can be prepared by methods known to those of ordinary skill in the art (e.g., for further details see Saulnier et al., (1994), Bioorganic and Medicinal Chemistry Letters, Vol. 4, p. 1985, which is herein expressly incorporated by reference in its entirety and for all purposes). For example, appropriate prodrugs can be prepared by reacting a non-derivatized compound of the application with a suitable carbamylating agent (e.g., 1,1-acyloxyalkylcarbanochloridate, para-nitrophenyl carbonate, or the like). Specifically, the central N-acetic acid moiety, and other analogous carboxylic acid groups, of the compounds of the present invention can be modified through techniques known in the art to produce effective prodrugs of the present invention.

Protected derivatives of the compounds of the application can be made by means known to those of ordinary skill in the art. A detailed description of techniques applicable to the creation of protecting groups and their removal can be found in T. W. Greene, "Protecting Groups in Organic Chemistry", 3rd edition, John Wiley and Sons, Inc., 1999, which is herein expressly incorporated by reference in its entirety and for all purposes.

Compounds of the present application can be conveniently prepared, or formed during the process of the application, as solvates (e.g., hydrates). Hydrates of compounds of the present application can be conveniently prepared by recrystallization from an aqueous/organic solvent mixture, using organic solvents such as dioxin, tetrahydrofuran or methanol.

Optical isomers may be prepared from their respective optically active precursors by the procedures described herein, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers, Racemates, and Resolutions (John Wiley & Sons, 1981), which is herein expressly incorporated by reference in its entirety and for all purposes The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present application. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), which are herein expressly incorporated by reference in their entireties and for all purposes, and subsequent editions thereof.

The compounds of this application may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Biological Assays

Biological activities of the compounds of the present application can be measured by various biochemical or cellular assays known to one of ordinary skill in the art. Non-limiting examples of biochemical and cellular assays are listed in the Examples vide infra.

Pharmaceutical Compositions

In another aspect, a pharmaceutical composition is provided. The pharmaceutical composition comprises a therapeutically effective amount of a compound of the application, or a pharmaceutically acceptable salt or ester thereof, and a pharmaceutically acceptable carrier.

Compounds of the application may be administered as pharmaceutical compositions by any conventional route, in particular internally, e.g., orally, e.g., in the form of tablets or capsules, or parenterally, e.g., in the form of injectable solutions or suspensions, or topically, e.g., in the form of lotions, gels, ointments or creams, or in a nasal or suppository form.

Pharmaceutical compositions including a compound of the present application in free form or in a pharmaceutically acceptable salt form in association with at least one pharmaceutically acceptable carrier or diluent may be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present application with a carrier. A carrier may include absorbable pharmacologically acceptable solvents to assist passage through the skin of the host. For example, transdermal devices may be in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

The pharmaceutical compositions of the present application comprise a therapeutically effective amount of a compound of the present application formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which may serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylenepolyoxy propylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes, oils such as peanut oil, cottonseed oil; safflower oil; sesame oil; olive oil; corn oil and soybean oil; glycols such a propylene glycol or polyethylene glycol; esters such as ethyl oleate and ethyl laurate, agar; buffering agents such as magnesium hydroxide and aluminum hydroxide; alginic acid; pyrogen-free water, isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this application may be administered to humans and other animals orally, rectally, parenterally, intracisternally, intravaginally, intraperitoneally, topically (as by powders, ointments, or drops), buccally, or as an oral or nasal spray.

Liquid dosage forms for oral administration may include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous, or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing the compounds of this application with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard filled gelatin capsules using such excipients as lactose or milk sugar as well as high molecular weight polyethylene glycols and the like.

The active compounds may also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this application include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this application.

The ointments, pastes, creams and gels may contain, in addition to an active compound of this application, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this application, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this application include powders, sprays, ointments, pastes, creams, lotions, gels, solutions, patches and inhalants. In one embodiment, the active compound is mixed under sterile conditions with a pharmaceutically acceptable carrier, and with any preservatives, buffers or propellants that are required.

The pharmaceutical compositions containing active compounds of the present application may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Techniques for formulation and administration of the disclosed compounds of the application can be found in *Remington: the Science and Practice of Pharmacy*, 19$^{th}$ edition, Mack Publishing Co., Easton, PA (1995), which is herein expressly incorporated by reference in its entirety and for all purposes. In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

Methods of Use

In one aspect, the present application provides a method of inhibiting a STING protein. The method comprises administering to a subject in need thereof an effective amount of a compound of the application or a pharmaceutically acceptable salt or ester thereof, or a pharmaceutical composition of the application.

In some embodiments, the modulation of a STING protein activity is measured by $IC_{50}$. In some embodiments, the modulation of a STING protein activity is measured by $EC_{50}$.

A compound of the present application (e.g., a compound of any of the formulae described herein, or selected from any compounds described herein) is capable of treating or preventing a disease, wherein the diseases is caused by, or associated with, STING expression, activity, and/or function (e.g., deregulation of STING expression, activity, and/or function) or a disease associated with deregulation of one or more of the intracellular pathways in which a STING protein is involved (e.g., deregulation of intracellular dsDNA mediated type I interferon activation).

In one aspect, the present application provides a method of treating or preventing a disease, wherein the diseases is caused by, or associated with, STING expression, activity, and/or function (e.g., deregulation of STING expression, activity, and/or function). The method comprises administering to a subject in need thereof an effective amount of a STING antagonist compound of the application or a pharmaceutically acceptable salt or ester thereof, or a pharmaceutical composition of the application. In one aspect, the disease is a STING mediated disorder.

In one aspect, the present application provides a method of treating or preventing a disease associated with deregulation of one or more of the intracellular pathways in which a STING protein is involved (e.g., deregulation of intracellular dsDNA mediated type I interferon activation). The method comprises administering to a subject in need thereof an effective amount of a STING antagonist compound of the application or a pharmaceutically acceptable salt or ester thereof, or a pharmaceutical composition of the application.

In one embodiment, the present application provides a method of treating or preventing any of the diseases, disorders, and conditions described herein, wherein the subject is a human. In one embodiment, the application provides a method of treating. In one embodiment, the application provides a method of preventing.

As antagonists of a STING protein, the compounds and compositions of this application are particularly useful for treating or lessening the severity of a disease, condition, or disorder where a STING protein or one or more of the intracellular pathways that STING is involved is implicated in the disease, condition, or disorder. In one embodiment, the present application provides a method for treating or lessening the severity of a disease, condition, or disorder with STING antagonist compounds that modulate binding of a cyclic di-nucleotide, (CDN) including non-canonical cyclic di-nucleotide, such as 2'3'cGAMP, to a STING protein. In one embodiment, the present application provides a method for treating or lessening the severity of a disease, condition, or disorder with compounds that modulate the synthesis of type I interferon and/or type I IFN response and other cytokines, chemokines (STING-inducible proteins).

In one aspect, the present application also provides a method of treating or preventing cell proliferative disorders such as hyperplasias, dysplasias, or pre-cancerous lesions. Dysplasia is the earliest form of pre-cancerous lesion recognizable in a biopsy by a pathologist. The compounds of the present application may be administered for the purpose of preventing hyperplasias, dysplasias, or pre-cancerous lesions from continuing to expand or from becoming cancerous. Examples of pre-cancerous lesions may occur in skin, esophageal tissue, breast, and cervical intra-epithelial tissue.

In one embodiment, the disease or disorder includes, but is not limited to, immune disorders, autoimmunity, a cell proliferative disease or disorder, cancer, inflammation, graft vs host, transplantation, gastrointestinal disorder, rheumatoid arthritis, systemic lupus, cachexia, neurodegenerative disease or disorders, neurological diseases or disorders, cardiac dysfunction, or microbial infection (e.g., viral, bacterial, and/or fungi infection, parasitic, or infection caused by other microorganism).

In one embodiment, the disease or disorder is a cell proliferative disease or disorder.

As used herein, the term "cell proliferative disorder" refers to conditions in which unregulated or abnormal growth, or both, of cells can lead to the development of an unwanted condition or disease, which may or may not be cancerous. Exemplary cell proliferative diseases or disorders encompass a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue. A cell proliferative disease or disorder includes a precancer or a precancerous condition. A cell proliferative disease or disorder includes cancer.

In one embodiment, the proliferative disease or disorder is a non-cancerous. In one embodiment, the non-cancerous disease or disorder includes, but is not limited to, rheumatoid arthritis; inflammation; autoimmune disease; lymphoproliferative conditions; acromegaly; rheumatoid spondylitis; osteoarthritis; gout; other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; skin-related hyperproliferative disorders; psoriasis; eczema; atopic dermatitis; hyperpigmentation disorders; eye-related hyperproliferative disorders; age-related macular degeneration; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis; graft-versus-host reaction; fibroadipose hyperplasia; spinocerebellar ataxia type 1; CLOVES syndrome; Harlequin ichthyosis; macrodactyly syndrome; Proteus syndrome (Wiedemann syndrome); LEOPARD syndrome; systemic sclerosis; Multiple Sclerosis; lupus; fibromyalgia; AIDS and other viral diseases such as Herpes Zoster, Herpes Simplex I or II, influenza virus and cytomegalovirus; diabetes mellitus; hemihyperplasia-multiple lipomatosis syndrome; megalencephaly; rare hypoglycemia, Klippel-Trenaunay syndrome; harmatoma; Cowden syndrome; or overgrowth-hyperglycemia.

In one embodiment, the proliferative disease or disorder is cancer. In one embodiment, the cancer is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors.

The term "cancer" includes, but is not limited to, the following cancers: breast; ovary; cervix; prostate; testis, genitourinary tract; esophagus; larynx, glioblastoma; neuroblastoma; stomach; skin, keratoacanthoma; lung, epidermoid carcinoma, large cell carcinoma, small cell carcinoma, lung adenocarcinoma; bone; colon; colorectal; adenoma; pancreas, adenocarcinoma; thyroid, follicular carcinoma, undifferentiated carcinoma, papillary carcinoma; seminoma; melanoma; sarcoma; bladder carcinoma; liver carcinoma and biliary passages; kidney carcinoma; myeloid disorders; lymphoid disorders, Hodgkin's, hairy cells; buccal cavity and pharynx (oral), lip, tongue, mouth, pharynx; small intestine; colon, rectum, large intestine, rectum, brain and central nervous system; chronic myeloid leukemia (CML), and leukemia. The term "cancer" includes, but is not limited to, the following cancers: myeloma, lymphoma, or a cancer selected from gastric, renal, or and the following cancers: head and neck, oropharangeal, non-small cell lung cancer (NSCLC), endometrial, hepatocarcinoma, Non-Hodgkins lymphoma, and pulmonary.

The term "cancer" also refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute non-lymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, nasopharyngeal and esophageal), genitourinary cancers (e.g., prostate, bladder, renal, uterine, ovarian, testicular), lung cancer (e.g., small-cell and non-small cell), breast cancer, pancreatic cancer, melanoma and other skin cancers, stomach cancer, brain tumors, tumors related to Gorlin's syndrome (e.g., medulloblastoma, meningioma, etc.), and liver cancer. Additional exemplary forms of cancer which may be treated by the subject compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Cancer may also include colon carcinoma, familial adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma.

Cancer may also include colorectal, thyroid, breast, and lung cancer; and myeloproliferative disorders, such as polycythemia vera, thrombocythemia, myeloid metaplasia with myelofibrosis, chronic myelogenous leukemia, chronic myelomonocytic leukemia, hypereosinophilic syndrome, juvenile myelomonocytic leukemia, and systemic mast cell disease. In one embodiment, the compounds of this application are useful for treating hematopoietic disorders, in particular, acute-myelogenous leukemia (AML), chronic-myelogenous leukemia (CML), acute-promyelocytic leukemia, and acute lymphocytic leukemia (ALL).

Exemplary cancers may also include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, uringary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, Merkel cell carcinoma, mesothelioma malignant, mesothelioma, metastatic squamous neck cancer, mouth cancer, cancer of the tongue, multiple endocrine neoplasia syndrome, Mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, Ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

A "cell proliferative disorder of the hematologic system" is a cell proliferative disease or disorder involving cells of the hematologic system. A cell proliferative disorder of the hematologic system can include lymphoma, leukemia, myeloid neoplasms, mast cell neoplasms, myelodysplasia, benign monoclonal gammopathy, lymphomatoid granulomatosis, lymphomatoid papulosis, polycythemia vera, chronic myelocytic leukemia, agnogenic myeloid metaplasia, and essential thrombocythemia. A cell proliferative disorder of the hematologic system can include hyperplasia, dysplasia, and metaplasia of cells of the hematologic system. Compounds and compositions of the present application may be used to treat a cancer selected from the group consisting of a hematologic cancer or a hematologic cell proliferative disorder. A hematologic cancer can include multiple myeloma, lymphoma (including Hodgkin's lymphoma, non-Hodgkin's lymphoma, childhood lymphomas, and lymphomas of lymphocytic and cutaneous origin), leukemia (including childhood leukemia, hairy-cell leukemia, acute lymphocytic leukemia, acute myelocytic leukemia, chronic lymphocytic leukemia, chronic myelocytic leukemia, chronic myelogenous leukemia, and mast cell leukemia), myeloid neoplasms, and mast cell neoplasms.

A "cell proliferative disorder of the lung" is a cell proliferative disease or disorder involving cells of the lung. Cell proliferative disorders of the lung can include all forms of cell proliferative disorders affecting lung cells. Cell proliferative disorders of the lung can include lung cancer, a precancer or precancerous condition of the lung, benign growths or lesions of the lung, and malignant growths or lesions of the lung, and metastatic lesions in tissue and organs in the body other than the lung. Compounds and compositions of the present application may be used to treat lung cancer or cell proliferative disorders of the lung. Lung cancer can include all forms of cancer of the lung. Lung cancer can include malignant lung neoplasms, carcinoma in situ, typical carcinoid tumors, and atypical carcinoid tumors. Lung cancer can include small cell lung cancer ("SCLC"), non-small cell lung cancer ("NSCLC"), squamous cell carcinoma, adenocarcinoma, small cell carcinoma, large cell carcinoma, adenosquamous cell carcinoma, and mesothelioma. Lung cancer can include "scar carcinoma", bronchioalveolar carcinoma, giant cell carcinoma, spindle cell carcinoma, and large cell neuroendocrine carcinoma. Lung cancer can include lung neoplasms having histologic and ultrastructual heterogeneity (e.g., mixed cell types).

Cell proliferative disorders of the lung can also include hyperplasia, metaplasia, and dysplasia of the lung. Cell proliferative disorders of the lung can include asbestos-induced hyperplasia, squamous metaplasia, and benign reactive mesothelial metaplasia. Cell proliferative disorders of the lung can include replacement of columnar epithelium with stratified squamous epithelium, and mucosal dysplasia. Individuals exposed to inhaled injurious environmental agents such as cigarette smoke and asbestos may be at increased risk for developing cell proliferative disorders of the lung. Prior lung diseases that may predispose individuals to development of cell proliferative disorders of the lung can include chronic interstitial lung disease, necrotizing pulmonary disease, scleroderma, rheumatoid disease, sarcoidosis, interstitial pneumonitis, tuberculosis, repeated pneumonias, idiopathic pulmonary fibrosis, granulomata, asbestosis, fibrosing alveolitis, and Hodgkin's disease.

A "cell proliferative disorder of the colon" is a cell proliferative disorder involving cells of the colon. A cell proliferative disorder of the colon includes colon cancer. Compounds and compositions of the present application may be used to treat colon cancer or cell proliferative disorders of the colon. Colon cancer can include all forms of cancer of the colon. Colon cancer can include sporadic and hereditary colon cancers. Colon cancer can include malignant colon neoplasms, carcinoma in situ, typical carcinoid tumors, and atypical carcinoid tumors. Colon cancer can include adenocarcinoma, squamous cell carcinoma, and adenosquamous cell carcinoma. Colon cancer can be associated with a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis. Colon cancer can be caused by a hereditary syndrome selected from the group consisting of hereditary nonpolyposis colorectal cancer, familial adenomatous polyposis, Gardner's syndrome, Peutz-Jeghers syndrome, Turcot's syndrome, and juvenile polyposis.

Cell proliferative disorders of the colon can also include colon cancer, precancerous conditions of the colon, adenomatous polyps of the colon and metachronous lesions of the colon. A cell proliferative disorder of the colon can include adenoma. Cell proliferative disorders of the colon can be characterized by hyperplasia, metaplasia, and dysplasia of the colon. Prior colon diseases that may predispose individuals to development of cell proliferative disorders of the colon can include prior colon cancer. Current disease that may predispose individuals to development of cell proliferative disorders of the colon can include Crohn's disease and ulcerative colitis. A cell proliferative disorder of the colon can be associated with a mutation in a gene selected from the group consisting of p53, ras, FAP and DCC. An individual can have an elevated risk of developing a cell proliferative disorder of the colon due to the presence of a mutation in a gene selected from the group consisting of p53, ras, FAP and DCC.

A "cell proliferative disorder of the pancreas" is a cell proliferative disorder involving cells of the pancreas. Compounds and compositions of the present application may be used to treat pancreatic cancer or cell proliferative disorders of the pancreas. Cell proliferative disorders of the pancreas can include all forms of cell proliferative disorders affecting pancreatic cells. Cell proliferative disorders of the pancreas can include pancreas cancer, a precancer or precancerous condition of the pancreas, hyperplasia of the pancreas, and dysplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas. Pancreatic cancer can include ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma. Pancreatic cancer can also include pancreatic neoplasms having histologic and ultrastructual heterogeneity (e.g., mixed cell types).

A "cell proliferative disorder of the prostate" is a cell proliferative disorder involving cells of the prostate. Compounds and compositions of the present application may be used to treat prostate cancer or cell proliferative disorders of the prostate. Cell proliferative disorders of the prostate can include all forms of cell proliferative disorders affecting prostate cells. Cell proliferative disorders of the prostate can include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate can include hyperplasia, metaplasia, and dysplasia of the prostate.

A "cell proliferative disorder of the skin" is a cell proliferative disorder involving cells of the skin. Compounds and compositions of the present application may be used to treat skin cancer or cell proliferative disorders of the skin. Cell proliferative disorders of the skin can include all forms of cell proliferative disorders affecting skin cells. Cell proliferative disorders of the skin can include a precancer or precancerous condition of the skin, benign growths or lesions of the skin, melanoma, malignant melanoma and other malignant growths or lesions of the skin, and metastatic lesions in tissue and organs in the body other than the skin. Cell proliferative disorders of the skin can include hyperplasia, metaplasia, and dysplasia of the skin.

A "cell proliferative disorder of the ovary" is a cell proliferative disorder involving cells of the ovary. Compounds and compositions of the present application may be used to treat ovarian cancer or cell proliferative disorders of the ovary. Cell proliferative disorders of the ovary can include all forms of cell proliferative disorders affecting cells of the ovary. Cell proliferative disorders of the ovary can include a precancer or precancerous condition of the ovary, benign growths or lesions of the ovary, ovarian cancer, malignant growths or lesions of the ovary, and metastatic lesions in tissue and organs in the body other than the ovary. Cell proliferative disorders of the skin can include hyperplasia, metaplasia, and dysplasia of cells of the ovary.

A "cell proliferative disorder of the breast" is a cell proliferative disorder involving cells of the breast. Compounds and compositions of the present application may be used to treat breast cancer or cell proliferative disorders of the breast. Cell proliferative disorders of the breast can include all forms of cell proliferative disorders affecting breast cells. Cell proliferative disorders of the breast can include breast cancer, a precancer or precancerous condition of the breast, benign growths or lesions of the breast, and malignant growths or lesions of the breast, and metastatic lesions in tissue and organs in the body other than the breast. Cell proliferative disorders of the breast can include hyperplasia, metaplasia, and dysplasia of the breast.

In one embodiment, the disease or disorder includes, but is not limited to, a disease or disorders caused by or associated with *Entamoeba histolytica, Pneumocystis carinii, Trypanosoma cruzi, Trypanosoma brucei, Leishmania mexicana, Clostridium histolyticum, Staphylococcus aureus*, foot-and-mouth disease virus, or *Crithidia fasciculata*, as well as disease or disorder associated with osteoporosis, autoimmunity, schistosomiasis, malaria, tumor metastasis, metachromatic leukodystrophy, muscular dystrophy, or amytrophy.

Additional examples of the diseases or disorders include, but are not limited to, diseases or disorders caused by or associated with veterinary and human pathogenic protozoa, intracellular active parasites of the phylum Apicomplexa or Sarcomastigophora, *Trypanosoma, Plasmodia, Leishmania, Babesia* and *Theileria*, Cryptosporidia, Sacrocystida, Amoeba, Coccidia, and Trichomonadia. For example, the diseases or disorders include, but are not limited to, *Malaria tropica*, caused by, for example, *Plasmodium falciparum*; *Malaria tertiana*, caused by *Plasmodium vivax* or *Plasmodium ovale*, *Malaria quartana*, caused by *Plasmodium malariae*; Toxoplasmosis, caused by *Toxoplasma gondii*; Coccidiosis, caused for instance by *Isospora belli*; intestinal Sarcosporidiosis, caused by *Sarcocystis suihominis*; dysentery caused by *Entamoeba histolytica*; Cryptosporidiosis, caused by *Cryptosporidium parvum*; Chagas' disease, caused by *Trypanosoma cruzi*; sleeping sickness, caused by *Trypanosoma brucei rhodesiense or gambiense, the cutaneous and visceral as well as other forms of Leishmaniosis; diseases or disorders caused by veterinary pathogenic protozoa, such as Theileria parva*, the pathogen causing bovine East coast fever, *Trypanosoma congolense congolense* or *Trypanosoma vivax vivax*, *Trypanosoma brucei brucei*, pathogens causing Nagana cattle disease in Africa, *Trypanosoma brucei evansi* causing Surra, *Babesia bigemina*, the pathogen causing Texas fever in cattle and buffalos, *Babesia bovis*, the pathogen causing European bovine Babesiosis as well as Babesiosis in dogs, cats and sheep, *Sarcocystis ovicanis* and *ovifelis* pathogens causing Sarcocystiosis in sheep, cattle and pigs, Cryptosporidia, pathogens causing Cryptosporidioses in cattle and birds, *Eimeria* and *Isospora* species, pathogens causing Coccidiosis in rabbits, cattle, sheep, goats, pigs and birds, especially in chickens and turkeys. *Rickettsia* comprise species such as *Rickettsia felis*, *Rickettsia prowazekii*, *Rickettsia rickettsii*, *Rickettsia typhi*, *Rickettsia conorii*, *Rickettsia africae* and cause diseases such as typhus, rickettsialpox, Boutonneuse fever, African Tick Bite Fever, Rocky Mountain spotted fever, Australian Tick Typhus, Flinders Island Spotted Fever and Queensland Tick Typhus.

In one embodiment, the disease or disorder is caused by, or associated with, one or more bacteria. Examples of the bacteria include, but are not limited to, the Gram positive organisms (e.g., *Staphylococcus aureus, Staphylococcus epidermidis, Enterococcus faecalis* and *E. faecium, Streptococcus pneumoniae*) and the Gram negative organisms (e.g., *Pseudomonas aeruginosa, Burkholdia cepacia, Xanthomonas maltophila, Escherichia coli, Enterobacter* spp, *Klebsiella pneumoniae* and *Salmonella* spp).

In one embodiment, the disease or disorder is caused by, or associated with, one or more fungi. Examples of the fungi include, but are not limited to, *Candida albicans, Histoplasma neoformans, Coccidioides immitis*, and *Penicillium marneffei*.

In one embodiment, the disease or disorder is a neurological disease or disorder. In one embodiment, the neurological disease or disorder involves the central nervous system (e.g., brain, brainstem and cerebellum), the peripheral nervous system (e.g., cranial nerves), and/or the autonomic nervous system (e.g., parts of which are located in both central and peripheral nervous system).

Examples of the neurological disorders include, but are not limited to, acquired epileptiform aphasia; acute disseminated encephalomyelitis; adrenoleukodystrophy; age-related macular degeneration; agenesis of the corpus callosum; agnosia; Aicardi syndrome; Alexander disease; Alpers' disease; alternating hemiplegia; Alzheimer's disease; Vascular dementia; amyotrophic lateral sclerosis; anencephaly; Angelman syndrome; angiomatosis; anoxia; aphasia; apraxia; arachnoid cysts; arachnoiditis; Anronl-Chiari malformation; arteriovenous malformation; Asperger syndrome; ataxia telegiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal tumor; Brown-Sequard syndrome; Canavan disease; carpal tunnel syndrome; causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy; chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease; cytomegalovirus infection; dancing eyes-dancing feet syndrome; Dandy-Walker syndrome; Dawson disease; De Morsier's syndrome; Dejerine-Klumke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor, Fabry's disease; Fahr's syndrome; fainting; familial spastic paralysis; febrile seizures; Fisher syndrome; Friedreich's ataxia; fronto-temporal dementia and other "tauopathies"; Gaucher's disease; Gerstmann's syndrome; giant cell arteritis; giant cell inclusion disease; globoid cell leukodystrophy; Guillain-Barre syndrome; HTLV-1-associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile phytanic acid storage disease; infantile refsum disease; infantile spasms; inflammatory myopathy; intracranial cyst; intracranial hypertension; Joubert syndrome; Kearns-Sayre syndrome; Kennedy disease Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gustaut syndrome; Lesch-Nyhan syndrome; leukodystrophy; Lewy body dementia; Lissencephaly; locked-in syndrome; Lou Gehrig's disease (i.e., motor neuron disease or amyotrophic lateral sclerosis); lumbar disc disease; Lyme disease—neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neuron disease; Moyamoya disease; mucopolysaccharidoses; multi-infarct dementia; multifocal motor neuropathy; multiple sclerosis and other demyelinating disorders; multiple system atrophy with postural hypotension; p muscular dystrophy; myasthenia gravis; myeloclonic diffuse sclerosis; myoclonic encephalopathy of infants;

myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenital; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; post-polio syndrome; postherpetic neuralgia; postinfectious encephalomyelitis; postural hypotension; Prader-Willi syndrome; primary lateral sclerosis; prion diseases; progressive hemifacial atrophy; progressive multifocal leukoencephalopathy; progressive sclerosing poliodystrophy; progressive supranuclear palsy; pseudotumor cerebri; Ramsay-Hunt syndrome (types I and II); Rasmussen's encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus dance; Sandhoff disease; Schilder's disease; schizencephaly; septo-optic dysplasia; shaken baby syndrome; shingles; Shy-Drager syndrome; Sjögren's syndrome; sleep apnea; Soto's syndrome; spasticity; spina bifida; spinal cord injury; spinal cord tumors; spinal muscular atrophy; Stiff-Person syndrome; stroke; Sturge-Weber syndrome; subacute sclerosing panencephalitis; subcortical arteriosclerotic encephalopathy; Sydenham chorea; syncope; syringomyelia; tardive dyskinesia; Tay-Sachs disease; temporal arteritis; tethered spinal cord syndrome; Thomsen disease; thoracic outlet syndrome; Tic Douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau disease; Wallenberg's syndrome; Werdnig-Hoffman disease; West syndrome; whiplash; Williams syndrome; Wildon's disease; and Zellweger syndrome.

Examples of neurodegenerative diseases may also include, without limitation, Adrenoleukodystrophy (ALD), Alexander's disease, Alper's disease, Alzheimer's disease, Amyotrophic lateral sclerosis (Lou Gehrig's Disease), Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, Familial fatal insomnia, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy, Niemann Pick disease, Parkinson's disease, Pelizaeus-Merzbacher Disease, Pick's disease, Primary lateral sclerosis, Prion diseases, Progressive Supranuclear Palsy, Refsum's disease, Sandhoff disease, Schilder's disease, Subacute combined degeneration of spinal cord secondary to Pernicious Anaemia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, Tabes *dorsalis*, and Toxic encephalopathy.

In one embodiment, the disease or disorder is an autoimmune disease. Examples of autoimmune diseases include, but are not limited to, rheumatoid arthritis, systemic lupus erythematosus, inflammatory bowel diseases (IBDs) comprising Crohn disease (CD), and ulcerative colitis (UC) which are chronic inflammatory conditions with polygenic susceptibility.

In one embodiment, the disease or disorder is inflammation, arthritis, rheumatoid arthritis, spondyiarthropathies, gouty arthritis, osteoarthritis, juvenile arthritis, and other arthritic conditions, systemic lupus erythematosus (SLE), skin-related conditions, psoriasis, eczema, burns, dermatitis, neuroinflammation, allergy, pain, neuropathic pain, fever, pulmonary disorders, lung inflammation, adult respiratory distress syndrome, pulmonary sarcoidosis, asthma, silicosis, chronic pulmonary inflammatory disease, and chronic obstructive pulmonary disease (COPD), cardiovascular disease, arteriosclerosis, myocardial infarction (including post-myocardial infarction indications), thrombosis, congestive heart failure, cardiac reperfusion injury, as well as complications associated with hypertension and/or heart failure such as vascular organ damage, restenosis, cardiomyopathy, stroke including ischemic and hemorrhagic stroke, reperfusion injury, renal reperfusion injury, ischemia including stroke and brain ischemia, and ischemia resulting from cardiac/coronary bypass, neurodegenerative disorders, liver disease and nephritis, gastrointestinal conditions, inflammatory bowel disease, Crohn's disease, gastritis, irritable bowel syndrome, ulcerative colitis, ulcerative diseases, gastric ulcers, viral and bacterial infections, sepsis, septic shock, gram negative sepsis, malaria, meningitis, HIV infection, opportunistic infections, cachexia secondary to infection or malignancy, cachexia secondary to acquired immune deficiency syndrome (AIDS), AIDS, ARC (AIDS related complex), pneumonia, herpes virus, myalgias due to infection, influenza, autoimmune disease, graft vs. host reaction and allograft rejections, treatment of bone resorption diseases, osteoporosis, multiple sclerosis, cancer, leukemia, lymphoma, colorectal cancer, brain cancer, bone cancer, epithelial call-derived neoplasia (epithelial carcinoma), basal cell carcinoma, adenocarcinoma, gastrointestinal cancer, lip cancer, mouth cancer, esophageal cancer, small bowel cancer, stomach cancer, colon cancer, liver cancer, bladder cancer, pancreas cancer, ovarian cancer, cervical cancer, lung cancer, breast cancer, skin cancer, squamous cell and/or basal cell cancers, prostate cancer, renal cell carcinoma, and other known cancers that affect epithelial cells throughout the body, chronic myelogenous leukemia (CML), acute myeloid leukemia (AML) and acute promyelocytic leukemia (APL), angiogenesis including neoplasia, metastasis, central nervous system disorders, central nervous system disorders having an inflammatory or apoptotic component, Alzheimer's disease, Parkinson's disease, Huntington's disease, amyotrophic lateral sclerosis, spinal cord injury, peripheral neuropathy, or B-Cell Lymphoma.

In one embodiment, the disease or disorder is selected from autoimmune diseases, inflammatory diseases, proliferative and hyper proliferative diseases, immunologically-mediated diseases, bone diseases, metabolic diseases, neurological and neurodegenerative diseases, cardiovascular diseases, hormone related diseases, allergies, asthma, and Alzheimer's disease. In one embodiment, the disease or disorder is selected from a proliferative disorder and an immune disorder.

As modulators of a STING protein, the compounds and compositions of this application are also useful in assessing, studying, or testing biological samples. One aspect of the application relates to modulating the activity of a STING protein in a biological sample, comprising contacting the biological sample with a compound or a composition of the application.

The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof. Modulation (e.g., inhibition or stimulation) of protein kinase activity in a biological sample is useful for a variety of purposes that are known to one of skill in the art. Examples of such purposes include, but are not limited to, blood transfusion, organ transplantation, and biological specimen storage.

Another aspect of this application relates to the study of a STING protein in biological and pathological phenomena; the study of intracellular signal transduction pathways mediated by STING protein. Examples of such uses include, but are not limited to, biological assays such as enzyme assays and cell-based assays.

The activity of the compounds and compositions of the present application as STING modulators may be assayed in vitro, in vivo, or in a cell line. In vitro assays include assays that determine modulation (e.g., inhibition or stimulation) of binding of a STING ligand to a STING protein through competitive binding assay. Alternate in vitro assays quantitate the ability of the agonist to bind to the protein kinase and may be measured either by radio or fluorescent labelling the agonist prior to binding, isolating the ligand/protein complex and determining the amount of radio/fluorescent label bound. Detailed conditions for assaying a compound utilized in this application as an antagonist of a STING protein are set forth in the Examples below.

In accordance with the foregoing, the present application provides a method for preventing or treating any of the diseases or disorders described above in a subject in need of such treatment, comprising administering to the subject a therapeutically effective amount of a compound of the application or an enantiomer, diastereomer, stereoisomer, or pharmaceutically acceptable salt thereof, or a pharmaceutical composition of the application. For any of the above uses, the required dosage will vary depending on the mode of administration, the particular condition to be treated and the effect desired.

Compounds and compositions of the application can be administered in therapeutically effective amounts in a combinational therapy with one or more therapeutic agents (pharmaceutical combinations) or modalities, e.g., anti-proliferative, anti-cancer, immunomodulatory, or anti-inflammatory agent, and/or non-drug therapies, etc. For example, synergistic effects can occur with anti-proliferative, anti-cancer, immunomodulatory, or anti-inflammatory substances. Where the compounds of the application are administered in conjunction with other therapies, dosages of the co-administered compounds will of course vary depending on the type of co-drug employed, on the specific drug employed, on the condition being treated and so forth.

Combination therapy may include the administration of the subject compounds in further combination with one or more other biologically active ingredients (such as, but not limited to, a second STING modulator (inhibitor or stimulator), a modulator (inhibitor or stimulator) of the cGAS-CDN-STING axis, or a modulator (inhibitor or stimulator) involved in the intracellular dsDNA mediated type-1 interferon activation. U.S. patent application Ser. No. 16/717,325 entitled MODULATING IMMUNE RESPONSES inventor Glen N. Barber, filed Dec. 17, 2019 is herein incorporated by reference in its entirety and for all purposes. Other biologically active ingredients may also include anti-proliferative agents, anti-cancer agents (e.g., chemotherapeutic agents), immunomodulatory agents, antibodies, etc. For instance, the compounds of the application can be used in combination with other pharmaceutically active compounds, preferably compounds that are able to enhance the agonist effect of the compounds of the application. The compounds of the application can be administered simultaneously (as a single preparation or separate preparation) or sequentially to the other drug therapy or treatment modality. In general, a combination therapy envisions administration of two or more drugs during a single cycle or course of therapy.

In one embodiment, the chemotherapeutic agent is an alkylating agent; an antibiotic; an anti-metabolite; a detoxifying agent; an interferon; a polyclonal or monoclonal antibody; an EGFR inhibitor; a HER2 inhibitor; a histone deacetylase inhibitor, a hormone; a mitotic inhibitor, an MTOR inhibitor, a multi-kinase inhibitor, a serine/threonine kinase inhibitor, a tyrosine kinase inhibitors; a VEGF/VEGFR inhibitor, a taxane or taxane derivative, an aromatase inhibitor, an anthracycline, a microtubule targeting drug, a topoisomerase poison drug, an inhibitor of a molecular target or enzyme (e.g., a kinase inhibitor), a cytidine analog drug, or any chemotherapeutic, anti-neoplastic or anti-proliferative agent listed in www.cancer.org/docroot/cdg/cdg_0.asp, last visited Apr. 27, 2020.

Exemplary alkylating agents include, but are not limited to, cyclophosphamide (Cytoxan; Neosar); chlorambucil (Leukeran); melphalan (Alkeran); carmustine (BiCNU); busulfan (Busulfex); lomustine (CeeNU); dacarbazine (DTIC-Dome); oxaliplatin (Eloxatin); carmustine (Gliadel); ifosfamide (Ifex); mechlorethamine (Mustargen); busulfan (Myleran); carboplatin (Paraplatin); cisplatin (CDDP; Platinol); temozolomide (Temodar); thiotepa (Thioplex); bendamustine (Treanda); or streptozocin (Zanosar).

Exemplary antibiotics include, but are not limited to, doxorubicin (Adriamycin); doxorubicin liposomal (Doxil); mitoxantrone (Novantrone); bleomycin (Blenoxane); daunorubicin (Cerubidine); daunorubicin liposomal (DaunoXome); dactinomycin (Cosmegen); epirubicin (Ellence); idarubicin (Idamycin); plicamycin (Mithracin); mitomycin (Mutamycin); pentostatin (Nipent); or valrubicin (Valstar).

Exemplary anti-metabolites include, but are not limited to, fluorouracil (Adrucil); capecitabine (Xeloda); hydroxyurea (Hydrea); mercaptopurine (Purinethol); pemetrexed (Alimta); fludarabine (Fludara); nelarabine (Arranon); cladribine (Cladribine Novaplus); clofarabine (Clolar); cytarabine (Cytosar-U); decitabine (Dacogen); cytarabine liposomal (DepoCyt); hydroxyurea (Droxia); pralatrexate (Folotyn); floxuridine (FUDR); gemcitabine (Gemzar); cladribine (Leustatin); fludarabine (Oforta); methotrexate (MTX; Rheumatrex); methotrexate (Trexall); thioguanine (Tabloid); TS-1 or cytarabine (Tarabine PFS).

Exemplary detoxifying agents include, but are not limited to, amifostine (Ethyol) or mesna (Mesnex).

Exemplary interferons include, but ae not limited to, interferon alfa-2b (Intron A) or interferon alfa-2a (Roferon-A).

Exemplary polyclonal or monoclonal antibodies include, but are not limited to, trastuzumab (Herceptin); ofatumumab (Arzerra); bevacizumab (Avastin); rituximab (Rituxan);

cetuximab (Erbitux); panitumumab (Vectibix); tositumomab/iodine[131] tositumomab (Bexxar); alemtuzumab (Campath); ibritumomab (Zevalin; In-111; Y-90 Zevalin); gemtuzumab (Mylotarg); eculizumab (Soliris) ordenosumab.

Exemplary EGFR inhibitors include, but are not limited to, gefitinib (Iressa); lapatinib (Tykerb); cetuximab (Erbitux); erlotinib (Tarceva); panitumumab (Vectibix); PKI-166; canertinib (CI-1033); matuzumab (Emd7200) or EKB-569.

Exemplary HER2 inhibitors include, but are not limited to, trastuzumab (Herceptin); lapatinib (Tykerb) or AC-480.

Exemplary histone Deacetylase Inhibitors include, but are not limited to, vorinostat (Zolinza).

Exemplary hormones include, but are not limited to, tamoxifen (Soltamox; Nolvadex); raloxifene (Evista); megestrol (Megace); leuprolide (Lupron; Lupron Depot; Eligard; Viadur); fulvestrant (Faslodex); letrozole (Femara); triptorelin (Trelstar LA; Trelstar Depot); exemestane (Aromasin); goserelin (Zoladex); bicalutamide (Casodex); anastrozole (Arimidex); fluoxymesterone (Androxy; Halotestin); medroxyprogesterone (Provera; Depo-Provera); estramustine (Emcyt); flutamide (Eulexin); toremifene (Fareston); degarelix (Firmagon); nilutamide (Nilandron); abarelix (Plenaxis); or testolactone (Teslac).

Exemplary mitotic inhibitors include, but are not limited to, paclitaxel (Taxol; Onxol; Abraxane); docetaxel (Taxotere); vincristine (Oncovin; Vincasar PFS); vinblastine (Velban); etoposide (Toposar, Etopophos; VePesid); teniposide (Vumon); ixabepilone (Ixempra); nocodazole; epothilone; vinorelbine (Navelbine); camptothecin (CPT); irinotecan (Camptosar); topotecan (Hycamtin); amsacrine or lamellarin D (LAM-D).

Exemplary MTOR inhibitors include, but are not limited to, everolimus (Afinitor) or temsirolimus (Torisel); rapamune, ridaforolimus; or AP23573.

Exemplary multi-kinase inhibitors include, but are not limited to, sorafenib (Nexavar); sunitinib (Sutent); BIBW 2992; E7080; Zd6474; PKC-412; motesanib; or AP24534.

Exemplary serine/threonine kinase inhibitors include, but are not limited to, ruboxistaurin; eril/easudil hydrochloride; flavopiridol; seliciclib (CYC202; Roscovitrine); SNS-032 (BMS-387032); Pkc412; bryostatin; KAI-9803; SF1126; VX-680; Azd1152; Arry-142886 (AZD-6244); SCIO-469; GW681323; CC-401; CEP-1347 or PD 332991.

Exemplary tyrosine kinase inhibitors include, but are not limited to, erlotinib (Tarceva); gefitinib (Iressa); imatinib (Gleevec); sorafenib (Nexavar); sunitinib (Sutent); trastuzumab (Herceptin); bevacizumab (Avastin); rituximab (Rituxan); lapatinib (Tykerb); cetuximab (Erbitux); panitumumab (Vectibix); everolimus (Afinitor); alemtuzumab (Campath); gemtuzumab (Mylotarg); temsirolimus (Torisel); pazopanib (Votrient); dasatinib (Sprycel); nilotinib (Tasigna); vatalanib (Ptk787; ZK222584); CEP-701; SU5614; MLN518; XL999; VX-322; Azd0530; BMS-354825; SKI-606 CP-690; AG-490; WHI-P154; WHI-P131; AC-220; or AMG888.

Exemplary VEGF/VEGFR inhibitors include, but are not limited to, bevacizumab (Avastin); sorafenib (Nexavar); sunitinib (Sutent); ranibizumab; pegaptanib; or vandetinib.

Exemplary microtubule targeting drugs include, but are not limited to, paclitaxel, docetaxel, vincristin, vinblastin, nocodazole, epothilones and navelbine.

Exemplary topoisomerase poison drugs include, but are not limited to, teniposide, etoposide, adriamycin, camptothecin, daunorubicin, dactinomycin, mitoxantrone, amsacrine, epirubicin and idarubicin.

Exemplary taxanes or taxane derivatives include, but are not limited to, paclitaxel and docetaxol.

Exemplary general chemotherapeutic, anti-neoplastic, anti-proliferative agents include, but are not limited to, altretamine (Hexalen); isotretinoin (Accutane; Amnesteem; Claravis; Sotret); tretinoin (Vesanoid); azacitidine (Vidaza); bortezomib (Velcade) asparaginase (Elspar); levamisole (Ergamisol); mitotane (Lysodren); procarbazine (Matulane); pegaspargase (Oncaspar); denileukin diftitox (Ontak); porfimer (Photofrin); aldesleukin (Proleukin); lenalidomide (Revlimid); bexarotene (Targretin); thalidomide (Thalomid); temsirolimus (Torisel); arsenic trioxide (Trisenox); verteporfin (Visudyne); mimosine (Leucenol); (1M tegafur-0.4 M 5-chloro-2,4-dihydroxypyrimidine-1 M potassium oxonate) or lovastatin.

Exemplary kinase inhibitors include, but are not limited to, Bevacizumab (targets VEGF), BIBW 2992 (targets EGFR and Erb2), Cetuximab/Erbitux (targets Erb1), Imatinib/Gleevic (targets Bcr-Abl), Trastuzumab (targets Erb2), Gefitinib/Iressa (targets EGFR), Ranibizumab (targets VEGF), Pegaptanib (targets VEGF), Erlotinib/Tarceva (targets Erb1), Nilotinib (targets Bcr-Abl), Lapatinib (targets Erb1 and Erb2/Her2), GW-572016/lapatinib ditosylate (targets HER2/Erb2), Panitumumab/Vectibix (targets EGFR), Vandetinib (targets RET/VEGFR), E7080 (multiple targets including RET and VEGFR), Herceptin (targets HER2/Erb2), PKI-166 (targets EGFR), Canertinib/CI-1033 (targets EGFR), Sunitinib/SU-11464/Sutent (targets EGFR and FLT3), Matuzumab/Emd7200 (targets EGFR), EKB-569 (targets EGFR), Zd6474 (targets EGFR and VEGFR), PKC-412 (targets VEGR and FLT3), Vatalanib/Ptk787/ZK222584 (targets VEGR), CEP-701 (targets FLT3), SU5614 (targets FLT3), MLN518 (targets FLT3), XL999 (targets FLT3), VX-322 (targets FLT3), Azd0530 (targets SRC), BMS-354825 (targets SRC), SKI-606 (targets SRC), CP-690 (targets JAK), AG-490 (targets JAK), WHI-P154 (targets JAK), WHI-P131 (targets JAK), sorafenib/Nexavar (targets RAF kinase, VEGFR-1, VEGFR-2, VEGFR-3, PDGFR-ß, KIT, FLT-3, and RET), Dasatinib/Sprycel (BCR/ABL and Src), AC-220 (targets Flt3), AC-480 (targets all HER proteins, "panHER"), Motesanib diphosphate (targets VEGF1-3, PDGFR, and c-kit), Denosumab (targets RANKL, inhibits SRC), AMG888 (targets HER3), and AP24534 (multiple targets including Flt3).

In one embodiment, the compounds may be administered in combination with one or more separate pharmaceutical agents, e.g., a chemotherapeutic agent, an immunotherapeutic agent, or an adjunctive therapeutic agent.

As used herein, "combination therapy" or "co-therapy" includes the administration of a compound of the present application, or a pharmaceutically acceptable salt or ester thereof, and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may be, but generally is not, intended to encompass the administration of two or more of these therapeutic agents as part of separate monotherapy regimens that incidentally and arbitrarily result in the combinations of the present application.

"Combination therapy" is intended to embrace administration of these therapeutic agents in a sequential manner, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Definitions

Listed below are definitions of various terms used in this application. These definitions apply to the terms as they are used throughout this specification and claims, unless otherwise limited in specific instances, either individually or as part of a larger group.

The transitional term "comprising" is synonymous with "including," "containing," or "characterized by," is inclusive or open-ended and does not exclude additional, unrecited elements or method steps.

The transitional phrase "consisting of" excludes any element, step, or ingredient not specified in the claim, but does not exclude additional components or steps that are unrelated to the invention such as impurities ordinarily associated with a composition.

The transitional phrase "consisting essentially of" limits the scope of a claim to the specified materials or steps and those that do not materially affect the basic and novel characteristic(s) of the claimed invention.

The term "alkyl," as used herein, refers to saturated, straight or branched-chain hydrocarbon radicals containing, in certain embodiments, between one and six carbon atoms. Examples of $C_1$-$C_6$ alkyl radicals include, but are not limited to, methyl, ethyl, propyl, isopropyl, n-butyl, tert-butyl, neopentyl, and n-hexyl radicals.

The term "per halo alkyl," as used herein, refers to saturated, straight or branched-chain carbon radicals containing no hydrogen atoms bonded to the carbon, in certain embodiments, between one and six carbon atoms. Examples of $C_1$-$C_6$ alkyl radicals include, but are not limited to, methyl, ethyl, propyl, isopropyl, n-butyl, tert-butyl, neopentyl, and n-hexyl radicals. The halo as used herein refers to halogen atoms.

The term "alkenyl," as used herein, denotes a monovalent group derived from a hydrocarbon moiety containing, in certain embodiments, from two to six carbon atoms having at least one carbon-carbon double bond. The double bond may or may not be the point of attachment to another group. Alkenyl groups include, but are not limited to, for example, ethenyl, propenyl, butenyl, 1-methyl-2-buten-1-yl, pentenyl, hexenyl, heptenyl, octenyl, nonenyl, decenyl, and the like.

The term "alkynyl," as used herein, denotes a monovalent group derived from a hydrocarbon moiety containing, in certain embodiments, from two to six carbon atoms having at least one carbon-carbon triple bond. The triple bond may or may not be the point of attachment to another group. Alkynyl groups include, but are not limited to, for example, ethynyl, propynyl, butynyl, pentynyl, hexynyl, heptynyl, octynyl, nonynyl, decynyl, and the like.

The term "alkoxy" refers to an —O-alkyl radical.

The terms "hal," "halo," and "halogen," as used herein, refer to an atom selected from fluorine, chlorine, bromine and iodine.

The term "cycloalkyl," as used herein, denotes a monovalent group derived from a monocyclic or polycyclic saturated or partially unsaturated carbocyclic ring compound. Examples of $C_3$-$C_8$ cycloalkyl include, but not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo [2.2.1]heptyl, and bicyclo [2.2.2]octyl.

The term "cycloalkenyl," as used herein, denotes a monovalent group derived from a monocyclic or polycyclic saturated or partially unsaturated carbocyclic ring compound comprising at least one carbon-carbon double bond. Examples of $C_4$-$C_8$ cycloalkenyl include, but not limited to, cyclobutenyl, cyclopentenyl, cyclohexenyl, cyclopentenyl and cyclooctenyl.

The term "aryl," as used herein, refers to a mono- or poly-cyclic carbocyclic ring system having one or more aromatic rings, fused or non-fused, including, but not limited to, phenyl, naphthyl, tetrahydronaphthyl, indanyl, indenyl, and the like.

The term "aralkyl," as used herein, refers to an alkyl residue, such as those described herein, attached to an aryl ring, such as those described herein. Examples include, but are not limited to, benzyl, phenethyl, and the like.

The term "heteroaryl," as used herein, refers to a mono- or poly-cyclic (e.g., bi-, or tri-cyclic or more) fused or non-fused, radical or ring system having at least one aromatic ring, having from five to ten ring atoms of which one ring atoms is selected from S, O, and N; zero, one, or two ring atoms are additional heteroatoms independently selected from S, O, and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, indazoyl, cinnolinyl, phthalazinyl, pyridazinyl, indolyl, acridinyl, benzoquinolinyl, pyrimidinyl, a purinyl, pyrrolopyrimidinyl, quinoxalinyl, quinazolinyl, indazolinyl, and phthalazinyl, and the like.

The term "heteroaralkyl," as used herein, refers to an alkyl residue, such as those described herein, attached to a heteroaryl ring, such as those described herein. Examples include, but are not limited to, pyridinylmethyl, pyrimidinylethyl, and the like.

In accordance with the application, any of the aryls, substituted aryls, heteroaryls and substituted heteroaryls described herein, can be any aromatic group. Aromatic groups can be substituted or unsubstituted.

The term "heterocyclyl," as used herein, refers to a non-aromatic mono- or poly-cyclic (e.g., bi-, or tri-cyclic or more) fused or non-fused, radical or ring system having from three to ten ring atoms of which one ring atoms is selected from S, O, and N; zero, one, or two ring atoms are additional heteroatoms independently selected from S, O, and N; and the remaining ring atoms are carbon. Representative heterocycloalkyl groups include, but are not limited to, [1,3]dioxolanyl, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl, and the like.

The term "alkylamino" refers to a group having the structure —NH($C_1$-$C_{12}$ alkyl), e.g., —NH($C_1$-$C_6$ alkyl), where $C_1$-$C_6$ alkyl is as previously defined.

The term "dialkylamino" refers to a group having the structure —N($C_1$-$C_{12}$ alkyl)$_2$, e.g., —NH($C_1$-$C_6$ alkyl), where $C_1$-$C_6$alkyl is as previously defined.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates. Examples of aliphatic carbonyls include, but are not limited to, acetyl, propionyl, 2-fluoroacetyl, butyryl, 2-hydroxy acetyl, and the like.

The term "ester" includes compounds or moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

As described herein, compounds of the application and moieties present in the compounds may optionally be substituted with one or more substituents, such as are illustrated generally above, or as exemplified by particular classes, subclasses, and species of the application. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. The terms "optionally substituted", "optionally substituted alkyl," "optionally substituted alkenyl," "optionally substituted alkynyl", "optionally substituted cycloalkyl," "optionally substituted cycloalkenyl," "optionally substituted aryl", "optionally substituted heteroaryl," "optionally substituted aralkyl", "optionally substituted heteroaralkyl," "optionally substituted heterocyclyl," and any other optionally substituted group as used herein, refer to groups that are substituted or unsubstituted by independent replacement of one, two, or three or more of the hydrogen atoms thereon with substituents including, but not limited to: —F, —Cl, —Br, —I, —OH, protected hydroxy, —NO$_2$, —CN, —NH$_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkenyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkenyl, —C(O)—$C_3$-$C_{12}$-cycloalkyl, —C(O)-aryl, —C(O)— heteroaryl, —C(O)-heterocycloalkyl, —CONH$_2$, —CONH—$C_1$-$C_{12}$-alkyl, —CONH—$C_2$-$C_{12}$-alkenyl, —CONH—$C_2$-$C_{12}$-alkenyl, —CONH—$C_3$-$C_{12}$-cycloalkyl, —CONH-aryl, —CONH-heteroaryl, —CONH-heterocycloalkyl, —OCO$_2$—$C_1$-$C_{12}$-alkyl, —OCO$_2$—$C_2$-$C_{12}$-alkenyl, —OCO$_2$—$C_2$-$C_{12}$-alkenyl, —OCO$_2$—$C_3$-$C_{12}$-cycloalkyl, —OCO$_2$-aryl, —OCO$_2$-heteroaryl, —OCO$_2$-heterocycloalkyl, —OCONH$_2$, —OCONH—$C_1$-$C_{12}$-alkyl, —OCONH—$C_2$-$C_{12}$-alkenyl, —OCONH—$C_2$-$C_{12}$-alkenyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkenyl, —NHC(O)—$C_3$-$C_{12}$-cycloalkyl, —NHC(O)-aryl, —NHC(O)-heteroaryl, —NHC(O)-heterocycloalkyl, —NHCO$_2$—$C_1$-$C_{12}$-alkyl, —NHCO$_2$—$C_2$-$C_{12}$-alkenyl, —NHCO$_2$—$C_2$-$C_{12}$-alkenyl, —NHCO$_2$—$C_3$-$C_{12}$-cycloalkyl, —NHCO$_2$-aryl, —NHCO$_2$-heteroaryl, —NHCO$_2$-heterocycloalkyl, NHC(O)NH$_2$, —NHC(O)NH—$C_1$-$C_{12}$-alkyl, —NHC(O)NH—$C_2$-$C_{12}$-alkenyl, —NHC(O)NH—$C_2$-$C_{12}$-alkenyl, —NHC(O)NH—$C_3$-$C_{12}$-cycloalkyl, —NHC(O)NH-aryl, —NHC(O)NH-heteroaryl, NHC(O)NH-heterocycloalkyl, —NHC(S)NH$_2$, —NHC(S)NH—$C_1$-$C_{12}$-alkyl, —NHC(S)NH—$C_2$-$C_{12}$-alkenyl, —NHC(S)NH—$C_2$-$C_{12}$-alkenyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—$C_1$-$C_{12}$-alkyl, —NHC(NH)NH—$C_2$-$C_{12}$-alkenyl, —NHC(NH)NH—$C_2$-$C_{12}$-alkenyl, —NHC(NH)NH—$C_3$-$C_{12}$-cycloalkyl, —NHC(NH)NH-aryl, —NHC(NH)NH-heteroaryl, —NHC(NH)NHheterocycloalkyl, —NHC(NH)—$C_1$-$C_{12}$-alkyl, —NHC(NH)—$C_2$-$C_{12}$-alkenyl, —NHC(NH)—$C_2$-$C_{12}$-alkenyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkenyl, C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkenyl, —S(O)—$C_3$-$C_{12}$-cycloalkyl, —S(O)-aryl, —S(O)-heteroaryl, —S(O)-heterocycloalkyl- SO$_2$NH$_2$, —SO$_2$NH—$C_1$-$C_{12}$-alkyl, —SO$_2$NH—$C_2$-$C_{12}$-alkenyl, —SO$_2$NH—$C_2$-$C_{12}$-alkenyl, —SO$_2$NH—$C_3$-$C_{12}$-cycloalkyl, —SO$_2$NH-aryl, —SO$_2$NH-heteroaryl, —SO$_2$NH-heterocycloalkyl, —NHSO$_2$—$C_1$-$C_{12}$-alkyl, —NHSO$_2$—$C_2$-$C_{12}$-alkenyl, —NHSO$_2$—$C_2$-$C_{12}$-alkenyl, —NHSO$_2$—$C_3$-$C_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —$C_3$-$C_{12}$-Cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkenyl, —S—$C_3$-$C_{12}$-cycloalkyl, —S-aryl, —S-heteroaryl, —S-heterocycloalkyl, or methylthiomethyl.

The term "cancer" includes, but is not limited to, the following cancers: epidermoid Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma, and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal, rectum; Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma) hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, undifferentiated thyroid cancer, multiple endocrine neoplasia type 2A, multiple endocrine neoplasia type 2B, familial medullary thyroid cancer, pheochromocytoma, paraganglioma; and Adrenal glands: neuroblastoma. Thus, the term "cancerous cell" as provided herein, includes a cell afflicted by any one of the above-identified conditions.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

"Treat", "treating" and "treatment" refer to a method of alleviating or abating a disease and/or its attendant symptoms.

As used herein, "preventing" or "prevent" describes reducing or eliminating the onset of the symptoms or complications of the disease, condition or disorder.

The terms "disease(s)", "disorder(s)", and "condition(s)" are used interchangeably, unless the context clearly dictates otherwise.

The term "therapeutically effective amount" of a compound or pharmaceutical composition of the application, as used herein, means a sufficient amount of the compound or pharmaceutical composition so as to decrease the symptoms of a disorder in a subject. As is well understood in the medical arts a therapeutically effective amount of a compound or pharmaceutical composition of this application will be at a reasonable benefit/risk ratio applicable to any medical treatment. It will be understood, however, that the total daily usage of the compounds and compositions of the present application will be decided by the attending physician within the scope of sound medical judgment. The specific modulatory (e.g., inhibitory or stimulatory) dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable salt" refers to those salts of the compounds formed by the process of the present application which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in *J. Pharmaceutical Sciences*, 66: 1-19 (1977), which is herein expressly incorporated by reference in its entirety and for all purposes. The salts can be prepared in situ during the final isolation and purification of the compounds of the application, or separately by reacting the free base or acid function with a suitable acid or base.

Examples of pharmaceutically acceptable salts include, but are not limited to, nontoxic acid addition salts: salts formed with inorganic acids such as hydrochloric acid, hydrobromic acid, phosphoric acid, sulfuric acid and perchloric acid, or with organic acids such as acetic acid, maleic acid, tartaric acid, citric acid, succinic acid or malonic acid. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, 7-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counter ions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present application which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein, refers to those prodrugs of the compounds formed by the process of the present application which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present application.

"Prodrug", as used herein, means a compound which is convertible in vivo by metabolic means (e.g., by hydrolysis) to afford any compound delineated by the formulae of the instant application. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38(1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002), which are all herein expressly incorporated by reference in their entireties and for all purposes.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

This application also encompasses pharmaceutical compositions containing, and methods of treating disorders through administering, pharmaceutically acceptable prodrugs of compounds of the application. For example, compounds of the application having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the application. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxy carbonyls, as outlined in *Advanced Drug Delivery Reviews,* 1996, 19, 1-15, which is herein expressly incorporated by reference in its entirety and for all purposes. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J Med Chem. 1996, 39, 10, which is herein expressly incorporated by reference in its entirety and for all purposes. Free amines can also be derivatized as amides, sulfonamides or phosphonamides. All of these prodrug moieties may incorporate groups including but not limited to ether, amine and carboxylic acid functionalities.

Combinations of substituents and variables envisioned by this application are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

When any variable (e.g., $R_1$) occurs more than one time in any constituent or formula for a compound, its definition at each occurrence is independent of its definition at every other occurrence. Thus, for example, if a group is shown to be substituted with one or more R moieties, then R at each occurrence is selected independently from the definition of R. Also, combinations of substituents and/or variables are permissible, but only if such combinations result in stable compounds within a designated atom's normal valency.

In addition, some of the compounds of this application have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms, and other stereoisomeric forms that may be defined, in terms of absolute stereochemistry, as (R)- or (S)-, or as (D)- or (L)- for amino acids. When the compounds described herein contain olefinic double bonds or other centers of geometric asymmetry, and unless specified otherwise, it is intended that the compounds include both E and Z geometric isomers. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion. All such isomeric forms of such compounds are expressly included in the present application.

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four non-identical substituents is termed a "chiral center".

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center, e.g., carbon. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Furthermore, the structures and other compounds discussed in this application include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques; it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose. Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine. The compounds of this application may also be represented in multiple tautomeric forms, in such instances, the application expressly includes all tautomeric forms of the compounds described herein (e.g., alkylation of a ring system may result in alkylation at multiple sites, the application expressly includes all such reaction products).

In the present application, the structural formula of the compound represents a certain isomer for convenience in some cases, but the present application includes all isomers, such as geometrical isomers, optical isomers based on an asymmetrical carbon, stereoisomers, tautomers, and the like.

In the present specification, the structural formula of the compound represents a certain isomer for convenience in some cases, but the present application includes all isomers, such as geometrical isomers, optical isomers based on an asymmetrical carbon, stereoisomers, tautomers, and the like.

Additionally, the compounds of the present application, for example, the salts of the compounds, can exist in either hydrated or unhydrated (the anhydrous) form or as solvates with other solvent molecules. Non-limiting examples of hydrates include monohydrates, dihydrates, etc. Non-limiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$ In the present specification, the structural formula of the compound represents a certain isomer for convenience in some cases, but the present application includes all isomers, such as geometrical isomers, optical isomers based on an asymmetrical carbon, stereoisomers, tautomers, and the like.

EXAMPLES

The purity of all compounds was over 95% and was analyzed with Waters LC/MS system. $^1$H NMR was obtained at 400 MHz. Chemical shifts are reported relative to dimethyl sulfoxide ($\delta$=2.50) for $^1$H NMR. Data are reported as (br=broad, s=singlet, d=doublet, t=triplet, q=quartet, m=multiplet).

Abbreviations used in the following examples and elsewhere herein are: AcOH acetic acid; atm atmosphere; BMDM bone marrow derived macrophages; $BOC_2O$ di-tert-butyl dicarbonate; cGAMP cyclic[G(2',5')pA(3',5')p]; cGAS cyclic Guanosine Monophosphate-Adenosine Monophosphate synthase; $CuSO_4$ copper sulfate; $CDCl_3$ deuterated chloroform; CDN cyclic dinucleotides; DCM dichloromethane; DIEA N,N-diisopropylethylamine; DMA N,N-dimethylacetamide; DMAP 4-dimethylaminopyridine; DMF N,N-dimethylformamide; DMSO dimethyl sulfoxide; DMSO-$d_6$ deuterated dimethyl sulfoxide; dsDNA double stranded deoxyribonucleic acid; EDCI 1-ethyl-3-(3-dimethylaminopropyl) carbodiimide; ESI electrospray ionization; EtOAc ethyl acetate; H&E hematoxylin and eosin; HCl hydrochloric acid; h hour(s); HPLC high-performance liquid chromatography; hTERT immortalized human fibroblasts stably transfected with the type I IFN promoter driving luciferase as well as the CMV promoter driving SEAP or pIFNβ-Glu; IFN interferon; IRF3 Interferon Regulatory Factor 3; ISD Interferon Stimulatory DNA; LCMS liquid chromatography-mass spectrometry; mL milliliter; MeCN acetonitrile; MEF Murine Embryonic Fibroblasts; MeOH methanol; mg milligram; mmol millimole; $MgSO_4$ magnesium sulfate; MHz megahertz; min minutes; MS mass spectrometry; $Na_2CO_3$ sodium carbonate; $NaHCO_3$ sodium bicarbonate; NF-kB nuclear factor kappa-light-chain-enhancer of activated B cells; NMR nuclear magnetic resonance; PCR polymerase chain reaction; STING Stimulator of Interferon Genes; Tf triflate; TKO TREX1 KnockOut; $Pd_2(dba)_3$ tris (dibenzylideneacetone)dipalladium(0); $Pd(PPh_3)_2Cl_2$ bis (triphenylphosphine)palladium(II) dichloride; ppm parts per million; PCR polymerase chain reaction; PTSA para-toluene sulfonic acid; qPCR quantitative real time PCR; rt room temperature; t-BuOH tert-butanol; TBAF tetra-n-butylammonium fluoride; TBK1 TANK-binding kinase 1; THF tetrahydrofuran; TFA trifluoroacetic acid; TMS trimethylsilane; TLC thin layer chromatography; TSA thermal shift assay; μL microliter; WT Wild Type.

Example 1: Identification of small molecule antagonists of STING. In the presence of cytosolic DNA species, STING becomes activated to drive the transcription of cytokines such as type I IFN. Compounds binding to STING via TSA were subsequently examined for their ability to prevent cytosolic DNA species from activating the type I interferon (IFN) promoter, using a live cell assay. This assay comprised immortalized human fibroblasts that were stably transfected with the type I IFN promoter driving luciferase as well as the CMV promoter driving SEAP (hTERT-pIFNβ-Glu). The live cell assay has previously been disclosed in PCT/JS2019/025380 entitled IFN-βETA REPORTER SYSTEM FOR IMMORTALIZED PRIMARY CELLS inventor Glen N. Barber, which was filed Apr. 2, 2018 and published as WO2019195285, and which is herein incorporated by reference in its entirety and for all purposes. The ability of the small molecules to prevent activation of the type I IFN promoter and the transcription of luciferase, but not SEAP in response to cytosolic DNA species was assessed. The activation of STING, typically by CDNs, in turn activates the transcription factors NF-κB and IRF3, both of which are required to induce the transcriptional stimulation of the Type I IFN promoter, but not the CMV promoter as IRF3 and NF-kB transcription factor binding sites are not contained in the CMV promoter. The assay identified the small molecule Compound Y1 in the first screen (HTS), where the level of luciferase was not able to activate the type I IFN promoter or induce the expression of luciferase (see Table I).

Compound Y1 inhibited activation of the type I IFN promoter in hTERT-pIFNβ-Glu in response to the presence of cytosolic DNA (referred to as ISD treatment) at 10 μM (493) and 50 μM (490) concentrations (Mock is shown (210), ISD treatment only (220) was used as a control) (see FIG. 2A). The ability of compound Y1 administered onto normal hTERT cells to prevent cytosolic DNA from activating STING was assessed (FIG. 2B-FIG. 2E). This was achieved by examining whether Y1 compound inhibited Type I IFN production using an ELISA assay (FIG. 2B) and quantitative real time PCR (FIG. 2C). The data showed that compound Y1 dramatically decreased IFNβ expression and production in hTERT cells (FIG. 2B-FIG. 2C). In addition, the level of STING phosphorylation (STING is phosphorylated following activation) and the subsequent phosphorylation of TBK1, the kinase of IRF3 was assessed (FIG. 2D). Phosphorylation of TBK1 and IRF3 are required for activation of the type I IFN promoter. The results indicated that compound Y1 robustly prevented STING phosphorylation and subsequently TBK1 and IRF3 phosphorylation (FIG. 2D). Compound Y1 reproducibly prevented STING activity, effectively preventing STING trafficking which is a requirement for STING function, STING phosphorylation, as well as TBK1 phosphorylation and IRF3 phosphorylation (FIG. 2D). FIG. 2E are photographs showing confocal analysis of STING trafficking using anti-Sting with and/without Y1. Thus, Y1 binds to STING and impedes STING function, in human cells.

Figure 3E:
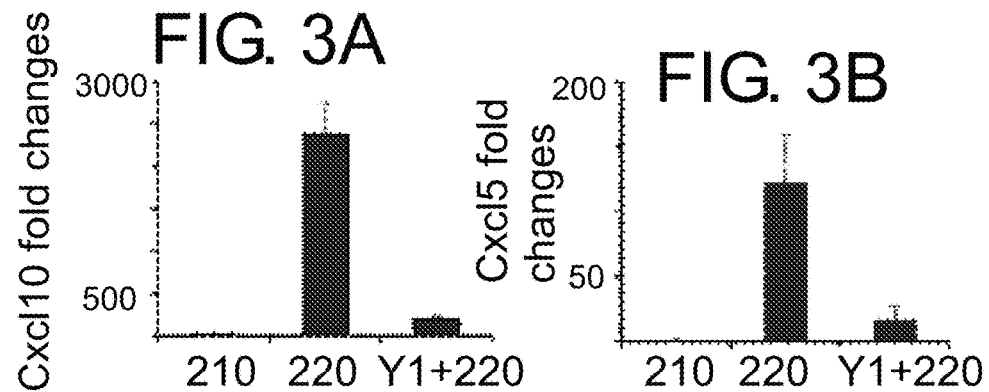
FIG. 3E shows photographs of confocal analysis for IRF3 and p65 translocation in MEF cells with Y1+220, Mock is shown (210), ISD treatment only (220) used as control, treated same as in FIG. 3A, performed to evaluate inhibition of STING signaling by Y1, according to an embodiment of the invention.
Figure 3E:
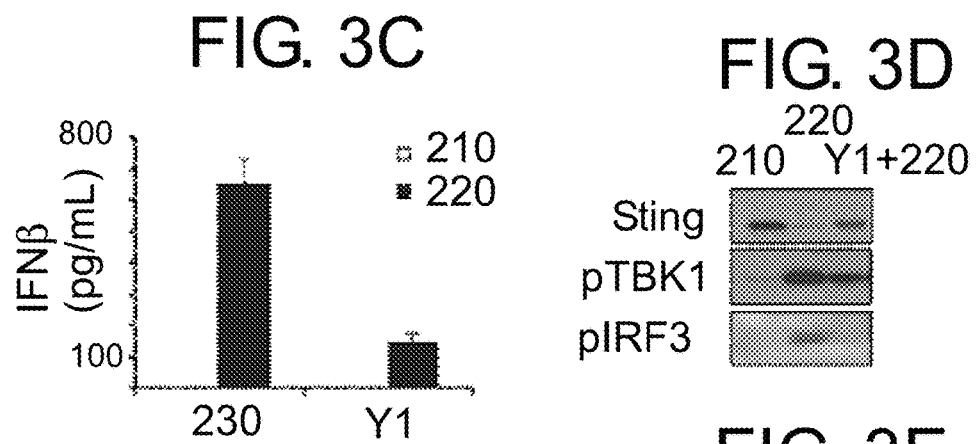
Figure 3E:
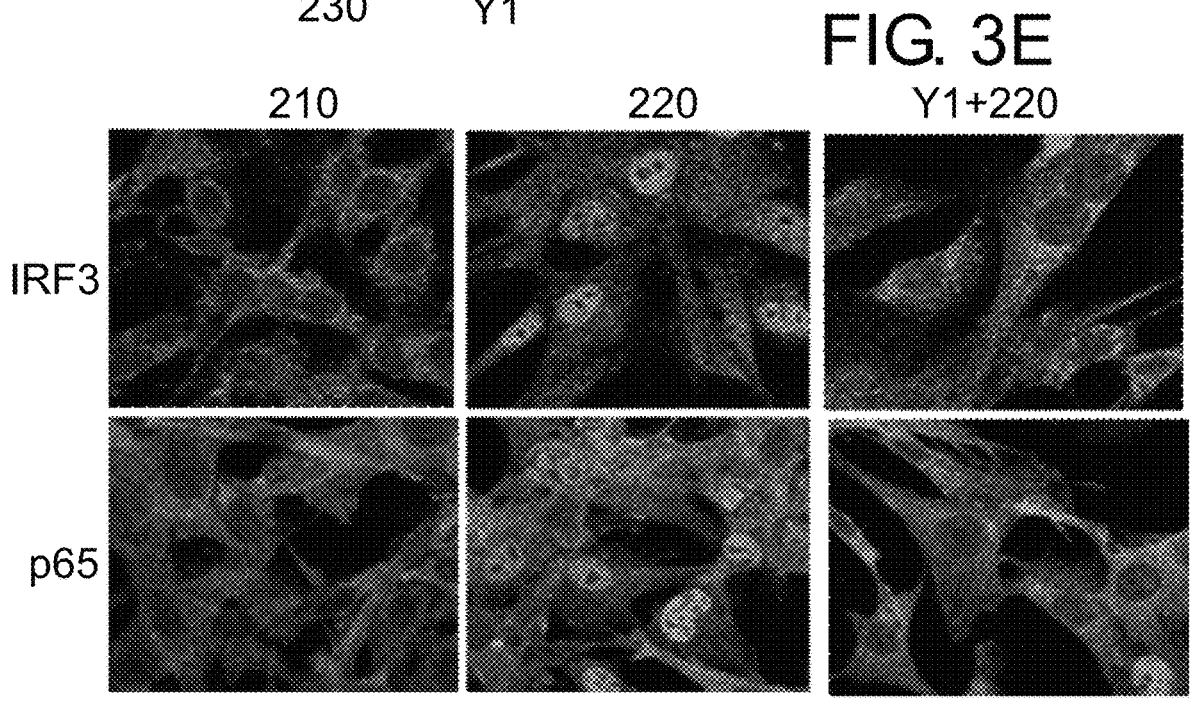

Murine embryonic fibroblasts (MEFs) were also treated with the compound Y1 and then treated them with cytosolic DNA (220). The production of STING-inducible cytokines Cxcl10 and Cxcl5 in response to ISD were dramatically decreased in the presence of compound Y1. The ability of cytosolic DNA (220) to stimulate the production of these cytokines was prevented by the presence of compound Y1 (FIG. 3A and FIG. 3B). Compound Y1 also reproducibly decreased the production of IFNβ (FIG. 3C). Further, compound Y1 prevented the phosphorylation of either TBK1 or IRF3 (FIG. 3D). Compound Y1 also prevented the activation of NF-kB (p65) as demonstrated by this transcription factor not translocating to the nucleus in response to cytosolic DNA stimulation (FIG. 3E). Compound Y1 binds to and inhibits STING activity, which prevents the activation of both IRF3 and NF-kB which are required for type I IFN and other cytokine gene induction in murine cells as well as human cells.

Example 2: Based on the structure of Y1, approximately 500 similar compounds were tested for their ability to bind to STING in TSA. Approximately forty three (43) exhibited the ability to associate with STING as determined by TSA. All compounds were tested for their ability to prevent the ability of cytosolic DNA (220) to activate STING signaling and the transcription of the type I IFN promoter, driving luciferase in (hTERT-pIFNβ-Glu) (which requires both IRF3 and NF-kB). Fourteen (14) of the 43 compounds were able to prevent cytosolic DNA-dependent activation of STING signaling. Based on the structures of the 14 compounds, twenty five (25) novel analogs, not in the public domain, were chemically synthesized. These novel compounds were tested for their ability to prevent STING function which activates the type I Ifn promoter in human cells. Of the 25 novel analogs, eight (8) were found to meet the criteria to inhibit STING dependent signaling (Y2, Y3, Y4, Y5, Y6, Y7, Y8 and Y9) (Table 1).

To confirm the inhibitory effects of Y1 with the 8 novel compounds, the study was repeated in hTERT-pIFNβ-Glu cells with Y1, Y2, Y3, Y4, Y5, Y6, Y7, Y8 and Y9 at 50 μM (490) or 25 μM (492) concentrations. hTERT-pIFNβ-Glu cells were treated and subsequently the cells transfected with cytosolic DNA which activates STING signaling. This assay verified that six (6) analogs (Y4, Y5, Y6, Y7, Y8 and Y9) showed robust inhibitory activity of the type I IFN promoter in hTERT-pIFNβ-Glu in response to the presence of ISD, compared to Y1, Y2 and Y3 (see FIG. 4A).

The ability of the 6 novel analogs (Y4, Y5, Y6, Y7, Y8 and Y9) to prevent STING activation and the downstream activation of STING were assessed. Normal hTERT cells were treated with Y4, Y5, Y6, Y7, Y8 and Y9 and stimulated with ISD. The majority of the compounds were able to prevent the phosphorylation of TBK1 and IRF3 as well as STING phosphorylation in a dose dependent manner (see FIG. 4B). In addition, the production of STING-inducible cytokines Cxcl10 was robustly inhibited in the presence of Y4, Y5, Y6, Y7, Y8 and Y9 (see FIG. 4C). However, only three (3) compounds (Y4, Y8 and Y9) reproducibly prevented STING trafficking and IRF3 phosphorylation (FIG. 4D and FIG. 4E). Accordingly, Y4, Y8 and Y9 bind to and inhibit STING activity, which prevents the activation of both IRF3 and NF-kB.

The STING-dependent phosphorylation of TBK1 and IRF3 and Cxcl10 expression by qPCR in MEF cells treated with three (3) analogs Y4, Y8 and Y9 (compared with Y1, Y5, Y6 and Y7) and then stimulated with cytoplasmic DNA (220) were examined (see FIG. 5A and FIG. 5B). This data confirmed that Y4, Y8 and Y9 can prevent the phosphorylation of TBK1 and IRF3 as well as STING phosphorylation and impede the production of Cxcl10 in response to cytosolic DNA (FIG. 5A and FIG. 5B). Further, Y4 and Y9 potently prevented the translocation of p65 (FIG. 5C). The 3 analogs (Y1, Y4 and Y9) can bind to and specifically prevent STING signaling, to impede both NF-kB and TBK1/IRF3 function and repress the expression of the type I IFN promoter and other cytokines and genes.

Example 3: Novel Analogs of Y1 prevent chronic STING activation in TREX1 knockout mice: Human patients with defects in TREX1 suffer from severe forms of systemic lupus erythematosus (SLE), referred to as Aicardi-Goutieres Syndrome (AGS). These disorders are now known to be caused by an inability of the host to degrade self-DNA, which accumulates in the cytosol to activate the STING-sensing pathway and generate chronic, harmful cytokine production. The ability of a STING antagonist to inhibit cytokine production, in vitro, in murine macrophages retrieved from a TREX1-deficient mouse was examined. Compound Y1 can repress cytokine production in TREX1-defective cells as shown in FIG. 6A. Compound Y9 was found to extend the survival of TREX1-deficient mice. Such mice have a median age of approximately 8 weeks before dying through chronic STING-dependent cytokine production which cause enlarged and inflamed hearts. Administration of compound Y9 extended the life of TREX1-deficient mice, compared to mock treated animals (210) as shown in FIG. 6B. Less inflammation in the heart of mice treated with Y9 was observed (see FIG. 6C). Thus, these results indicate that Y9 exhibits the ability to prevent chronic STING activation in cells and mice exhibiting defective TREX1.

Example 4: hTERT-BJ1 Telomerase Fibroblasts (hTERT) were originally purchased from Clontech and were cultured in 4:1 ratio of DMEM:Medium 199 supplement with 10% FBS, 4 mM L-Glutamine and 1 mM sodium pyruvate at 37° C. in a 5% $CO_2$-humidified atmosphere. hTERT-BJ1 Telomerase Fibroblasts stably expressing the luciferase gene under the control of the interferon-beta promoter and SEAP gene under control of the CMV promoter) (hTERT-pIFNβ-Glu) were generated by the Barber laboratory.

MEFs were obtained from E13.5 embryos by a standard procedure. Bone Marrow Derived Macro-phages (BMDM) were isolated from hind-limb femurs of 8-10 weeks old WT and Trex1 KO (TKO) mice. The hematopoietic cells from the bone marrow were cultured in complete DMEM (Invitrogen) including 10 ng/ml of Mouse Recombinant Colony-Stimulating Factor (M-CSF, R&D Systems) for 10 to 14 days.

Example 5: Purification of STING protein for Binding assay: DNA sequence encoding human STING CBD-CTT (152-379) was inserted into pET 26b-6×His-pelB (–) vector between NdeI/XhoI sites (STING152-379H). Protein was expressed in *E. coli* BL21 DE3 RIPL Codon Plus cell. *E. coli* cell was induced by 0.2 mM IPTG, when cell density reached 0.5-0.6 and grew at 10° C. overnight. Cells were spun down and lysed in lysis buffer (20 mM Tris pH7.5, 300 mM NaCl, 5 mM DTT and Protease Inhibitor Cocktail Tablets (Complete EDTA-Free-Roche 11873580001). Protein lysate was French Pressed (10-15 times) using the EmulsiFlex-C3 French Press (Avestin, Inc.), Imidazole was added to a final concentration of 50 mM. Cell debris was removed by centrifugation at 20,000 rpm, 4° C. Supernatant was applied, at a very slow rate, to a 5 ml HisTrap HP columns (GE Healthcare 17-5247-01). Before applying cell lysate, the column was equilibrated with the Lysis Buffer containing 50 mM Imidazole. Column containing the STING Protein was washed extensively using 3 column volumes of Lysis/Binding buffer. Protein was eluted with elution buffer (20 mM Tris pH7.5, 300 mM NaCl, 5 mMDTT, 300 mM Imidazole). Eluted fraction was applied in an S200 SEC Chromatography Column to isolate pure STING Dimer. Fraction containing the 237 amino acid (27 kDA) STING protein (see FIG. 1A, where 140, 142, 144, 146 and 150 indicate transmembrane (TM) 1, TM 2, TM 3, TM 3 and dimerization domain, respectively) as a dimer (see FIG. 1B and FIG. 1C) was pooled, concentrated, and flash frozen for future use.

Human STING c-terminal portion amino acid sequence 152-379 SEQ. ID. 1 MNFNVAHGLA WSYYIGYLRL ILPELQARIR TYNQHYNNLL RGAVSQRLYI LLPLDCGVPD NLSMADPNIR FLDKLPQQTG DHAGIKDRVY SNSIYELLEN GQRAGTCVLE YATPLQTLFA MSQYSQAGFS REDRLEQAKL FCRTLEDILA DAPESQNNCR LIAYQEPADD SSFSLSQEVL RHLRQEEEKEE VTVGSLKTSA VPSTSTMSQE PELLISGMEK PLPLRTDFSL EHHHHHH with a 6×His-Tag tail at the carboxyl end of the sequence.

Example 6: Thermal High Throughput Screen: The denaturation profile of purified STING (STING152-379H) was calibrated using a fluorometer equipped with temperature control (a qPCR apparatus with 320 well capacity). Once this was established, purified STING (5 ul; 1 μM) was mixed with 2.5 ul DMSO and compound (1% DMSO final with 2.5% SYPRO orange. The total reaction mixture was 10 μL in 50 μM HEPES and 100 mM NaCl. SYPRO Orange binds nonspecifically to hydrophobic surfaces. When the protein unfolds, the exposed hydrophobic surfaces bind the dye, resulting in an increase in fluorescence by excluding water. The stability curve and its midpoint value (melting temperature, Tm also known as the temperature of hydrophobic exposure, Th) was obtained by gradually increasing the temperature to unfold the protein and measuring the fluorescence at each point. Curves were measured for STING only and STING+small molecule, and ΔTm was calculated. The temperature ramp was 0.1 Centigrade/second. Approximately 250,000 compounds were screened.

Example 7: Luciferase assay: hTERT-BJ1 Telomerase Fibroblasts stably expressing the luciferase gene under the control of the interferon-beta promoter and SEAP gene under control of the CMV promoter) (hTERT-pIFNβ-Glu) were generated by the Barber laboratory. Luciferase assay was performed using Secrete-Pair Dual Luminescence Assay Kit from GeneCopoeia following the manufacturer's protocol.

Example 8: Immunoblot analysis: Equal amounts of proteins were resolved on sodium dodecyl sulfate (SDS)-Polyacrylamide gels and then transferred to polyvinylidene fluoride (PVDF) membranes (Millipore). After blocking with 5% Blocking Reagent, membranes were incubated with various primary antibodies (and appropriate secondary antibodies). The image was resolved using an enhanced chemiluminescence system ECL (Thermo Scientific) and detected by autoradiography (Kodak). Antibodies: rabbit polyclonal antibody against STING was developed in our laboratory as described previously in Ishikawa et al, 2008; other antibodies were obtained from following sources: β-actin (Sigma Aldrich), p-IRF3 (Cell Signaling), IRF3 (Santa Cruz Biotechnology), p-p65 (Cell Signaling), p65 (Cell Signaling), p-TBK1 (Cell Signaling), TBK1 (Abcam), cGAS (Cell Signaling).

Example 9: Interferon β Elisa analysis: Interferon β Elisa was performed using either the IFNβ human ELISA Kit from Invitrogen or the Human IFNβ ELISA Kit from PBL Interferon Source following the manufacturer's protocol.

Example 10: Immunofluorescence Microscopy: Cells were cultured and treated in their appropriate media on Lab-Tek II chamber slides. Cell were fixed with 4% paraformaldehyde for 15 minutes in at 37° C. and permeabilized with 0.05% Triton X-100 for 5 minutes at room temperature. Immunostaining was performed with rabbit-anti-STING polyclonal, rabbit-anti-IRF3 (Santa Cruz Biotechnology) or rabbit-anti-p65 (Cell Signaling) followed by fluorescence conjugated secondary antibodies (FITC-goat-anti-rabbit) (Invitrogen).

Example 11: qPCR total RNA were reverse-transcribed using M-MLV Reverse Transcriptase (Promega). Real-time PCR was performed using Taqman Gene Expression Assay (Applied Biosystems) for innate immune genes and inflammatory cytokines.

Example 12: Mouse Treatment: Trex1 Hetero knockout mice (Trex1$^{+/-}$) were generated by crossing the hetero mice. Mouse genotypes from tail biopsies were determined using Real Time PCR with specific probes designed for each gene by commercial vendor (Transnetyx). Trex1 KO (TKO) mice (4-5 weeks old) were intraperitoneally injected with 25 μg Z811 per mouse in 200 μL 1% DMSO in PBS. The mice were injected three times a week for 5 months. The survival rates were evaluated.

Example 13: Histopathology. Mice are sacrificed and the heart tissues were fixed in 10% formalin for 48 hours.

Example 14: The stimulation of the immune system to facilitate robust antibody and cytotoxic T cell responses is essential for protecting us against microbial infection and cancers (1). These responses are controlled by cellular innate immune sensors, such as STING, RIG-I/MDA5, or the Toll-Like receptors, which have evolved to detect microbial infection of the cell, predominantly through recognition of pathogen-derived nucleic acids, an event which triggers the transcription of numerous host defense-related proteins including pro-inflammatory cytokines (2, 3). However, it has recently become apparent that the deregulation of these same pathways (chronic activation) can cause a variety of auto inflammatory disease.

Assays were designed and high throughput screens performed to detect small molecule compounds that bound to STING. After screening 250,000 compounds, a family of STING binding and inhibiting molecules were detected. The lead STING antagonist identified was designated Y1. This compound is not rapidly degraded and can be given systemically. Y1 can impede STING-controlled inflammatory cytokine production in murine and human cells. New chemical compounds based on the detected compound Y1 were designed. Unexpectedly, the compounds can be useful in preventing STING-dependent and other forms of chronic innate immune driven disease.

Cytokine overproduction has been known to be involved in the causes of inflammatory disease (16, 20). Many patients exhibit high titer of antinuclear antibody (ANA), circulating DNA or even nucleosomes (18, 19). Self-DNA has therefore been implicated in potentially manifesting these types of diseases, with aberrant innate immune signaling perhaps being caused by a failure to distinguish between self and foreign nucleotides (20). Discovery of the STING-controlled cytosolic DNA-aggravated innate immune pathway subsequently led to investigations into the plausible involvement of this pathway in autoimmune/auto inflammatory disease (2, 5, 20). Several animal models have been found to exhibit inflammatory diseases. For example, mice deficient in deoxiribonucleases I (DNaseI) manifest inflammatory autoimmune symptoms such as immune complex nephritis (22). More severely, mice lacking macrophage lysosomal DNA endonuclease DNase II, die before birth due to the toxic effects of type I IFN overproduction (23). DNaseIII (also called TREX1) deficient mice exhibit inflammation related disease and have a mean life span of 2 months (17). Human patients with defects in DNases such as TREX1 suffer from sever forms of systemic lupus erythematosus (SLE), referred to as Aicardi-Goutieres Syndrome (AGS) (18, 24). These disorders are now known to be caused by an inability of the host to degrade self-DNA, which accumulates to activate the STING-sensing pathway and generate chronic, harmful cytokine production. Indeed, mice lacking DNaseII or III are completely viable when crossed on a STING-deficient background (12,13). STING has also been shown to influence inflammation driven cancer and inflammatory bowel disease (IBD) (21, 25, U.S. patent application Ser. No. 16/284,975 entitled CANCER TREATMENT AND DIAGNOSIS inventor Glen N. Barber, filed Feb. 25, 2019 which is herein incorporated by reference in its entirety and for all purposes). Finally, mutations in the STING gene itself, which renders STING-constitutively active has been described in patients with STING-associated vasculopathy with onset in infancy (SAVI) (a systemic inflammation and violaceous, scaling lesions of fingers, toes, nose, cheeks, and ears) (26). Collectively, the STING pathway may provide a new target that could plausibly be controlled, therapeutically, to help prevent a wide variety of inflammatory diseases in humans. The unexpected discovery of a small molecule and novel analogues (Y1) that bind to and inhibit STING function that could be useful in treating chronic STING-related auto inflammatory disease.

Two novel STING-based assays are used in high throughput screens. Using these assays, a compound that binds to and inhibits STING-specific signaling can be identified. Based on the structure, chemistry has been developed to generate a novel series of STING antagonists. A lead compound, designated Y1 has been selected for further evaluation, for the prevention of inflammatory disease. The lead compound Y1 binds to and stabilizes STING and can be given systemically. The compound is human and mouse specific and demonstrates that Y1 can prevent AGS, in vivo (survival was significantly improved over several months). Unexpectedly, a novel STING antagonist that exhibits anti-inflammatory activity, can be useful for the treatment of a variety of auto inflammatory disorders.

Development of novel STING activating compounds: Purified STING protein was used as bait to identify binding compounds, using a thermal shift assay (TSA). Out of 250,000 screened compounds, achieved using Enamine libraries, several STING binding small molecules were examined for their ability to inhibit STING signaling. In the presence of cytosolic DNA species, STING becomes activated to drive the transcription of cytokines such as type I IFN. Compounds binding to STING via TSA were subsequently examined for their ability prevent cytosolic DNA species from activating the type I interferon (IFN) promoter, using a live cell assay. This assay comprised immortalized human fibroblasts (hTERT) that were stably transfected with the type I IFN promoter driving luciferase as well as the CMV promoter driving SEAP (hTERT-pIFNβ-Glu). The live cell assay was developed by the Barber lab and has been patented. The ability of the small molecules to prevent activation of the type I IFN promoter and the transcription of luciferase, but not SEAP in response to cytosolic DNA species, was assessed. The activation of STING, typically by CDNs, in turn activates the transcription factors NF-κB and IRF3, both of which are required to induce the transcriptional stimulation of the Type I IFN promoter, but not the CMV promoter (IRF3 and NF-kB transcription factor binding sites are not contained in the CMV promoter)(7, 27). Thus, should STING activation be inhibited by a small molecule identified in the first screen (HTS), the level of luciferase should decrease in response to transfection of cytosolic DNA.

Compound Y1 inhibit both human and mouse STING function: Compound Y1 from the first screen (HT STING binding assay) exhibited inhibition of the activation of the type I IFN promoter in hTERT-pIFNβ-Glu in response to the presence of cytosolic DNA (referred to as ISD treatment) (FIG. 2A). To confirm this, the compounds were administered onto normal hTERT cells and their ability to prevent cytosolic DNA from activating STING was assessed (FIG. 2B-FIG. 2E). This was achieved by examining whether Y1 compound inhibited Type I IFN production using ELISA assay and quantitative real time PCR. The data showed that compound Y1 dramatically decreased IFNβ expression and production in hTERT cells (FIG. 2B-FIG. 2C). In addition, the compounds prevented STING phosphorylation (STING is phosphorylated following activation) and the subsequent phosphorylation of TBK1, the kinase of IRF3. Phosphorylation of TBK1 and IRF3 are required for activation of the type I IFN promoter. This data indicated that compound Y1 robustly prevented STING phosphorylation and subsequently TBK1 and IRF3 phosphorylation (FIG. 2D). Compound Y1 reproducibly prevented STING activity, effectively preventing STING trafficking which is a requirement for STING function, STING phosphorylation, as well as TBK1 and IRF3 phosphorylation (FIG. 2E). Thus, Y1 can bind to STING and impede STING function, in human cells.

MEFs were treated with the compound Y1 and then treated them with cytosolic DNA (220). The production of STING-inducible cytokines Cxcl10 and Cxcl5, IFNβ in response to ISD were dramatically decreased in the presence of Y1 in MEFs (FIG. 2F-FIG. 22H). The compounds also prevented the phosphorylation of TBK1 or IRF3 and translocation of NF-kB (p65) or IRF3 in response to cytosolic DNA stimulation (FIG. 21-FIG. 2J). The data thus demonstrates that Y1 bind to and inhibit STING activity, which prevents the activation of both IRF3 and NF-kB which are required for type I IFN and other cytokine gene induction in murine cells as well as human cells.

ANALOGS OF Y1: Based on the structure of Y1, approximately 500 similarly structured compounds from the Enamine stock collection were retrieved and tested for their ability to bind to STING in TSA. Approximately 43 exhibited the ability to associate with STING as determined by TSA. All compounds were tested for their ability to prevent Interferon Stimulation by DNA (ISD, 220), that is the ability of cytosolic DNA (220) to activate STING signaling and the transcription of the type I IFN promoter, driving luciferase in (hTERT-pIFNβ-Glu) (which requires both IRF3 and NF-kB). Fourteen (14) compounds were able to prevent cytosolic DNA-dependent activation of STING signaling. Based on the structures of the 14 compounds, 25 novel analogs, not in the public domain, were chemically synthesized using standard chemistry procedures.

These novel compounds were tested for their ability to prevent STING function which activates the type I IFN promoter in human cells. Of the 25 novel analogs, the lead STING antagonist (Y1) generated 8 compounds which were found to meet the criteria to inhibit STING dependent signaling and showed the most effective inhibitory activity (Y2, Y3, Y4, Y5, Y6, Y7, Y8 and Y9, see Table I). To confirm the inhibitory effects of Y1, the study in hTERT-pIFNβ-Glu cells was carried out at various doses. hTERT-pIFNβ-Glu cells were treated with Y1 and subsequently the cells were transfected with cytosolic DNA which activates STING signaling. This assay verified that Y1 at 50 μM (490) or 25 μM (492) concentrations showed robust inhibitory activity of the type I IFN promoter in hTERT-pIFNβ-Glu in response to the presence of ISD (see FIG. 7A). Further, Y1 was able to prevent STING activation and the downstream activation of STING. In normal hTERT cells were treated with Y1 and stimulated with ISD. The production of STING-inducible cytokines Cxcl10 was robustly inhibited in the presence of Y1 at 50 μM (490), 25 μM (492) or 5 μM (494) concentrations (see FIG. 7B). In addition, Y1 was able to prevent the phosphorylation of STING, TBK1 and IRF3 at 50 μM (490) or 25 μM (492) concentrations (see FIG. 7C) as well as STING trafficking and translocation of IRF-3 (see FIG. 7D). Further, MEFs were treated with Y1 at 50 μM (490) or 25 μM (492) concentrations and then stimulated with cytoplasmic DNA (220) and Cxcl10 expression examined by qPCR and STING-dependent phosphorylation of TBK1 and IRF3 (see FIG. 7E and FIG. 7F). These observations were corroborated by observing that Y9 potently prevented the translocation of p65 (FIG. 7G). Collectively, our data indicates the Y1, Y2, Y3, Y4, Y5, Y6, Y7, Y8 and Y9 can prevent STING signaling, to impede both NF-kB and TBK1/IRF3 function and repress the expression of the type I IFN promoter and other cytokines and genes in murine cells as well as human cells.

Inflammatory Diseases Induced by STING Dependent Signaling:

Several animal models have been found to exhibit inflammatory diseases. For example, DNaseIII (also called TREX1) deficient mice (TKO) (see FIG. 8A) exhibit inflammation related disease and have a mean life span of 2 months. Further, TKO mice show enlarged and inflamed hearts. However, mice lacking TREX1 are completely viable when crossed on a STING-deficient background (administration of Y9, see FIG. 8A). Microarray analysis and qPCR analysis of heart tissue indicated the presence of high levels of pro inflammatory cytokines, such as TNF-α and IL-1β, in TKO mice compared with WT mice. RNA representing these cytokines was dramatically reduced in the hearts of STKO mice, confirming that their production was indeed STING-dependent (see FIG. 8B-FIG. 8E).

STING also plays an important role in facilitating inflammatory disease in a murine model using IL10-knockout mice (IL10KO). IL10 is a key anti-inflammatory cytokine. Mice deficient in IL-10 can develop severe enterocolitis, resembling Crohn's disease (see FIG. 9A). The importance of STING in the development of IL-10-controlled colitis and polyp formation was examined. IL-10−/−STING−/− double-deficient mice (IL10KO/SKO) (879) were generated and the IL-10−/− mice (IL10KO)(878) developed severe colitis within 10 weeks, while IL10KO/SKO mice (879) did not exhibit any significant intestinal inflammatory disease for over 19 weeks (FIG. 9A). The pronounced thickening of the bowel wall and slightly shortened colon length characteristic for IL-10-deficient mice was also reduced in IL10KO/SKO mice (FIG. 9A). The incidence of spontaneous polyp formation in IL-10-deficient mice was also completely eliminated in the absence of STING (FIG. 9B-FIG. 9D). Gene expression profiles were measured on the various mice, using quantitative analysis, which indicated that high levels of pro-inflammatory cytokine production including IL-1β, IL-22, and IL-12 was detected in the colon of IL10KO mice, were similarly greatly repressed in the absence of STING signaling (FIG. 9E-FIG. 9G).

Given these unexpected results, it is plausible to consider that STING signaling plays an important role in facilitating such inflammatory diseases. Therefore, the novel STING antagonists be useful in preventing STING-dependent and other forms of chronic innate immune driven disease.

Evaluating the safety of Y1 as an anti-inflammatory agent: Preliminary toxicity studies for Y1 have been undertaken. The data indicates that Y1 exhibited no toxicity in Balb/c mice when administered orally (5, 50, 300 and 2000 mg/kg in Cremophor EL-saline [20%80%, v/v). Survival was 100%. No clinical signs of toxicity, body weight changes, biochemical abnormalities (ASAT, ALAT, ALAP, CK, LDL, creatine) or overt immunology were observed.

Determining the safety of Y1 at various doses via different routes of inoculation: The goal of this study will be evaluated general acute toxicity of compound Y1 with a particular investigation of hematological and clinical blood parameters and necropsy. The study will be performed in sex matched C57/BL6 mice (n=7 per each group) will be dosed at three different concentration (1 mg/kg, 10 mg/kg, 100 mg/kg) via three different routes (intraperitoneally (I.P.), intravenously (I.V.), and orally (PO) twice a week for 3 months. Y1 will be solubilized in the formulation 0.1 mg/ml, 1 mg/ml, 10 mg/ml in 1% DMSO/PBS (v/v) for I.P. or I.V. injections. For peroral (PO) route of drug administration, Y1 will be solubilized in Cremophor EL-saline (20%: 80%, v/v). All mice will be observed for mortality and signs of gross toxicity at 30 min, 2, 4 and 6 hours after each administration and thereafter daily for 2 months. Toxic effects of the compound will be evaluated during the course of the study by visual observations according to the standard procedures. External state of skin and fur, eyes and mucous membranes, as well as the respiratory system, blood circulation, peripheral and central nervous systems, changes in locomotor activity will be evaluated. The presence of tremor, seizures, salivation, diarrhea, apathy will be taken into account as well. Body weights and calculation of mean body weight/group can be performed every other day. Necropsy with macroscopic inspection, body weight changes (BWC) in relation to the initial body mass, hematological and clinical chemistry parameters analysis can be performed on the terminal day of the study. The main hematological parameters (WBC, RBC, PLT number and HGB concentration) can be assessed. The number of lymphocytes (LYM), monocytes (MON), eosinophils (EOS), stab and segmented granulocytes (GRAN) will be also counted separately. Aspartate transferase (ASAT), Alanine aminotransferase (ALAT), Alkaline phosphatase (ALP), Creatine kinase (CK), Lactate dehydrogenase (LD), creatinine, urea, and total protein will be determined. The different route could show a different level of safety. For example, I.V. injection at high dose (100 mg/kg) might generate some toxic signs but PO administration might not show much toxicity at high dose (100 mg/kg).

Evaluating the efficacy of Y1 in Trex1 dependent inflammatory disease model: Mice lacking Trex1 similarly die at an early age through comparable symptoms, including inflammatory myocarditis, through chronic activation of the stimulator of IFN genes (STING) pathway (13, 17). It has been demonstrated that monocytes such as macrophages or dendritic cells rather than myocytes are predominantly responsible for causing inflammation in STING dependent manner. Trex deficient macrophages (TKO) appeared chronically stimulated by abnormal genomic DNA (13). Does Y1 inhibit STING dependent inflammatory cytokines in TKO monocytes and further prevent Trex1 dependent myocarditis and eventually increase the survival rates in TKO mice?

Determining the effect of Y1 in preventing pro inflammatory cytokines in Trex1 deficient monocytes: Compound Y1 was administered in the TKO macrophages. The data showed that Cxcl10 expression was dramatically decreased in Y1 treated TKO macrophages compared to DMSO control treated. To further evaluate this, peritoneal macrophages and PBMCs from TKO mice as well as bone marrow derived macrophages or dendritic cells will be isolated and treat the primarily cultured cells with Y1 at 10 μM, 25 μM and 50 μM for 24 hours and perform DNA microarray analysis and quantitative real time PCR to confirm that Y1 inhibit the innate immune related gene and pro inflammatory genes, compare to vehicle (0.5% DMSO/PBS) treated TKO cells. TREX1-deficient monocytes generate higher background levels of STING-dependent pro inflammatory cytokines but the novel STING antagonist Y1 treated TKO cells prevent the cytokine production.

Determining the efficacy of Y1 in Trex1 deficient mice via different routes of inoculation: The objective is to evaluate whether Y1 can prevent Trex1 dependent inflammatory disease in vivo. Preliminarily, Y1 can extend the survival of TKO mice. The results showed that treatment of mice with Y1 extended the life of TREX1-deficient mice, compared to mock treated TKO mice (FIG. 6B). Less inflammation in the heart of mice treated with Y1 (FIG. 6C). Thus, these results indicate that Y1 exhibits the ability to prevent chronic STING activation in cells and mice exhibiting defective TREX1. To extend this analysis, TKO mice will be given effectively via different routes and concentrations to determine the optimized doses without toxicity via different route (intraperitoneally (I.P.), intravenously (I.V.), and orally (PO)). The study will be performed in 4 weeks old sex matched wild type C57/BL6 (WT) mice (n=7 per each group) and $C_{57}$/BL6 background Trex1−/− mice (TKO). WT and TKO mice will be treated with Y1 at one dose via I.P., I.V. or PO twice a week for 3 months. 1% DMSO/PBA (v/v) will be used as a control. At 3 months after the first treatment, all mice are euthanized to analyze heart inflammation, inflammatory cytokines in heart and serum. To analyze histopathology, the heart tissues well be fixed in 10% formalin for 48 hour and all processes for paraffin block and H&E staining will be performed at The Pathology Research Resources Histology Laboratory. To evaluate inflammatory cytokine expression, RNA from the organoids treated with carcinogens or DNA damage drug described above are isolated and cDNA generated by reverse transcriptase to perform qPCR. Pro-inflammatory or anti-inflammatory cytokines such as IL1β, IL-18, IL22, and IL-10 as well as innate immune related cytokines such as IFNβ, Cxcl10, Cxcl5, and Ifits using specific Taqman probes (Applied Biosystems) will be analyzed. Microarray Analysis in the total RNA isolated will be performed. Microarray analysis will be performed using Affymetrix Mouse Gene array (2.0 ST Array). The survival rates of TKO mice will be determined for the Y1 treated group. Same as above, WT and TKO mice will be treated with Y1 at one dose via I.P., I.V. or PO twice a week for 3 months (n=7 per each group). Survival rates of Y1 treated TKO mice will be monitored for 6-7 months and the survival curve using Kaplan-Meier survival curve will be analyzed. All mice will be observed for signs of gross toxicity, body weights as well as mortality.

Evaluating the efficacy of Y1 in IL-10 dependent colitis model: A key question is whether Y1 will work against other types of inflammatory disease? STING plays an important role in facilitating colitis in IL10-knockout mice (IL10KO) (21). While mice deficient in IL-10 can develop severe enterocolitis, resembling Crohn's disease, IL10KO/SKO mice did not exhibit any significant intestinal inflammatory disease for over 19 weeks (FIG. 9A). Therefore, can Y1 exert anti-colitis activity by directly inhibiting STING dependent inflammatory cytokines? To evaluate the efficacy of Y1 in preventing IL-10 dependent colitis, similar experiments with TKO mice model can be performed. Sex matched, 4 weeks old wild type C57/BL6 (WT) mice (n=7 per each group) and C57/BL6 background IL10$^{-/-}$ mice (IL10KO). WT and IL10KO mice will be treated with Y1 at one dose via I.P., I.V. or PO twice a week for 3 months. 1% DMSO/PBA (v/v) will be used as a control. At 3 months after the first treatment, all mice are euthanized to analyze colon histology and inflammatory cytokines in colon and serum as well as toxicity at the end of the experiments.

Preliminary data indicates that our novel STING antagonists Y1 and Y9 exhibit the ability to prevent chronic STING activation in cells and mice exhibiting defective TREX1, see FIG. 6. The novel STING antagonists Y1 and Y9, may exhibit the effects inhibiting graft versus host disease.

Example 16: All statistical analysis was performed by Student's t test. The data were considered to be significantly different when P<0.05.

Embodiments contemplated herein further include Embodiments S1-S6 following.

Embodiment S1. A method for treating a human subject with an antagonist of a stimulator of interferon genes (STING) protein, wherein the human subject is suffering from a disease, the method comprising the steps of determining whether a human subject has a defective functional activity of STING protein by isolating a sample from the human subject having the disease, performing a PCR assay on the sample to determine a functional activity of STING protein in a cell population, if the human subject has an upregulated defective functional activity of STING, then identifying a selected antagonist therapy and treating the human subject in vivo with the selected antagonist therapy.

Embodiment S2. The method of embodiment S1, where the antagonist therapy comprises a therapeutically effective amount of the compound of Formula I Formula I

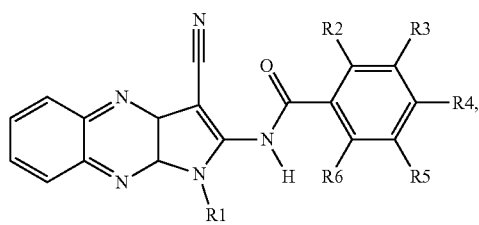

or a pharmaceutically acceptable salt, hydrate, ester, solvate, prodrug, stereoisomer, or tautomer thereof, where $R_1$ is —($C_1$-$C_6$) alkyl-($C_3$-$C_6$) cycloalkenyl, —($C_1$-$C_6$) alkyl-($C_3$-$C_6$) cycloalkyl, —($C_1$-$C_6$) alkyl-($C_3$-$C_6$) substituted cycloalkenyl, —($C_1$-$C_6$) alkoxy-($C_3$-$C_6$) cycloalkenyl, —($C_2$-$C_6$) alkenyl-($C_3$-$C_6$) cycloalkenyl, where $R_2$, $R_3$, $R_4$, $R_5$ and $R_6$ are independently selected from the group consisting of —H, -halogen, —($C_1$-$C_6$) alkyl, —($C_3$-$C_6$) cycloalkyl, —($C_1$-$C_6$) haloalkyl, —($C_1$-$C_6$) alkoxy, —($C_1$-$C_6$)haloalkoxy, —($C_2$-$C_6$) alkenyl, —($C_2$-$C_6$) alkynyl, -nitro, —CN, —OH, —COOH, —SH, —NH$_2$, —NH($C_1$-$C_4$) alkyl, and —N(($C_1$-$C_4$) alkyl)$_2$, where $R_7$ is the atom selected from the group consisting of selenium and oxygen.

Embodiment S3. The method of embodiment S1, where the antagonist therapy comprises a therapeutically effective amount of the compound of Formula II Formula II or a pharmaceutically acceptable salt, hydrate, ester, solvate, prodrug, stereoisomer, or tautomer thereof, where $R_2$, $R_3$, $R_4$, $R_5$ and $R_6$ are independently selected from the group consisting of —H, -halogen, —($C_1$-$C_6$) alkyl, —($C_3$-$C_6$) cycloalkyl, —($C_1$-$C_6$) haloalkyl, —($C_1$-$C_6$) alkoxy, —($C_1$-$C_6$) haloalkoxy, —($C_2$-$C_6$) alkenyl, —($C_2$-$C_6$) alkynyl, -nitro, —CN, —OH, —COOH, —SH, —NH$_2$, —NH($C_1$-$C_4$) alkyl, and —N(($C_1$-$C_4$) alkyl)$_2$.

Embodiment S4. The method of embodiment S1, where the antagonist therapy comprises a therapeutically effective amount of the compound of Formula I Formula III or a pharmaceutically acceptable salt, hydrate, solvate, prodrug, stereoisomer, or tautomer thereof, where $R_2$ is -halogen, and where $R_3$ and $R_5$ are as follows: where $R_3$ or $R_5$ is —H then $R_5$ or $R_3$ is -halogen; where $R_3$ or $R_5$ is —H then $R_5$ or $R_3$ is —($C_1$-$C_6$) alkyl; and where $R_3$ or $R_5$ is -halogen then $R_5$ or $R_3$ is —($C_1$-$C_6$) alkyl.

Embodiment S5. The method of embodiment S1, where the disease is caused by or associated with a STING protein expression, activity, and/or function.

Embodiment S6. The method of embodiment S1, where the disease is caused by or associated with upregulation of one or more of the intracellular pathways in which a STING protein is involved.

Synthesis (420): 2-amino-1-benzyl-1H-pyrrolo[2,3-b]quinoxaline-3-carbonitrile

Sodium hydride (0.2 g, 2 equiv, 10.06 mmol) was added to a solution of malononitrile (0.7 g, 2 equiv, 10.06 mmol) in anhydrous dioxane (30 mL) and the mixture was stirred at room temperature for 30 min. 2,3-Dichloroquinoxaline (1 g, 1 equiv, 5.03 mmol) was added to the obtained suspension and the resulted mixture was stirred at room temperature for 3 h and then at 100° C. for 1 h. After cooling to room temperature the solvent was evaporated under reduced pressure and water (100 mL) was added to the residue. The mixture was extracted with dichloromethane (3×30 mL). The organic layers were combined, washed with brine (2×30 mL), dried over sodium sulfate and concentrated under reduced pressure to dryness. The obtained residue was added to benzylamine (1.13 g, 2 equiv, 10.06 mmol) solution in DMSO (30 mL) and the mixture was heated at 120° C. for 16 h. After cooling to room temperature the mixture was poured into water (150 mL), the precipitate was collected by filtration, washed with water (2×50 mL) and dried on air to afford 2-amino-1-benzyl-1H-pyrrolo[2,3-b]quinoxaline-3-carbonitrile (Intermediate 1, 1.07 g) as a white solid which was used without further purification. LCMS: 300.2 m/z $[M+H]^+$.

The intermediates (430, 440, 450 and 460) were prepared according to the procedure described for 420 from the starting materials indicated in the Table II.

TABLE II

| Compound code | Name and structure | LCMS m/z | Starting materials |
|---|---|---|---|
| 430 | 2-amino-1-phenethyl-1H-pyrrolo[2,3-b]quinoxaline-3-carbonitrile 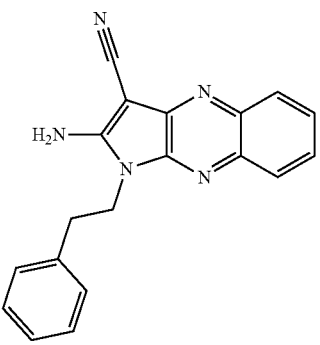 [SMILES: N#Cc1c(N)n(CCc2ccccc2)c2nc3ccccc3nc12] | 314.2 $[M + H]^+$ | 2-(3-chloroquinoxalin-2-yl)malononitrile; 2-phenylethan-1-amine |
| 440 | 2-amino-1-(2-phenoxyethyl)-1H-pyrrolo[2,3-b]quinoxaline-3-carbonitrile 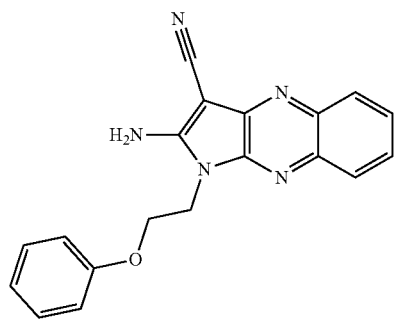 [SMILES: N#Cc1c(N)n(CCOc2ccccc2)c2nc3ccccc3nc12] | 330.2 $[M + H]^+$ | 2-(3-chloroquinoxalin-2-yl)malononitrile; 2-phenoxyethan-1-amine |

TABLE II-continued

| Compound code | Name and structure | LCMS m/z | Starting materials |
|---|---|---|---|
| 450 | 2-amino-1-(2-methoxyethyl)-1H-pyrrolo[2,3-b]quinoxaline-3-carbonitrile | 268.2 [M + H]⁺ | 2-(3-chloroquinoxalin-2-yl)malononitrile; 2-methoxyethan-1-amine |
| 460 | 2-amino-1-(3-fluorophenethyl)-1H-pyrrolo[2,3-b]quinoxaline-3-carbonitrile | 332.2 [M + H]⁺ | 2-(3-chloroquinoxalin-2-yl)malononitrile; 2-(3-fluorophenyl)ethan-1-amine |

Compound Y1: N-(1-benzyl-3-cyano-1H-pyrrolo[2,3-b]quinoxalin-2-yl)-2-chlorobenzamide.

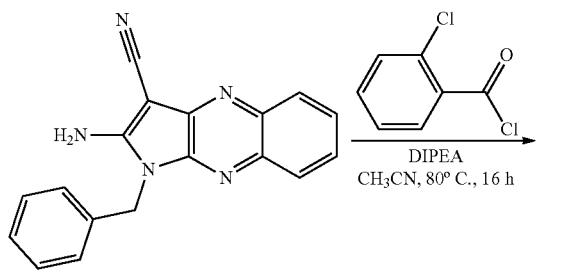

2-Amino-1-benzyl-1H-pyrrolo[2,3-b]quinoxaline-3-carbonitrile (420) (0.1 g, 1 equiv, 0.33 mmol), 2-chlorobenzoyl chloride (0.116 g, 2 equiv, 0.66 mmol) and N-ethyl-N-isopropylpropan-2-amine (0.085 g, 2 equiv, 0.66 mmol) were mixed in acetonitrile (20 mL) and the mixture was heated at 80° C. for 16 h. After cooling to room temperature the solvent was evaporated under reduced pressure and the residue was purified by reverse phase HPLC (water/methanol, 2-8 min 0-65%, 30 mL/min, column: SunFire 100*19 mm) to give N-(1-benzyl-3-cyano-1H-pyrrolo[2,3-b]quinoxalin-2-yl)-2-chlorobenzamide (0.042 g) as a yellow solid. ¹H NMR (400 MHz, DMSO-d₆), δ, ppm: 12.10 (s, 1H), 8.20-8.31 (m, 1H), 8.11-8.23 (m, 1H), 7.80-7.84 (m, 2H), 7.55-7.62 (m, 2H), 7.48 (t, 1H), 7.26-7.40 (m, 4H), 7.16 (d, 2H), 5.75 (s, 2H). LCMS: m/z 438.0 [M+H]⁺.

Compounds Y2-Y9 were prepared according to the procedure described for compound Y1, where intermediate 430, 440, 450, 460, 470, 480, 490, 500, 510, 520, 530 and 540 were substituted for intermediate 420 to generate compounds Y4, Y6, Y1, V5, Y8, Y9, Y2, Y3 and Y7 respectively. The compound code, name, structure, starting materials, and characterization data are as indicated in the Table III

TABLE III

| Compound code | Name, structure and starting materials | Characterization data |
|---|---|---|
| Y4 | 2-chloro-N-(3-cyano-1-phenethyl-1H-pyrrolo[2,3-b]quinoxalin-2-yl)-5-methylbenzamide<br>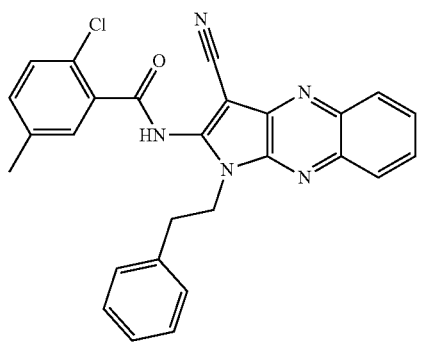 [SMILES: Cc1ccc(Cl)c(C(=O)Nc2c(C#N)c3nc4ccccc4nc3n2CCc2ccccc2)c1]<br>470;<br>2-chloro-5-methylbenzoyl chloride | $^1$H NMR (400 MHz, DMSO-d$_6$), δ, ppm: 11.95 (s, 1H), 8.19-8.30 (m, 1H), 8.09-8.22 (m, 1H), 7.71-7.81 (m, 2H), 7.05 (d, 1H), 7.36-7.45 (m, 2H), 7.05-7.22 (m, 5H), 4.63 (t, 2H), 3.12 (t, 2H), 2.37 (s, 3H).<br>LCMS: m/z 466.2 [M + H]$^+$ |
| Y6 | 2-chloro-N-(3-cyano-1-phenethyl-1H-pyrrolo[2,3-b]quinoxalin-2-yl)-6-fluorobenzamide<br>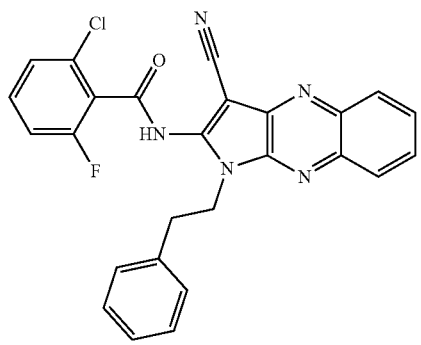 [SMILES: N#Cc1c(NC(=O)c2c(F)cccc2Cl)n(CCc2ccccc2)c2nc3ccccc3nc12]<br>480;<br>2-chloro-6-fluorobenzoyl chloride | $^1$H NMR (400 MHz, DMSO-d$_6$), δ, ppm:<br>LCMS: m/z 470.0 [M + H]$^+$ |
| Y5 | 2-chloro-N-(3-cyano-1-phenethyl-1H-pyrrolo[2,3-b]quinoxalin-2-yl)-3-fluorobenzamide<br>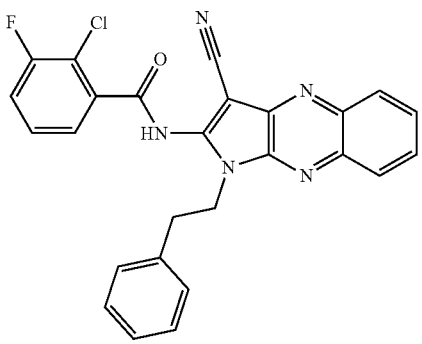 [SMILES: N#Cc1c(NC(=O)c2cccc(F)c2Cl)n(CCc2ccccc2)c2nc3ccccc3nc12]<br>490;<br>2-chloro-3-fluorobenzoyl chloride | $^1$H NMR (400 MHz, DMSO-d$_6$), δ, ppm: 12.12 (s, 1H), 8.17-8.20 (m, 1H), 8.07-8.15 (m, 1H), 7.74-7.83 (m, 2H), 7.61-7.72 (m, 2H), 7.55 (d, 1H), 7.07-7.23 (m, 5H), 4.68 (t, 2H), 3.16 (t, 2H).<br>LCMS: m/z 470.0 [M + H]$^+$ |

TABLE III-continued

| Compound code | Name, structure and starting materials | Characterization data |
|---|---|---|
| Y8 | 2,3-dichloro-N-(3-cyano-1-phenethyl-1H-pyrrolo[2,3-b]quinoxalin-2-yl)benzamide<br>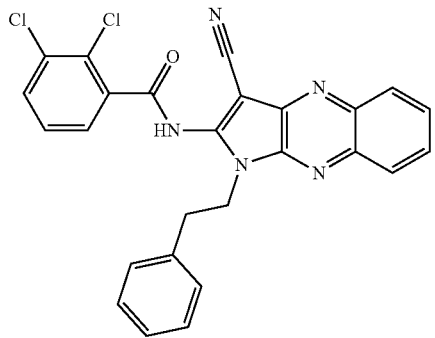 [SMILES: N#Cc1c(NC(=O)c2cccc(Cl)c2Cl)n(CCc2ccccc2)c2nc3ccccc3nc12]<br>500;<br>2,3-dichlorobenzoyl chloride | $^1$H NMR (400 MHz, DMSO-d$_6$), δ, ppm:<br>LCMS: m/z 486.0 [M + H]$^+$ |
| Y9 | 2-chloro-N-(3-cyano-1-phenethyl-1H-pyrrolo[2,3-b]quinoxalin-2-yl)-3-methylbenzamide<br>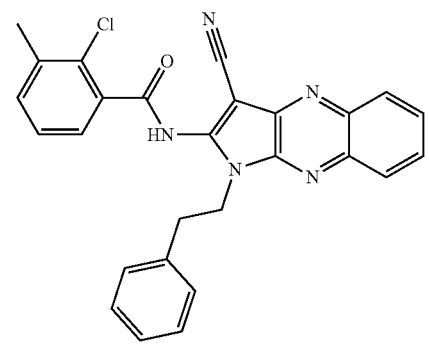 [SMILES: Cc1cccc(C(=O)Nc2c(C#N)c3nc4ccccc4nc3n2CCc2ccccc2)c1Cl]<br>510;<br>2-chloro-3-methylbenzoyl chloride | $^1$H NMR (400 MHz, DMSO-d$_6$), δ, ppm: 12.13 (s, 1H), 8.19-8.23 (m, 1H), 8.05-8.11 (m, 1H), 7.75-7.81 (m, 2H), 7.58-7.69 (m, 1H), 7.48 (d, 2H), 7.08-7.25 (m, 5H), 4.69 (t, 2H), 3.15 (t, 2H), 2.41 (s, 3H)<br>LCMS: m/z 466.0 [M + H]$^+$ |
| Y2 | 2-chloro-N-(3-cyano-1-(2-phenoxyethyl)-1H-pyrrolo[2,3-b]quinoxalin-2-yl)benzamide<br>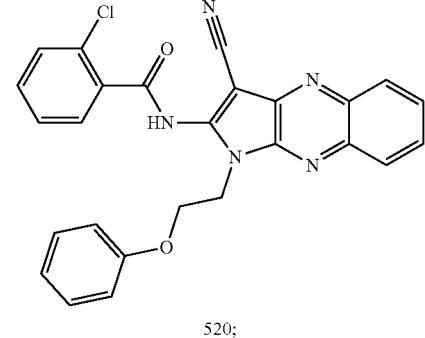<br>520;<br>2-chlorobenzoyl chloride | $^1$H NMR (400 MHz, DMSO-d$_6$), δ, ppm:<br>LCMS: m/z 468.0 [M + H]$^+$ |

TABLE III-continued

| Compound code | Name, structure and starting materials | Characterization data |
|---|---|---|
| Y3 | 2-chloro-N-(3-cyano-1-(2-methoxyethyl)-1H-pyrrolo[2,3-b]quinoxalin-2-yl)benzamide<br>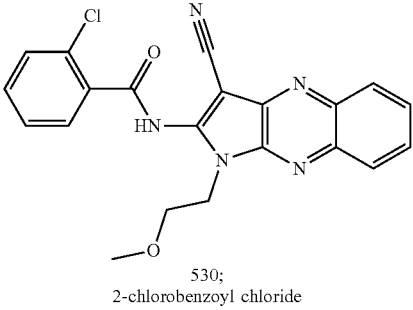<br>530;<br>2-chlorobenzoyl chloride | $^1$H NMR (400 MHz, DMSO-$d_6$), δ, ppm: 11.88 (s, 1H), 8.22-8.25 (m, 1H), 8.10-8.13 (m, 1H), 7.78-7.86 (m, 2H), 7.75 (d, 1H), 7.48 (d, 1H), 7.57-7.68 (m, 3H), 4.68 (t, 2H), 3.76 (t, 2H), 3.19 (s, 3H)<br>LCMS: m/z 406.2 [M + H]$^+$ |
| Y7 | 2-chloro-N-(3-cyano-1-(3-fluorophenethyl)-1H-pyrrolo[2,3-b]quinoxalin-2-yl)benzamide<br>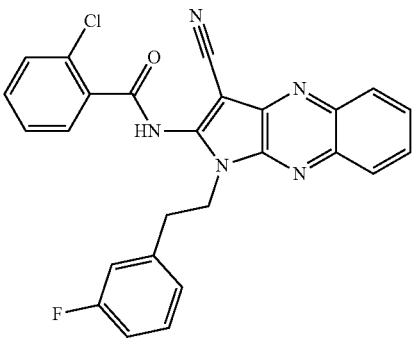 [SMILES: N#Cc1c(NC(=O)c2ccccc2Cl)n(CCc2cccc(F)c2)c2nc3ccccc3nc12]<br>540;<br>2-chlorobenzoyl chloride | $^1$H NMR (400 MHz, DMSO-$d_6$), δ, ppm:<br>LCMS: m/z 470.0 [M + H]$^+$ |

EQUIVALENTS

Those skilled in the art will recognize, or be able to ascertain using no more than routine experimentation, many equivalents to the specific embodiments and methods described herein. Such equivalents are intended to be encompassed by the scope of the present application. All patents, patent applications, and literature references cited herein are hereby expressly incorporated by reference.

Example embodiments of the methods, systems, and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. For example, it is envisaged that, irrespective of the actual shape depicted in the various Figures and embodiments described above, the outer diameter exit of the inlet tube can be tapered or non-tapered and the outer diameter entrance of the outlet tube can be tapered or non-tapered.

Thus, the breadth and scope of the present invention should not be limited by any of the above-described exemplary embodiments, but should be defined only in accordance with the following claims and their equivalents.

The invention claimed is:

1. A method of inhibiting a functional activity of a STING protein (STimulator of INterferon Genes protein) in a human subject suffering from a disease and in need thereof, comprising:
   (a) determining whether the human subject has an upregulated functional activity of STING protein, comprising:
      isolating a biological sample from the human subject having the disease;
      performing an assay on the biological sample to determine the functional activity of the STING protein;
   (b) if the human subject has an upregulated functional activity of the STING protein;
      then selecting a compound to inhibit the functional activity of the STING protein, where the compound has formula I:

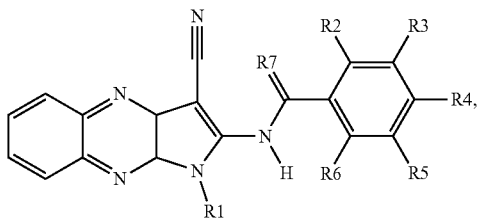

or a pharmaceutically acceptable salt, hydrate, ester, solvate, stereoisomer, or tautomer thereof, where $R_1$ is —($C_2$-$C_6$) alkyl-($C_3$-$C_6$) cycloalkenyl, —($C_1$-$C_6$) alkyl-($C_3$-$C_6$) cycloalkyl, —($C_1$-$C_6$) alkyl-($C_3$-$C_6$) substituted cycloalkenyl, —($C_1$-$C_6$) alkoxy-($C_3$-$C_6$) cycloalkenyl, —($C_2$-$C_6$) alkenyl-($C_3$-$C_6$) cycloalkenyl, where $R_2$, $R_3$, $R_4$, $R_5$ and $R_6$ are independently selected from the group consisting of —H, -halogen, —($C_1$-$C_6$) alkyl, —($C_3$-$C_6$) cycloalkyl, —($C_1$-$C_6$) haloalkyl, —($C_1$-$C_6$) alkoxy, —($C_1$-$C_6$) haloalkoxy, —($C_2$-$C_6$) alkenyl, —($C_2$-$C_6$) alkynyl, -nitro, —CN, —OH, —COOH, —SH, —$NH_2$, —NH($C_1$-$C_4$) alkyl, and —N(($C_1$-$C_4$) alkyl)$_2$, where $R_7$ is an atom selected from the group consisting of selenium and oxygen; and
      administering the compound to the human subject suffering from the disease to inhibit the functional activity of the STING protein in the human subject.

2. The method of claim 1, where the biological sample is selected from the group consisting of tissue, blood, saliva, urine, feces, semen, tears, other body fluids and extracts thereof.

3. The method of claim 1, where the disease is systemic lupus erythamatosis.

4. The method of claim 1, where the STING protein is down regulated by the compound.

5. The method of claim 1, where the compound is 2-chloro-N-[3-cyano-1-(2-phenylethyl)-1H-pyrrolo[2,3-$] quinoxalin-2-yl]-3-methylbenzamide.

6. The method of claim 5, where the disease is systemic lupus erythamatosis.

7. The method of claim 5, where the STING protein is down regulated by the compound.

8. The method of claim 5, the assay is selected from the group consisting of high-performance liquid chromatography, liquid chromatography-mass spectrometry, mass spectrometry, polymerase chain reaction, real time polymerase chain reaction, quantitative real time polymerase chain reaction, and thermal shift assay.

9. A method of inhibiting a functional activity of a STING protein (STimulator of INterferon Genes protein) in a human subject suffering from a disease and in need thereof, where the disease is selected from the group consisting of a systemic lupus erythamatosis and Aicardi-Goutieres Syndrome comprising:
   (a) determining whether the human subject has an upregulated functional activity of the STING protein, comprising:
      isolating a biological sample from the human subject having the inflammatory disease; and
      performing an assay on the biological sample to determine the functional activity of the STING protein;
   (b) if the human subject has an upregulated functional activity of the STING protein;
      then selecting a compound to inhibit the functional activity of the STING protein, where the compound has formula I:

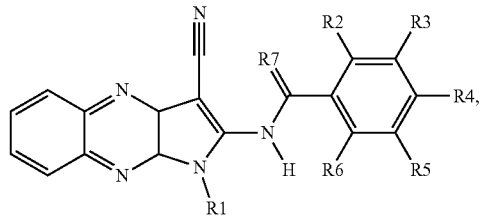

or a pharmaceutically acceptable salt, hydrate, ester, solvate, stereoisomer, or tautomer thereof, where $R_1$ is —($C_2$-$C_6$) alkyl-($C_3$-$C_6$) cycloalkenyl, —($C_1$-$C_6$) alkyl-($C_3$-$C_6$) cycloalkyl, —($C_1$-$C_6$) alkyl-($C_3$-$C_6$) substituted cycloalkenyl, —($C_1$-$C_6$) alkoxy-($C_3$-$C_6$) cycloalkenyl, —($C_2$-$C_6$) alkenyl-($C_3$-$C_6$) cycloalkenyl, where $R_2$, $R_3$, $R_4$, $R_5$ and $R_6$ are independently selected from the group consisting of —H, -halogen, —($C_1$-$C_6$) alkyl, —($C_3$-$C_6$) cycloalkyl, —($C_1$-$C_6$) haloalkyl, —($C_1$-$C_6$) alkoxy, —($C_1$-$C_6$) haloalkoxy, —($C_2$-$C_6$) alkenyl, —($C_2$-$C_6$) alkynyl, -nitro, —CN, —OH, —COOH, —SH, —$NH_2$, —NH($C_1$-$C_4$) alkyl, and —N(($C_1$-$C_4$) alkyl)$_2$, where $R_7$ is an atom selected from the group consisting of selenium and oxygen; and
      administering the compound to the human subject suffering from the disease to inhibit the functional activity of the STING protein in the human subject.

10. The method of claim 9, where the biological sample is selected from the group consisting of tissue, blood, saliva, urine, feces, semen, tears, other body fluids and extracts thereof.

11. The method of claim 9, where the STING protein is down regulated by the compound.

12. The method of claim 9, where the assay is selected from the group consisting of high-performance liquid chromatography, liquid chromatography-mass spectrometry, mass spectrometry, polymerase chain reaction, quantitative real time polymerase chain reaction, and thermal shift assay.

13. A method of inhibiting a STING protein (STimulator of INterferon Genes protein) in a human subject suffering from a disease and in need thereof, the method comprising:
(a) determining whether the human subject has an upregulated functional activity of STING protein, comprising:
isolating a biological sample from the human subject having the disease; and
performing an assay on the biological sample to determine the functional activity of the STING protein;
(b) if the human subject has an upregulated functional activity of the STING protein,
then selecting the STING protein antagonist selected from the group consisting of 2-chloro-N-[3-cyano-1-(2-phenoxyethyl)-1H-pyrrolo[2,3-$]quinoxalin-2-yl]benzamide, 2-chloro-N-[3-cyano-1-(2-methoxyethyl)-1H-pyrrolo[2,3-$]quinoxalin-2-yl]benzamide, 2-chloro-N-[3-cyano-1-(2-phenylethyl)-1H-pyrrolo[2,3-$]quinoxalin-2-yl]-5-methylbenzamide, 2-chloro-N-[3-cyano-1-(2-phenylethyl)-1H-pyrrolo[2,3-$]quinoxalin-2-yl]-3-fluorobenzamide, 2-chloro-N-[3-cyano-1-(2-phenylethyl)-1H-pyrrolo[2,3-$]quinoxalin-2-yl]-6-fluorobenzamide, 2-chloro-N-{3-cyano-1-[2-(3-fluorophenyl)ethyl]-1H-pyrrolo[2,3-$]quinoxalin-2-yl}benzamide, 2,3-dichloro-N-[3-cyano-1-(2-phenylethyl)-1H-pyrrolo[2,3-$]quinoxalin-2-yl]benzamide and 2-chloro-N-[3-cyano-1-(2-phenylethyl)-1H-pyrrolo[2,3-$]quinoxalin-2-yl]-3-methylbenzamide; and
administering the compound to the human subject suffering from the disease to inhibit the functional activity of the STING protein in the human subject.

14. The method of claim 13, where the biological sample is selected from the group consisting of tissue, blood, saliva, urine, feces, semen, tears, other body fluids and extracts thereof.

15. The method of claim 13, where the disease is systemic lupus erythamatosis.

16. The method of claim 13, where the disease is Aicardi-Goutieres Syndrome.

17. The method of claim 13, where the STING protein is down regulated by the compound.

18. The method of claim 13, where the assay is selected from the group consisting of high-performance liquid chromatography, liquid chromatography-mass spectrometry, mass spectrometry, polymerase chain reaction, real time polymerase chain reaction, quantitative real time polymerase chain reaction, and thermal shift assay.

19. The method of claim 1, where the disease is colitis.

20. The method of claim 9, where the disease is colitis.

* * * * *

```
                         SEQUENCE LISTING

Sequence total quantity: 1
SEQ ID NO: 1            moltype = AA   length = 237
FEATURE                 Location/Qualifiers
REGION                  1..237
                        note = Synthetic polypeptide
source                  1..237
                        mol_type = protein
                        organism = synthetic construct
SEQUENCE: 1
MNFNVAHGLA WSYYIGYLRL ILPELQARIR TYNQHYNNLL RGAVSQRLYI LLPLDCGVPD  60
```

```
NLSMADPNIR FLDKLPQQTG DHAGIKDRVY SNSIYELLEN GQRAGTCVLE YATPLQTLFA  120
MSQYSQAGFS REDRLEQAKL FCRTLEDILA DAPESQNNCR LIAYQEPADD SSFSLSQEVL  180
RHLRQEEKEE VTVGSLKTSA VPSTSTMSQE PELLISGMEK PLPLRTDFSL EHHHHHH     237
```